(12) United States Patent
Shelton, IV

(10) Patent No.: US 8,444,036 B2
(45) Date of Patent: May 21, 2013

(54) MOTOR DRIVEN SURGICAL FASTENER DEVICE WITH MECHANISMS FOR ADJUSTING A TISSUE GAP WITHIN THE END EFFECTOR

(75) Inventor: Frederick E. Shelton, IV, Hillsboro, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 284 days.

(21) Appl. No.: 12/846,237

(22) Filed: Jul. 29, 2010

(65) Prior Publication Data
US 2011/0011915 A1 Jan. 20, 2011

Related U.S. Application Data

(63) Continuation-in-part of application No. 12/693,461, filed on Jan. 26, 2010, now abandoned.

(60) Provisional application No. 61/150,387, filed on Feb. 6, 2009.

(51) Int. Cl.
*A61B 17/068* (2006.01)
(52) U.S. Cl.
USPC ..... 227/176.1; 227/19; 227/179.1; 227/175.3
(58) Field of Classification Search
USPC .......................... 227/19, 176.1, 179.1, 175.3
See application file for complete search history.

(56) References Cited

U.S. PATENT DOCUMENTS

| | | | |
|---|---|---|---|
| 2,853,074 A | 9/1958 | Olson | |
| 3,490,675 A | 1/1970 | Green et al. | |
| 3,551,987 A | 1/1971 | Wilkinson | |
| 3,643,851 A | 2/1972 | Green et al. | |
| 3,662,939 A | 5/1972 | Bryan | |
| 3,717,294 A | 2/1973 | Green | |
| 3,819,100 A | 6/1974 | Noiles et al. | |
| RE28,932 E | 8/1976 | Noiles et al. | |
| 4,331,277 A | 5/1982 | Green | |
| 4,383,634 A | 5/1983 | Green | |
| 4,396,139 A | 8/1983 | Hall et al. | |
| 4,402,445 A | 9/1983 | Green | |
| 4,415,112 A | 11/1983 | Green | |

(Continued)

FOREIGN PATENT DOCUMENTS

| | | |
|---|---|---|
| CA | 2458946 A1 | 3/2003 |
| CA | 2512960 A1 | 1/2006 |

(Continued)

OTHER PUBLICATIONS

Disclosed Anonymously, "Motor-Driven Surgical Stapler Improvements," Research Disclosure Database No. 526041, Published: Feb. 2008.

(Continued)

*Primary Examiner* — Brian D Nash

(57) ABSTRACT

A surgical fastener apparatus having a handle, an elongated shaft having a proximal end attached to the handle and a distal end extending therefrom. An end effector including a pair of jaws pivoted at a proximal end thereof and movable between an open and closed position. A cartridge containing a plurality of surgical fasteners, the cartridge attached to the end effector. An electrically powered actuator for deploying the surgical fasteners, the actuator including a power source and a motor. Means for electrically adjusting the amount of spacing between the jaws when the end effector is in the closed position.

19 Claims, 25 Drawing Sheets

U.S. PATENT DOCUMENTS

| | | |
|---|---|---|
| 4,429,695 A | 2/1984 | Green |
| 4,475,679 A | 10/1984 | Fleury, Jr. |
| 4,489,875 A | 12/1984 | Crawford et al. |
| 4,500,024 A | 2/1985 | DiGiovanni et al. |
| 4,505,414 A | 3/1985 | Filipi |
| 4,506,671 A | 3/1985 | Green |
| 4,522,327 A | 6/1985 | Korthoff et al. |
| 4,530,453 A | 7/1985 | Green |
| 4,566,620 A | 1/1986 | Green et al. |
| 4,573,622 A | 3/1986 | Green et al. |
| 4,580,712 A | 4/1986 | Green |
| 4,610,383 A | 9/1986 | Rothfuss et al. |
| 4,619,262 A | 10/1986 | Taylor |
| 4,629,107 A | 12/1986 | Fedotov et al. |
| 4,632,290 A | 12/1986 | Green et al. |
| 4,664,305 A | 5/1987 | Blake, III et al. |
| 4,671,445 A | 6/1987 | Barker et al. |
| 4,715,520 A | 12/1987 | Roehr, Jr. et al. |
| 4,728,020 A | 3/1988 | Green et al. |
| 4,752,024 A | 6/1988 | Green et al. |
| 4,754,909 A | 7/1988 | Barker et al. |
| 4,767,044 A | 8/1988 | Green |
| 4,805,823 A | 2/1989 | Rothfuss |
| 4,809,695 A | 3/1989 | Gwathmey et al. |
| 4,817,847 A | 4/1989 | Redtenbacher et al. |
| 4,819,853 A | 4/1989 | Green |
| 4,821,939 A | 4/1989 | Green |
| 4,844,068 A | 7/1989 | Arata et al. |
| 4,869,414 A | 9/1989 | Green et al. |
| 4,869,415 A | 9/1989 | Fox |
| 4,941,623 A | 7/1990 | Pruitt |
| 4,944,443 A | 7/1990 | Oddsen et al. |
| 5,065,929 A | 11/1991 | Schulze et al. |
| 5,074,454 A | 12/1991 | Peters |
| 5,129,570 A | 7/1992 | Schulze et al. |
| 5,137,198 A | 8/1992 | Nobis et al. |
| 5,141,144 A | 8/1992 | Foslien et al. |
| 5,221,036 A | 6/1993 | Takase |
| 5,307,976 A | 5/1994 | Olson et al. |
| 5,383,880 A | 1/1995 | Hooven |
| 5,403,312 A | 4/1995 | Yates et al. |
| 5,405,072 A | 4/1995 | Zlock et al. |
| 5,405,073 A | 4/1995 | Porter |
| 5,413,272 A | 5/1995 | Green et al. |
| 5,417,361 A | 5/1995 | Williamson, IV |
| 5,433,721 A | 7/1995 | Hooven et al. |
| 5,452,837 A | 9/1995 | Williamson, IV et al. |
| 5,465,894 A | 11/1995 | Clark et al. |
| 5,465,895 A | 11/1995 | Knodel et al. |
| 5,467,911 A | 11/1995 | Tsuruta et al. |
| 5,480,089 A | 1/1996 | Blewett |
| 5,482,197 A | 1/1996 | Green et al. |
| 5,484,095 A | 1/1996 | Green et al. |
| 5,485,947 A | 1/1996 | Olson et al. |
| 5,485,952 A | 1/1996 | Fontayne |
| 5,487,499 A | 1/1996 | Sorrentino et al. |
| 5,487,500 A | 1/1996 | Knodel et al. |
| 5,489,058 A | 2/1996 | Plyley et al. |
| 5,497,933 A | 3/1996 | DeFonzo et al. |
| 5,503,320 A | 4/1996 | Webster et al. |
| 5,505,363 A | 4/1996 | Green et al. |
| 5,507,426 A | 4/1996 | Young et al. |
| 5,509,596 A | 4/1996 | Green et al. |
| 5,518,163 A | 5/1996 | Hooven |
| 5,518,164 A | 5/1996 | Hooven |
| 5,529,235 A | 6/1996 | Boiarski et al. |
| 5,533,661 A | 7/1996 | Main et al. |
| 5,535,934 A | 7/1996 | Boiarski et al. |
| 5,535,937 A | 7/1996 | Boiarski et al. |
| 5,540,375 A | 7/1996 | Bolanos et al. |
| 5,542,594 A | 8/1996 | McKean et al. |
| 5,553,765 A | 9/1996 | Knodel et al. |
| 5,560,530 A | 10/1996 | Bolanos et al. |
| 5,560,532 A | 10/1996 | DeFonzo et al. |
| 5,562,241 A | 10/1996 | Knodel et al. |
| 5,564,615 A | 10/1996 | Bishop et al. |
| 5,577,654 A | 11/1996 | Bishop |
| 5,579,978 A | 12/1996 | Green et al. |
| 5,580,067 A | 12/1996 | Hamblin et al. |
| 5,586,711 A | 12/1996 | Plyley et al. |
| 5,588,579 A | 12/1996 | Schnut et al. |
| 5,588,580 A | 12/1996 | Paul et al. |
| 5,588,581 A | 12/1996 | Conlon et al. |
| 5,601,224 A | 2/1997 | Bishop et al. |
| 5,603,443 A | 2/1997 | Clark et al. |
| 5,605,273 A | 2/1997 | Hamblin et al. |
| 5,607,094 A | 3/1997 | Clark et al. |
| 5,607,095 A | 3/1997 | Smith et al. |
| 5,609,285 A | 3/1997 | Grant et al. |
| 5,628,446 A | 5/1997 | Geiste et al. |
| 5,630,539 A | 5/1997 | Plyley et al. |
| 5,630,540 A | 5/1997 | Blewett |
| 5,632,432 A | 5/1997 | Schulze et al. |
| 5,632,433 A | 5/1997 | Grant et al. |
| 5,634,584 A | 6/1997 | Okorocha et al. |
| 5,636,780 A | 6/1997 | Green et al. |
| 5,639,008 A | 6/1997 | Gallagher et al. |
| 5,651,491 A | 7/1997 | Heaton et al. |
| 5,653,373 A | 8/1997 | Green et al. |
| 5,653,374 A | 8/1997 | Young et al. |
| 5,655,698 A | 8/1997 | Yoon |
| 5,657,921 A | 8/1997 | Young et al. |
| 5,662,258 A | 9/1997 | Knodel et al. |
| 5,662,260 A | 9/1997 | Yoon |
| 5,667,517 A | 9/1997 | Hooven |
| 5,669,544 A | 9/1997 | Schulze et al. |
| 5,673,840 A | 10/1997 | Schulze et al. |
| 5,673,841 A | 10/1997 | Schulze et al. |
| 5,680,981 A | 10/1997 | Mililli et al. |
| 5,680,982 A | 10/1997 | Schulze et al. |
| 5,680,983 A | 10/1997 | Plyley et al. |
| 5,685,474 A | 11/1997 | Seeber |
| 5,688,270 A | 11/1997 | Yates et al. |
| 5,690,269 A | 11/1997 | Bolanos et al. |
| 5,692,668 A | 12/1997 | Schulze et al. |
| 5,697,543 A | 12/1997 | Burdorff |
| 5,704,534 A | 1/1998 | Huitema et al. |
| 5,706,998 A | 1/1998 | Plyley et al. |
| 5,709,334 A | 1/1998 | Sorrentino et al. |
| 5,709,680 A | 1/1998 | Yates et al. |
| 5,711,472 A | 1/1998 | Bryan |
| 5,713,505 A | 2/1998 | Huitema |
| 5,715,987 A | 2/1998 | Kelley et al. |
| 5,718,360 A | 2/1998 | Green et al. |
| 5,732,871 A | 3/1998 | Clark et al. |
| 5,732,872 A | 3/1998 | Bolduc et al. |
| 5,743,456 A | 4/1998 | Jones et al. |
| 5,752,644 A | 5/1998 | Bolanos et al. |
| 5,758,814 A | 6/1998 | Gallagher et al. |
| 5,762,256 A | 6/1998 | Mastri et al. |
| 5,779,130 A | 7/1998 | Alesi et al. |
| 5,779,131 A | 7/1998 | Knodel et al. |
| 5,779,132 A | 7/1998 | Knodel et al. |
| 5,782,396 A | 7/1998 | Mastri et al. |
| 5,782,397 A | 7/1998 | Koukline |
| 5,785,232 A | 7/1998 | Vidal et al. |
| 5,792,165 A | 8/1998 | Klieman et al. |
| 5,797,536 A | 8/1998 | Smith et al. |
| 5,797,537 A | 8/1998 | Oberlin et al. |
| 5,797,538 A | 8/1998 | Heaton et al. |
| 5,799,857 A | 9/1998 | Robertson et al. |
| 5,820,009 A | 10/1998 | Melling et al. |
| 5,826,776 A | 10/1998 | Schulze et al. |
| 5,829,662 A | 11/1998 | Allen et al. |
| 5,836,503 A | 11/1998 | Ehrenfels et al. |
| 5,839,639 A | 11/1998 | Sauer et al. |
| 5,855,311 A | 1/1999 | Hamblin et al. |
| 5,865,361 A | 2/1999 | Milliman et al. |
| 5,871,135 A | 2/1999 | Williamson IV et al. |
| 5,893,506 A | 4/1999 | Powell |
| 5,901,895 A | 5/1999 | Heaton et al. |
| 5,911,353 A | 6/1999 | Bolanos et al. |
| 5,915,616 A | 6/1999 | Viola et al. |
| 5,918,791 A | 7/1999 | Sorrentino et al. |
| 5,937,951 A | 8/1999 | Izuchukwu et al. |
| 5,941,442 A | 8/1999 | Geiste et al. |
| 5,954,259 A | 9/1999 | Viola et al. |

| | | | |
|---|---|---|---|
| 6,010,054 A | 1/2000 | Johnson et al. |
| 6,032,849 A | 3/2000 | Mastri et al. |
| 6,053,390 A | 4/2000 | Green et al. |
| 6,102,271 A | 8/2000 | Longo et al. |
| 6,119,913 A | 9/2000 | Adams et al. |
| 6,126,058 A | 10/2000 | Adams et al. |
| 6,193,129 B1 | 2/2001 | Bittner et al. |
| 6,202,914 B1 | 3/2001 | Geiste et al. |
| 6,241,139 B1 | 6/2001 | Milliman et al. |
| 6,250,532 B1 | 6/2001 | Green et al. |
| 6,264,086 B1 | 7/2001 | McGuckin, Jr. |
| 6,264,087 B1 | 7/2001 | Whitman |
| 6,302,311 B1 | 10/2001 | Adams et al. |
| 6,315,184 B1 | 11/2001 | Whitman |
| 6,330,965 B1 | 12/2001 | Milliman et al. |
| 6,450,391 B1 | 9/2002 | Kayan et al. |
| 6,488,196 B1 | 12/2002 | Fenton, Jr. |
| 6,488,197 B1 | 12/2002 | Whitman |
| 6,491,201 B1 | 12/2002 | Whitman |
| 6,505,768 B2 | 1/2003 | Whitman |
| 6,578,751 B2 | 6/2003 | Hartwick |
| 6,588,643 B2 | 7/2003 | Bolduc et al. |
| 6,601,749 B2 | 8/2003 | Sullivan et al. |
| 6,619,529 B2 | 9/2003 | Green et al. |
| 6,629,630 B2 | 10/2003 | Adams |
| 6,644,532 B2 | 11/2003 | Green et al. |
| 6,646,307 B1 | 11/2003 | Yu et al. |
| 6,681,978 B2 | 1/2004 | Geiste et al. |
| 6,681,979 B2 | 1/2004 | Whitman |
| 6,695,199 B2 | 2/2004 | Whitman |
| 6,698,643 B2 | 3/2004 | Whitman |
| 6,716,223 B2 | 4/2004 | Leopold et al. |
| 6,722,552 B2 | 4/2004 | Fenton, Jr. |
| 6,755,338 B2 | 6/2004 | Hahnen et al. |
| 6,767,352 B2 | 7/2004 | Field et al. |
| 6,769,594 B2 | 8/2004 | Orban, III |
| 6,786,382 B1 | 9/2004 | Hoffman |
| 6,805,273 B2 | 10/2004 | Bilotti et al. |
| 6,817,508 B1 | 11/2004 | Racenet et al. |
| 6,817,509 B2 | 11/2004 | Geiste et al. |
| 6,830,174 B2 | 12/2004 | Hillstead et al. |
| 6,843,403 B2 | 1/2005 | Whitman |
| RE38,708 E | 3/2005 | Bolanos et al. |
| 6,866,178 B2 | 3/2005 | Adams et al. |
| 6,874,669 B2 | 4/2005 | Adams et al. |
| 6,877,647 B2 | 4/2005 | Green et al. |
| 6,905,057 B2 | 6/2005 | Swayze et al. |
| 6,945,444 B2 | 9/2005 | Gresham et al. |
| 6,953,138 B1 | 10/2005 | Dworak et al. |
| 6,953,139 B2 | 10/2005 | Milliman et al. |
| 6,959,851 B2 | 11/2005 | Heinrich |
| 6,959,852 B2 | 11/2005 | Shelton, IV et al. |
| 6,964,363 B2 | 11/2005 | Wales et al. |
| 6,978,921 B2 | 12/2005 | Shelton, IV et al. |
| 6,978,922 B2 | 12/2005 | Bilotti et al. |
| 6,981,628 B2 | 1/2006 | Wales |
| 6,986,451 B1 | 1/2006 | Mastri et al. |
| 6,988,650 B2 | 1/2006 | Schwemberger et al. |
| 7,000,818 B2 | 2/2006 | Shelton, IV et al. |
| 7,000,819 B2 | 2/2006 | Swayze et al. |
| 7,032,798 B2 | 4/2006 | Whitman et al. |
| 7,032,799 B2 | 4/2006 | Viola et al. |
| 7,044,352 B2 | 5/2006 | Shelton, IV et al. |
| 7,044,353 B2 | 5/2006 | Mastri et al. |
| 7,055,731 B2 | 6/2006 | Shelton, IV et al. |
| 7,070,083 B2 | 7/2006 | Jankowski |
| 7,080,769 B2 | 7/2006 | Vresh et al. |
| 7,083,075 B2 | 8/2006 | Swayze et al. |
| 7,111,769 B2 | 9/2006 | Wales et al. |
| 7,114,642 B2 | 10/2006 | Whitman |
| 7,121,446 B2 | 10/2006 | Arad et al. |
| 7,128,253 B2 | 10/2006 | Mastri et al. |
| 7,128,254 B2 | 10/2006 | Shelton, IV et al. |
| 7,140,527 B2 | 11/2006 | Ehrenfels et al. |
| 7,140,528 B2 | 11/2006 | Shelton, IV |
| 7,143,926 B2 | 12/2006 | Shelton, IV et al. |
| 7,147,138 B2 | 12/2006 | Shelton, IV |
| 7,147,139 B2 | 12/2006 | Schwemberger et al. |
| 7,159,750 B2 | 1/2007 | Racenet et al. |
| 7,168,604 B2 | 1/2007 | Milliman et al. |
| 7,182,239 B1 | 2/2007 | Myers |
| 7,188,758 B2 | 3/2007 | Viola et al. |
| 7,207,471 B2 | 4/2007 | Heinrich et al. |
| 7,207,472 B2 | 4/2007 | Wukusick et al. |
| 7,210,609 B2 | 5/2007 | Leiboff et al. |
| 7,213,736 B2 | 5/2007 | Wales et al. |
| 7,225,964 B2 | 6/2007 | Mastri et al. |
| 7,234,624 B2 | 6/2007 | Gresham et al. |
| 7,237,708 B1 | 7/2007 | Guy et al. |
| 7,246,734 B2 | 7/2007 | Shelton, IV |
| 7,258,262 B2 | 8/2007 | Mastri et al. |
| 7,278,562 B2 | 10/2007 | Mastri et al. |
| 7,278,563 B1 | 10/2007 | Green |
| 7,296,724 B2 | 11/2007 | Green et al. |
| 7,303,106 B2 | 12/2007 | Milliman et al. |
| 7,303,107 B2 | 12/2007 | Milliman et al. |
| 7,303,108 B2 | 12/2007 | Shelton, IV |
| 7,308,998 B2 | 12/2007 | Mastri et al. |
| 7,328,828 B2 | 2/2008 | Ortiz et al. |
| 7,328,829 B2 | 2/2008 | Arad et al. |
| 7,334,717 B2 | 2/2008 | Rethy et al. |
| 7,354,447 B2 | 4/2008 | Shelton, IV et al. |
| 7,357,287 B2 | 4/2008 | Shelton, IV et al. |
| 7,364,060 B2 | 4/2008 | Milliman |
| 7,364,061 B2 | 4/2008 | Swayze et al. |
| 7,380,695 B2 | 6/2008 | Doll et al. |
| 7,380,696 B2 | 6/2008 | Shelton, IV et al. |
| 7,388,217 B2 | 6/2008 | Buschbeck et al. |
| 7,398,907 B2 | 7/2008 | Racenet et al. |
| 7,398,908 B2 | 7/2008 | Holsten et al. |
| 7,404,508 B2 | 7/2008 | Smith et al. |
| 7,404,509 B2 | 7/2008 | Ortiz et al. |
| 7,407,075 B2 | 8/2008 | Holsten et al. |
| 7,407,078 B2 | 8/2008 | Shelton, IV et al. |
| 7,410,086 B2 | 8/2008 | Ortiz et al. |
| 7,416,101 B2 | 8/2008 | Shelton, IV et al. |
| 7,419,080 B2 | 9/2008 | Smith et al. |
| 7,422,136 B1 | 9/2008 | Marczyk |
| 7,422,139 B2 | 9/2008 | Shelton, IV et al. |
| 7,424,965 B2 | 9/2008 | Racenet et al. |
| 7,431,188 B1 | 10/2008 | Marczyk |
| 7,431,189 B2 | 10/2008 | Shelton, IV et al. |
| 7,434,717 B2 | 10/2008 | Shelton, IV et al. |
| 7,438,209 B1 | 10/2008 | Hess et al. |
| 7,441,684 B2 | 10/2008 | Shelton, IV et al. |
| 7,441,685 B1 | 10/2008 | Boudreaux |
| 7,448,525 B2 | 11/2008 | Shelton, IV et al. |
| 7,455,208 B2 | 11/2008 | Wales et al. |
| 7,464,846 B2 | 12/2008 | Shelton, IV et al. |
| 7,464,849 B2 | 12/2008 | Shelton, IV et al. |
| 7,467,740 B2 | 12/2008 | Shelton, IV et al. |
| 7,472,815 B2 | 1/2009 | Shelton, IV et al. |
| 7,481,347 B2 | 1/2009 | Roy |
| 7,481,349 B2 | 1/2009 | Holsten et al. |
| 7,490,749 B2 | 2/2009 | Schall et al. |
| 7,494,039 B2 | 2/2009 | Racenet et al. |
| 7,500,979 B2 | 3/2009 | Hueil et al. |
| 7,506,790 B2 | 3/2009 | Shelton, IV |
| 7,506,791 B2 | 3/2009 | Omaits et al. |
| 7,510,107 B2 | 3/2009 | Timm et al. |
| 7,546,940 B2 | 6/2009 | Milliman et al. |
| 7,549,563 B2 | 6/2009 | Mather et al. |
| 7,549,564 B2 | 6/2009 | Boudreaux |
| 7,556,185 B2 | 7/2009 | Viola |
| 7,556,186 B2 | 7/2009 | Milliman |
| 7,559,450 B2 | 7/2009 | Wales et al. |
| 7,559,452 B2 | 7/2009 | Wales et al. |
| 7,568,603 B2 | 8/2009 | Shelton, IV et al. |
| 7,568,604 B2 | 8/2009 | Ehrenfels et al. |
| 7,575,144 B2 | 8/2009 | Ortiz et al. |
| 7,588,175 B2 | 9/2009 | Timm et al. |
| 7,588,176 B2 | 9/2009 | Timm et al. |
| 7,597,229 B2 | 10/2009 | Boudreaux et al. |
| 7,604,150 B2 | 10/2009 | Boudreaux |
| 7,604,151 B2 | 10/2009 | Hess et al. |
| 7,607,557 B2 | 10/2009 | Shelton, IV et al. |
| 7,611,038 B2 | 11/2009 | Racenet et al. |
| 7,624,902 B2 | 12/2009 | Marczyk et al. |

| | | | | | | |
|---|---|---|---|---|---|---|
| 7,631,793 B2 | 12/2009 | Rethy et al. | 8,196,796 B2 | 6/2012 | Shelton, IV et al. |
| 7,637,409 B2 | 12/2009 | Marczyk | 8,205,781 B2 | 6/2012 | Baxter, III et al. |
| 7,644,848 B2 | 1/2010 | Swayze et al. | 8,220,688 B2 | 7/2012 | Laurent et al. |
| 7,658,311 B2 | 2/2010 | Boudreaux | 8,245,901 B2 | 8/2012 | Stopek |
| 7,658,312 B2 | 2/2010 | Vidal et al. | 8,256,654 B2 | 9/2012 | Bettuchi et al. |
| 7,665,646 B2 | 2/2010 | Prommersberger | 8,267,300 B2 | 9/2012 | Boudreaux |
| 7,665,647 B2 | 2/2010 | Shelton, IV et al. | 8,292,155 B2 | 10/2012 | Shelton, Iv et al. |
| 7,669,746 B2 | 3/2010 | Shelton, IV | 8,333,313 B2 | 12/2012 | Boudreaux et al. |
| 7,669,747 B2 | 3/2010 | Weisenburgh, II et al. | 2002/0117534 A1 | 8/2002 | Green et al. |
| 7,670,334 B2 | 3/2010 | Hueil et al. | 2003/0130677 A1 | 7/2003 | Whitman et al. |
| 7,673,780 B2 | 3/2010 | Shelton, IV et al. | 2004/0094597 A1 | 5/2004 | Whitman et al. |
| 7,673,781 B2 | 3/2010 | Swayze et al. | 2004/0108357 A1 | 6/2004 | Milliman et al. |
| 7,673,782 B2 | 3/2010 | Hess et al. | 2004/0164123 A1 | 8/2004 | Racenet et al. |
| 7,673,783 B2 | 3/2010 | Morgan et al. | 2004/0173659 A1 | 9/2004 | Green et al. |
| 7,699,204 B2 | 4/2010 | Viola | 2004/0222268 A1 | 11/2004 | Bilotti et al. |
| 7,708,180 B2 | 5/2010 | Murray et al. | 2004/0232201 A1 | 11/2004 | Wenchell et al. |
| 7,717,312 B2 | 5/2010 | Beetel | 2005/0103819 A1 | 5/2005 | Racenet et al. |
| 7,721,930 B2 | 5/2010 | McKenna et al. | 2005/0131390 A1 | 6/2005 | Heinrich et al. |
| 7,721,931 B2 | 5/2010 | Shelton, IV et al. | 2005/0145675 A1 | 7/2005 | Hartwick et al. |
| 7,721,934 B2 | 5/2010 | Shelton, IV et al. | 2005/0184121 A1 | 8/2005 | Heinrich |
| 7,721,936 B2 | 5/2010 | Shalton, IV et al. | 2005/0189397 A1 | 9/2005 | Jankowski |
| 7,726,537 B2 | 6/2010 | Olson et al. | 2005/0263563 A1 | 12/2005 | Racenet et al. |
| 7,726,538 B2 | 6/2010 | Holsten et al. | 2005/0274768 A1 | 12/2005 | Cummins et al. |
| 7,731,072 B2 | 6/2010 | Timm et al. | 2006/0011699 A1 | 1/2006 | Olson et al. |
| 7,735,703 B2 | 6/2010 | Morgan et al. | 2006/0049229 A1 | 3/2006 | Milliman et al. |
| 7,738,971 B2 | 6/2010 | Swayze et al. | 2006/0108393 A1 | 5/2006 | Heinrich et al. |
| 7,740,159 B2 | 6/2010 | Shelton, IV et al. | 2006/0180634 A1 | 8/2006 | Shelton, IV et al. |
| 7,743,960 B2 | 6/2010 | Whitman et al. | 2006/0226196 A1 | 10/2006 | Hueil et al. |
| 7,753,245 B2 | 7/2010 | Boudreaux et al. | 2006/0278680 A1 | 12/2006 | Viola et al. |
| 7,753,904 B2 | 7/2010 | Shelton, IV et al. | 2006/0278681 A1 | 12/2006 | Viola et al. |
| 7,766,209 B2 | 8/2010 | Baxter, III et al. | 2006/0289602 A1 | 12/2006 | Wales et al. |
| 7,766,210 B2 | 8/2010 | Shelton, IV et al. | 2007/0023476 A1 | 2/2007 | Whitman et al. |
| 7,770,775 B2 | 8/2010 | Shelton, IV et al. | 2007/0023477 A1 | 2/2007 | Whitman et al. |
| 7,780,054 B2 | 8/2010 | Wales | 2007/0034668 A1 | 2/2007 | Holsten et al. |
| 7,784,662 B2 | 8/2010 | Wales et al. | 2007/0084897 A1 | 4/2007 | Shelton, IV et al. |
| 7,793,812 B2 | 9/2010 | Moore et al. | 2007/0102472 A1 | 5/2007 | Shelton, IV |
| 7,794,475 B2 | 9/2010 | Hess et al. | 2007/0106317 A1 | 5/2007 | Shelton, IV et al. |
| 7,798,386 B2 | 9/2010 | Schall et al. | 2007/0114261 A1 | 5/2007 | Ortiz et al. |
| 7,799,039 B2 | 9/2010 | Shelton, IV et al. | 2007/0170225 A1 | 7/2007 | Shelton, IV et al. |
| 7,803,151 B2 | 9/2010 | Whitman | 2007/0175949 A1 | 8/2007 | Shelton, IV et al. |
| 7,810,692 B2 | 10/2010 | Hall et al. | 2007/0175950 A1 | 8/2007 | Shelton, IV et al. |
| 7,810,693 B2 | 10/2010 | Broehl et al. | 2007/0175951 A1 | 8/2007 | Shelton, IV et al. |
| 7,819,296 B2 | 10/2010 | Hueil et al. | 2007/0175953 A1 | 8/2007 | Shelton, IV et al. |
| 7,819,297 B2 | 10/2010 | Doll et al. | 2007/0175955 A1 | 8/2007 | Shelton, IV et al. |
| 7,819,298 B2 | 10/2010 | Hall et al. | 2007/0181632 A1 | 8/2007 | Milliman |
| 7,819,299 B2 | 10/2010 | Shelton, IV et al. | 2007/0194079 A1 | 8/2007 | Hueil et al. |
| 7,832,408 B2 | 11/2010 | Shelton, IV et al. | 2007/0194081 A1 | 8/2007 | Hueil et al. |
| 7,832,611 B2 | 11/2010 | Boyden et al. | 2007/0194082 A1 | 8/2007 | Morgan et al. |
| 7,832,612 B2 | 11/2010 | Baxter, III et al. | 2007/0221700 A1 | 9/2007 | Ortiz et al. |
| 7,837,080 B2 | 11/2010 | Schwemberger | 2007/0221701 A1 | 9/2007 | Ortiz et al. |
| 7,837,081 B2 | 11/2010 | Holsten et al. | 2007/0225562 A1 | 9/2007 | Spivey et al. |
| 7,845,533 B2 | 12/2010 | Marczyk et al. | 2007/0239028 A1 | 10/2007 | Houser et al. |
| 7,845,537 B2 | 12/2010 | Shelton, IV et al. | 2007/0246505 A1 | 10/2007 | Pace-Floridia et al. |
| 7,857,185 B2 | 12/2010 | Swayze et al. | 2007/0295780 A1 | 12/2007 | Shelton et al. |
| 7,857,186 B2 | 12/2010 | Baxter, III et al. | 2008/0029570 A1 | 2/2008 | Shelton et al. |
| 7,861,906 B2 | 1/2011 | Doll et al. | 2008/0029573 A1 | 2/2008 | Shelton et al. |
| 7,866,527 B2 | 1/2011 | Hall et al. | 2008/0029574 A1 | 2/2008 | Shelton et al. |
| 7,905,381 B2 | 3/2011 | Baxter, III et al. | 2008/0029575 A1 | 2/2008 | Shelton et al. |
| 7,909,221 B2 | 3/2011 | Viola et al. | 2008/0035701 A1 | 2/2008 | Racenet et al. |
| 7,922,063 B2 | 4/2011 | Zemlok et al. | 2008/0041917 A1 | 2/2008 | Racenet et al. |
| 7,938,307 B2 | 5/2011 | Bettuchi | 2008/0078800 A1 | 4/2008 | Hess et al. |
| 7,950,560 B2 | 5/2011 | Zemlok et al. | 2008/0078802 A1 | 4/2008 | Hess et al. |
| 7,967,180 B2 | 6/2011 | Scirica | 2008/0078803 A1 | 4/2008 | Shelton et al. |
| 8,011,551 B2 | 9/2011 | Marczyk et al. | 2008/0078804 A1 | 4/2008 | Shelton et al. |
| 8,011,555 B2 | 9/2011 | Tarinelli et al. | 2008/0078806 A1 | 4/2008 | Omaits et al. |
| 8,028,883 B2 | 10/2011 | Stopek | 2008/0078807 A1 | 4/2008 | Hess et al. |
| 8,038,045 B2 | 10/2011 | Bettuchi et al. | 2008/0078808 A1 | 4/2008 | Hess et al. |
| 8,038,046 B2 | 10/2011 | Smith et al. | 2008/0082115 A1 | 4/2008 | Morgan et al. |
| D650,074 S | 12/2011 | Hunt et al. | 2008/0082125 A1 | 4/2008 | Murray et al. |
| 8,091,756 B2 | 1/2012 | Viola | 2008/0082126 A1 | 4/2008 | Murray et al. |
| 8,113,410 B2 | 2/2012 | Hall et al. | 2008/0083813 A1 | 4/2008 | Zemlok et al. |
| 8,123,103 B2 | 2/2012 | Milliman | 2008/0114385 A1 | 5/2008 | Byrum et al. |
| 8,136,712 B2 | 3/2012 | Zingman | 2008/0167522 A1 | 7/2008 | Giordano et al. |
| 8,141,762 B2 | 3/2012 | Bedi et al. | 2008/0167644 A1 | 7/2008 | Shelton et al. |
| 8,152,041 B2 | 4/2012 | Kostrzewski | 2008/0167671 A1 | 7/2008 | Giordano et al. |
| 8,157,152 B2 | 4/2012 | Holsten et al. | 2008/0167672 A1 | 7/2008 | Giordano et al. |
| 8,157,153 B2 | 4/2012 | Shelton, IV et al. | 2008/0169328 A1 | 7/2008 | Shelton |
| 8,167,185 B2 | 5/2012 | Shelton, IV et al. | 2008/0169329 A1 | 7/2008 | Shelton et al. |
| 8,172,124 B2 | 5/2012 | Shelton, IV et al. | 2008/0169330 A1 | 7/2008 | Shelton et al. |

| | | | | | | |
|---|---|---|---|---|---|---|
| 2008/0169331 A1 | 7/2008 | Shelton et al. | | 2010/0193569 A1 | 8/2010 | Yates et al. |
| 2008/0169332 A1 | 7/2008 | Shelton et al. | | 2010/0198220 A1 | 8/2010 | Boudreaux et al. |
| 2008/0169333 A1 | 7/2008 | Shelton et al. | | 2010/0200637 A1 | 8/2010 | Beetel |
| 2008/0185419 A1 | 8/2008 | Smith et al. | | 2010/0213241 A1 | 8/2010 | Bedi et al. |
| 2008/0197167 A1 | 8/2008 | Viola et al. | | 2010/0222901 A1 | 9/2010 | Swayze et al. |
| 2008/0210738 A1 | 9/2008 | Shelton et al. | | 2010/0224669 A1 | 9/2010 | Shelton, IV et al. |
| 2008/0237296 A1 | 10/2008 | Boudreaux et al. | | 2010/0230465 A1 | 9/2010 | Smith et al. |
| 2008/0251568 A1 | 10/2008 | Zemlok et al. | | 2010/0237132 A1 | 9/2010 | Measamer et al. |
| 2008/0251569 A1 | 10/2008 | Smith et al. | | 2010/0243707 A1 | 9/2010 | Olson et al. |
| 2008/0283570 A1 | 11/2008 | Boyden et al. | | 2010/0243708 A1 | 9/2010 | Aranyi et al. |
| 2008/0290134 A1 | 11/2008 | Bettuchi et al. | | 2010/0243709 A1 | 9/2010 | Hess et al. |
| 2008/0296346 A1 | 12/2008 | Shelton, IV et al. | | 2010/0258611 A1 | 10/2010 | Smith et al. |
| 2008/0300580 A1 | 12/2008 | Shelton, IV et al. | | 2010/0264193 A1 | 10/2010 | Huang et al. |
| 2008/0300613 A1 | 12/2008 | Shelton, IV et al. | | 2010/0264194 A1 | 10/2010 | Huang et al. |
| 2008/0308602 A1 | 12/2008 | Timm et al. | | 2010/0276471 A1 | 11/2010 | Whitman |
| 2008/0308603 A1 | 12/2008 | Shelton et al. | | 2010/0294827 A1 | 11/2010 | Boyden et al. |
| 2008/0308608 A1 | 12/2008 | Prommersberger | | 2010/0294829 A1 | 11/2010 | Giordano et al. |
| 2008/0314957 A1 | 12/2008 | Boudreaux | | 2010/0301095 A1 | 12/2010 | Shelton, IV et al. |
| 2008/0314960 A1 | 12/2008 | Marczyk et al. | | 2010/0301096 A1 | 12/2010 | Moore et al. |
| 2009/0001121 A1 | 1/2009 | Hess et al. | | 2010/0305552 A1 | 12/2010 | Shelton, IV et al. |
| 2009/0001122 A1 | 1/2009 | Prommersberger et al. | | 2010/0308100 A1 | 12/2010 | Boudreaux |
| 2009/0001124 A1 | 1/2009 | Hess et al. | | 2011/0006099 A1 | 1/2011 | Hall et al. |
| 2009/0001130 A1 | 1/2009 | Hess et al. | | 2011/0006101 A1 | 1/2011 | Hall et al. |
| 2009/0005807 A1 | 1/2009 | Hess et al. | | 2011/0006103 A1 | 1/2011 | Laurent et al. |
| 2009/0005808 A1 | 1/2009 | Hess et al. | | 2011/0011914 A1 | 1/2011 | Baxter, III et al. |
| 2009/0005809 A1 | 1/2009 | Hess et al. | | 2011/0017801 A1 | 1/2011 | Zemlok et al. |
| 2009/0012556 A1 | 1/2009 | Boudreaux et al. | | 2011/0024477 A1 | 2/2011 | Hall |
| 2009/0057369 A1 | 3/2009 | Smith et al. | | 2011/0024478 A1 | 2/2011 | Shelton, IV |
| 2009/0076534 A1 | 3/2009 | Shelton, IV et al. | | 2011/0024479 A1 | 2/2011 | Swensgard et al. |
| 2009/0090763 A1 | 4/2009 | Zemlok et al. | | 2011/0036887 A1 | 2/2011 | Zemlok et al. |
| 2009/0108048 A1 | 4/2009 | Zemlok et al. | | 2011/0042441 A1 | 2/2011 | Shelton, IV et al. |
| 2009/0114701 A1 | 5/2009 | Zemlok et al. | | 2011/0060363 A1 | 3/2011 | Hess et al. |
| 2009/0149871 A9 | 6/2009 | Kagan et al. | | 2011/0068145 A1 | 3/2011 | Bedi et al. |
| 2009/0206125 A1 | 8/2009 | Huitema et al. | | 2011/0068148 A1 | 3/2011 | Hall et al. |
| 2009/0206126 A1 | 8/2009 | Huitema et al. | | 2011/0084112 A1 | 4/2011 | Kostrzewski |
| 2009/0206131 A1 | 8/2009 | Weisenburgh, II et al. | | 2011/0084115 A1 | 4/2011 | Bedi et al. |
| 2009/0206132 A1 | 8/2009 | Hueil et al. | | 2011/0087276 A1 | 4/2011 | Bedi et al. |
| 2009/0206133 A1 | 8/2009 | Morgan et al. | | 2011/0095068 A1 | 4/2011 | Patel |
| 2009/0206137 A1 | 8/2009 | Hall et al. | | 2011/0101065 A1 | 5/2011 | Milliman |
| 2009/0206138 A1 | 8/2009 | Smith et al. | | 2011/0114697 A1 | 5/2011 | Baxter, III et al. |
| 2009/0206139 A1 | 8/2009 | Hall et al. | | 2011/0114698 A1 | 5/2011 | Baxter, III et al. |
| 2009/0206140 A1 | 8/2009 | Scheib et al. | | 2011/0114699 A1 | 5/2011 | Baxter, III et al. |
| 2009/0206141 A1 | 8/2009 | Huitema et al. | | 2011/0114700 A1 | 5/2011 | Baxter, III et al. |
| 2009/0206142 A1 | 8/2009 | Huitema et al. | | 2011/0118761 A1 | 5/2011 | Baxter, III et al. |
| 2009/0206143 A1 | 8/2009 | Huitema et al. | | 2011/0125176 A1 | 5/2011 | Yates et al. |
| 2009/0206144 A1 | 8/2009 | Doll et al. | | 2011/0125177 A1 | 5/2011 | Yates et al. |
| 2009/0209946 A1 | 8/2009 | Swayze et al. | | 2011/0132963 A1 | 6/2011 | Giordano et al. |
| 2009/0218384 A1 | 9/2009 | Aranyi | | 2011/0132964 A1 | 6/2011 | Weisenburgh, II et al. |
| 2009/0242610 A1 | 10/2009 | Shelton, IV et al. | | 2011/0132965 A1 | 6/2011 | Moore et al. |
| 2009/0255974 A1 | 10/2009 | Viola | | 2011/0144430 A1 | 6/2011 | Spivey et al. |
| 2009/0255975 A1 | 10/2009 | Zemlok et al. | | 2011/0147433 A1 | 6/2011 | Shelton, IV et al. |
| 2009/0255976 A1 | 10/2009 | Marczyk et al. | | 2011/0147434 A1 | 6/2011 | Hueil et al. |
| 2009/0255977 A1 | 10/2009 | Zemlok | | 2011/0155781 A1 | 6/2011 | Swensgard et al. |
| 2009/0255978 A1 | 10/2009 | Viola et al. | | 2011/0155787 A1 | 6/2011 | Baxter, III et al. |
| 2009/0289096 A1 | 11/2009 | Shelton, IV et al. | | 2011/0163147 A1 | 7/2011 | Laurent et al. |
| 2010/0012704 A1 | 1/2010 | Tarinelli Racenet et al. | | 2011/0174861 A1 | 7/2011 | Shelton, IV et al. |
| 2010/0032470 A1 | 2/2010 | Hess et al. | | 2011/0174863 A1 | 7/2011 | Shelton, IV et al. |
| 2010/0049084 A1 | 2/2010 | Nock et al. | | 2011/0192882 A1 | 8/2011 | Hess et al. |
| 2010/0065605 A1 | 3/2010 | Shelton, IV et al. | | 2011/0210156 A1 | 9/2011 | Smith et al. |
| 2010/0069942 A1 | 3/2010 | Shelton, IV | | 2011/0226837 A1 | 9/2011 | Baxter, III et al. |
| 2010/0072252 A1 | 3/2010 | Baxter, III et al. | | 2011/0275901 A1 | 11/2011 | Shelton, IV |
| 2010/0072254 A1 | 3/2010 | Aranyi et al. | | 2011/0276083 A1 | 11/2011 | Shelton, IV et al. |
| 2010/0076474 A1 | 3/2010 | Yates et al. | | 2011/0288573 A1 | 11/2011 | Yates et al. |
| 2010/0076475 A1 | 3/2010 | Yates et al. | | 2011/0290851 A1 | 12/2011 | Shelton, IV |
| 2010/0089970 A1 | 4/2010 | Smith et al. | | 2011/0290853 A1 | 12/2011 | Shelton, IV et al. |
| 2010/0089972 A1 | 4/2010 | Marczyk | | 2011/0290854 A1 | 12/2011 | Timm et al. |
| 2010/0089974 A1 | 4/2010 | Shelton, IV | | 2011/0290855 A1 | 12/2011 | Moore et al. |
| 2010/0096435 A1 | 4/2010 | Fuchs et al. | | 2011/0290856 A1 | 12/2011 | Shelton, IV et al. |
| 2010/0108740 A1 | 5/2010 | Pastorelli et al. | | 2011/0295242 A1 | 12/2011 | Spivey et al. |
| 2010/0108741 A1 | 5/2010 | Hessler et al. | | 2011/0295269 A1 | 12/2011 | Swensgard et al. |
| 2010/0127042 A1 | 5/2010 | Shelton, IV | | 2011/0295270 A1 | 12/2011 | Giordano et al. |
| 2010/0133317 A1 | 6/2010 | Shelton, IV et al. | | 2011/0295295 A1 | 12/2011 | Shelton, IV et al. |
| 2010/0133318 A1 | 6/2010 | Boudreaux | | 2012/0024934 A1 | 2/2012 | Shelton, IV et al. |
| 2010/0163598 A1 | 7/2010 | Belzer | | 2012/0024935 A1 | 2/2012 | Shelton, IV et al. |
| 2010/0179382 A1 | 7/2010 | Shelton, IV et al. | | 2012/0024936 A1 | 2/2012 | Baxter, III et al. |
| 2010/0181364 A1 | 7/2010 | Shelton, IV et al. | | 2012/0029272 A1 | 2/2012 | Shelton, IV et al. |
| 2010/0193566 A1 | 8/2010 | Scheib et al. | | 2012/0029544 A1 | 2/2012 | Shelton, IV et al. |
| 2010/0193567 A1 | 8/2010 | Scheib et al. | | 2012/0029547 A1 | 2/2012 | Shelton, IV et al. |
| 2010/0193568 A1 | 8/2010 | Scheib et al. | | 2012/0061448 A1 | 3/2012 | Zingman |

| | | |
|---|---|---|
| 2012/0071711 A1 | 3/2012 | Shelton, IV et al. |
| 2012/0071866 A1 | 3/2012 | Kerr et al. |
| 2012/0074196 A1 | 3/2012 | Shelton, IV et al. |
| 2012/0074198 A1 | 3/2012 | Huitema et al. |
| 2012/0074200 A1 | 3/2012 | Schmid et al. |
| 2012/0074201 A1 | 3/2012 | Baxter, III et al. |
| 2012/0080332 A1 | 4/2012 | Shelton, IV et al. |
| 2012/0080333 A1 | 4/2012 | Woodard, Jr. et al. |
| 2012/0080334 A1 | 4/2012 | Shelton, IV et al. |
| 2012/0080335 A1 | 4/2012 | Shelton, IV et al. |
| 2012/0080336 A1 | 4/2012 | Shelton, IV et al. |
| 2012/0080337 A1 | 4/2012 | Shelton, IV et al. |
| 2012/0080338 A1 | 4/2012 | Shelton, IV et al. |
| 2012/0080339 A1 | 4/2012 | Shelton, IV et al. |
| 2012/0080340 A1 | 4/2012 | Shelton, IV et al. |
| 2012/0080344 A1 | 4/2012 | Shelton, IV |
| 2012/0080345 A1 | 4/2012 | Morgan et al. |
| 2012/0080475 A1 | 4/2012 | Smith et al. |
| 2012/0080477 A1 | 4/2012 | Leimbach et al. |
| 2012/0080478 A1 | 4/2012 | Morgan et al. |
| 2012/0080479 A1 | 4/2012 | Shelton, IV |
| 2012/0080480 A1 | 4/2012 | Woodard, Jr. et al. |
| 2012/0080481 A1 | 4/2012 | Widenhouse et al. |
| 2012/0080482 A1 | 4/2012 | Schall et al. |
| 2012/0080483 A1 | 4/2012 | Riestenberg et al. |
| 2012/0080484 A1 | 4/2012 | Morgan et al. |
| 2012/0080485 A1 | 4/2012 | Woodard, Jr. et al. |
| 2012/0080486 A1 | 4/2012 | Woodard, Jr. et al. |
| 2012/0080487 A1 | 4/2012 | Woodard, Jr. et al. |
| 2012/0080488 A1 | 4/2012 | Shelton, IV et al. |
| 2012/0080489 A1 | 4/2012 | Shelton, IV et al. |
| 2012/0080490 A1 | 4/2012 | Shelton, IV et al. |
| 2012/0080491 A1 | 4/2012 | Shelton, IV et al. |
| 2012/0080493 A1 | 4/2012 | Shelton, IV et al. |
| 2012/0080496 A1 | 4/2012 | Schall et al. |
| 2012/0080498 A1 | 4/2012 | Shelton, IV et al. |
| 2012/0080499 A1 | 4/2012 | Schall et al. |
| 2012/0080500 A1 | 4/2012 | Morgan et al. |
| 2012/0080501 A1 | 4/2012 | Morgan et al. |
| 2012/0080502 A1 | 4/2012 | Morgan et al. |
| 2012/0080503 A1 | 4/2012 | Woodard, Jr. et al. |
| 2012/0083833 A1 | 4/2012 | Shelton, IV et al. |
| 2012/0083834 A1 | 4/2012 | Shelton, IV et al. |
| 2012/0083835 A1 | 4/2012 | Shelton, IV et al. |
| 2012/0083836 A1 | 4/2012 | Shelton, IV et al. |
| 2012/0132450 A1 | 5/2012 | Timm et al. |
| 2012/0138660 A1 | 6/2012 | Shelton, IV |
| 2012/0160721 A1 | 6/2012 | Shelton, IV et al. |
| 2012/0175399 A1 | 7/2012 | Shelton et al. |
| 2012/0187179 A1 | 7/2012 | Gleiman |
| 2012/0199630 A1 | 8/2012 | Shelton, IV et al. |
| 2012/0199631 A1 | 8/2012 | Shelton, IV et al. |
| 2012/0199632 A1 | 8/2012 | Spivey et al. |
| 2012/0199633 A1 | 8/2012 | Shelton, IV et al. |
| 2012/0203247 A1 | 8/2012 | Shelton, IV et al. |
| 2012/0205421 A1 | 8/2012 | Shelton, IV |
| 2012/0211546 A1 | 8/2012 | Shelton, IV |
| 2012/0234890 A1 | 9/2012 | Aronhalt et al. |
| 2012/0234891 A1 | 9/2012 | Aronhalt et al. |
| 2012/0234892 A1 | 9/2012 | Aronhalt et al. |
| 2012/0234893 A1 | 9/2012 | Schuckmann et al. |
| 2012/0234895 A1 | 9/2012 | O'Connor et al. |
| 2012/0234896 A1 | 9/2012 | Ellerhorst et al. |
| 2012/0234897 A1 | 9/2012 | Shelton, IV et al. |
| 2012/0234898 A1 | 9/2012 | Shelton, IV et al. |
| 2012/0234899 A1 | 9/2012 | Scheib et al. |
| 2012/0234900 A1 | 9/2012 | Swayze |
| 2012/0238823 A1 | 9/2012 | Hagerty et al. |
| 2012/0238824 A1 | 9/2012 | Widenhouse et al. |
| 2012/0238826 A1 | 9/2012 | Yoo et al. |
| 2012/0238829 A1 | 9/2012 | Shelton, IV et al. |
| 2012/0239009 A1 | 9/2012 | Mollere et al. |
| 2012/0239010 A1 | 9/2012 | Shelton, IV et al. |
| 2012/0239012 A1 | 9/2012 | Laurent et al. |
| 2012/0239075 A1 | 9/2012 | Widenhouse et al. |
| 2012/0239082 A1 | 9/2012 | Shelton, IV et al. |
| 2012/0241491 A1 | 9/2012 | Aldridge et al. |
| 2012/0241492 A1 | 9/2012 | Shelton, IV et al. |
| 2012/0241493 A1 | 9/2012 | Baxter, III et al. |
| 2012/0241496 A1 | 9/2012 | Vasudevan et al. |
| 2012/0241497 A1 | 9/2012 | Vasudevan et al. |
| 2012/0241498 A1 | 9/2012 | Gonzalez et al. |
| 2012/0241499 A1 | 9/2012 | Baxter, III et al. |
| 2012/0241500 A1 | 9/2012 | Timmer et al. |
| 2012/0241501 A1 | 9/2012 | Swayze et al. |
| 2012/0241502 A1 | 9/2012 | Aldridge et al. |
| 2012/0241503 A1 | 9/2012 | Baxter, III et al. |
| 2012/0241505 A1 | 9/2012 | Alexander, III et al. |
| 2012/0248169 A1 | 10/2012 | Widenhouse et al. |
| 2012/0253298 A1 | 10/2012 | Henderson et al. |
| 2012/0265230 A1 | 10/2012 | Yates et al. |
| 2012/0273551 A1 | 11/2012 | Shelton, IV et al. |
| 2012/0283707 A1 | 11/2012 | Giordano et al. |
| 2012/0286019 A1 | 11/2012 | Hueil et al. |
| 2012/0292367 A1 | 11/2012 | Morgan et al. |
| 2012/0292370 A1 | 11/2012 | Hess et al. |
| 2012/0298719 A1 | 11/2012 | Shelton, IV et al. |

FOREIGN PATENT DOCUMENTS

| | | |
|---|---|---|
| CA | 2514274 A1 | 1/2006 |
| CN | 1634601 A | 7/2005 |
| CN | 1868411 A | 11/2006 |
| CN | 1915180 A | 2/2007 |
| CN | 101095621 A | 1/2008 |
| DE | 273689 C | 5/1914 |
| DE | 1775926 A | 1/1972 |
| DE | 3036217 A1 | 4/1982 |
| DE | 3210466 A1 | 9/1983 |
| DE | 9412228 U | 9/1994 |
| DE | 19509116 A1 | 9/1996 |
| DE | 19851291 A1 | 1/2000 |
| DE | 19924311 A1 | 11/2000 |
| DE | 69328576 T2 | 1/2001 |
| DE | 10052679 A1 | 5/2001 |
| DE | 20112837 U1 | 10/2001 |
| DE | 20121753 U1 | 4/2003 |
| DE | 10314072 A1 | 1/2006 |
| DE | 202007003114 U1 | 6/2007 |
| EP | 0122046 A1 | 10/1984 |
| EP | 0070230 B1 | 10/1985 |
| EP | 0156774 A2 | 10/1985 |
| EP | 0387980 B1 | 10/1985 |
| EP | 0033548 B1 | 5/1986 |
| EP | 0129442 B1 | 11/1987 |
| EP | 0276104 A2 | 7/1988 |
| EP | 0178941 B1 | 1/1991 |
| EP | 0248844 B1 | 1/1993 |
| EP | 0545029 A1 | 6/1993 |
| EP | 0277959 B1 | 10/1993 |
| EP | 0233940 B1 | 11/1993 |
| EP | 0261230 B1 | 11/1993 |
| EP | 0639349 A2 | 2/1994 |
| EP | 0324636 B1 | 3/1994 |
| EP | 0593920 A1 | 4/1994 |
| EP | 0594148 A1 | 4/1994 |
| EP | 0427949 B1 | 6/1994 |
| EP | 0523174 B1 | 6/1994 |
| EP | 0600182 A2 | 6/1994 |
| EP | 0310431 B1 | 11/1994 |
| EP | 0375302 B1 | 11/1994 |
| EP | 0376562 B1 | 11/1994 |
| EP | 0630612 A1 | 12/1994 |
| EP | 0634144 A1 | 1/1995 |
| EP | 0646356 A2 | 4/1995 |
| EP | 0646357 A1 | 4/1995 |
| EP | 0653189 A2 | 5/1995 |
| EP | 0669104 A1 | 8/1995 |
| EP | 0511470 B1 | 10/1995 |
| EP | 0679367 A2 | 11/1995 |
| EP | 0392547 B1 | 12/1995 |
| EP | 0685204 A1 | 12/1995 |
| EP | 0364216 B1 | 1/1996 |
| EP | 0699418 A1 | 3/1996 |
| EP | 0702937 A1 | 3/1996 |
| EP | 0705571 A1 | 4/1996 |
| EP | 0711611 A2 | 5/1996 |
| EP | 0484677 B2 | 6/1996 |
| EP | 0541987 B1 | 7/1996 |

| | | | | | | |
|---|---|---|---|---|---|---|
| EP | 0667119 | B1 | 7/1996 | EP | 1473819 A1 | 11/2004 |
| EP | 0708618 | B1 | 3/1997 | EP | 1477119 A1 | 11/2004 |
| EP | 0770355 | A1 | 5/1997 | EP | 1479345 A1 | 11/2004 |
| EP | 0503662 | B1 | 6/1997 | EP | 1479347 A1 | 11/2004 |
| EP | 0447121 | B1 | 7/1997 | EP | 1479348 A1 | 11/2004 |
| EP | 0625077 | B1 | 7/1997 | EP | 0754437 B2 | 12/2004 |
| EP | 0633749 | B1 | 8/1997 | EP | 1025807 B1 | 12/2004 |
| EP | 0710090 | B1 | 8/1997 | EP | 1001710 B1 | 1/2005 |
| EP | 0578425 | B1 | 9/1997 | EP | 1520521 A1 | 4/2005 |
| EP | 0625335 | B1 | 11/1997 | EP | 1520523 A1 | 4/2005 |
| EP | 0552423 | B1 | 1/1998 | EP | 1520525 A1 | 4/2005 |
| EP | 0592244 | B1 | 1/1998 | EP | 1522264 A1 | 4/2005 |
| EP | 0648476 | B1 | 1/1998 | EP | 1523942 A2 | 4/2005 |
| EP | 0649290 | B1 | 3/1998 | EP | 1550408 A1 | 7/2005 |
| EP | 0598618 | B1 | 9/1998 | EP | 1557129 A1 | 7/2005 |
| EP | 0676173 | B1 | 9/1998 | EP | 1064883 B1 | 8/2005 |
| EP | 0678007 | B1 | 9/1998 | EP | 1067876 B1 | 8/2005 |
| EP | 0603472 | B1 | 11/1998 | EP | 0870473 B1 | 9/2005 |
| EP | 0605351 | B1 | 11/1998 | EP | 1157666 B1 | 9/2005 |
| EP | 0878169 | A1 | 11/1998 | EP | 0880338 B1 | 10/2005 |
| EP | 0879742 | A1 | 11/1998 | EP | 1158917 B1 | 11/2005 |
| EP | 0695144 | B1 | 12/1998 | EP | 1344498 B1 | 11/2005 |
| EP | 0722296 | B1 | 12/1998 | EP | 1330989 B1 | 12/2005 |
| EP | 0760230 | B1 | 2/1999 | EP | 0771176 B2 | 1/2006 |
| EP | 0623316 | B1 | 3/1999 | EP | 1621138 A2 | 2/2006 |
| EP | 0650701 | B1 | 3/1999 | EP | 1621139 A2 | 2/2006 |
| EP | 0537572 | B1 | 6/1999 | EP | 1621141 A2 | 2/2006 |
| EP | 0923907 | A1 | 6/1999 | EP | 1621145 A2 | 2/2006 |
| EP | 0843906 | B1 | 3/2000 | EP | 1621151 A2 | 2/2006 |
| EP | 0552050 | B1 | 5/2000 | EP | 1034746 B1 | 3/2006 |
| EP | 0833592 | B1 | 5/2000 | EP | 1632191 A2 | 3/2006 |
| EP | 0830094 | B1 | 9/2000 | EP | 1065981 B1 | 5/2006 |
| EP | 1034747 | A1 | 9/2000 | EP | 1082944 B1 | 5/2006 |
| EP | 1034748 | A1 | 9/2000 | EP | 1652481 A2 | 5/2006 |
| EP | 0694290 | B1 | 11/2000 | EP | 1382303 B1 | 6/2006 |
| EP | 1050278 | A1 | 11/2000 | EP | 1253866 B1 | 7/2006 |
| EP | 1053719 | A1 | 11/2000 | EP | 1032318 B1 | 8/2006 |
| EP | 1053720 | A1 | 11/2000 | EP | 1045672 B1 | 8/2006 |
| EP | 1055399 | A1 | 11/2000 | EP | 1617768 B1 | 8/2006 |
| EP | 1055400 | A1 | 11/2000 | EP | 1693015 A2 | 8/2006 |
| EP | 1080694 | A1 | 3/2001 | EP | 1400214 B1 | 9/2006 |
| EP | 1090592 | A1 | 4/2001 | EP | 1702567 A2 | 9/2006 |
| EP | 1095627 | A1 | 5/2001 | EP | 1129665 B1 | 11/2006 |
| EP | 1256318 | B1 | 5/2001 | EP | 1400206 B1 | 11/2006 |
| EP | 0806914 | B1 | 9/2001 | EP | 1721568 A1 | 11/2006 |
| EP | 0768840 | B1 | 12/2001 | EP | 1256317 B1 | 12/2006 |
| EP | 0908152 | B1 | 1/2002 | EP | 1285633 B1 | 12/2006 |
| EP | 0872213 | B1 | 5/2002 | EP | 1728473 A1 | 12/2006 |
| EP | 0862386 | B1 | 6/2002 | EP | 1728475 A2 | 12/2006 |
| EP | 0949886 | B1 | 9/2002 | EP | 1479346 B1 | 1/2007 |
| EP | 1238634 | A2 | 9/2002 | EP | 1484024 B1 | 1/2007 |
| EP | 0858295 | B1 | 12/2002 | EP | 1754445 A2 | 2/2007 |
| EP | 0656188 | B1 | 1/2003 | EP | 1759812 A1 | 3/2007 |
| EP | 1284120 | A1 | 2/2003 | EP | 1767163 A1 | 3/2007 |
| EP | 1287788 | A1 | 3/2003 | EP | 1769756 A1 | 4/2007 |
| EP | 0717966 | B1 | 4/2003 | EP | 1769758 A1 | 4/2007 |
| EP | 0869742 | B1 | 5/2003 | EP | 1581128 A1 | 5/2007 |
| EP | 0829235 | B1 | 6/2003 | EP | 1785097 A2 | 5/2007 |
| EP | 0887046 | B1 | 7/2003 | EP | 1790293 A2 | 5/2007 |
| EP | 0852480 | B1 | 8/2003 | EP | 1800610 A1 | 6/2007 |
| EP | 0891154 | B1 | 9/2003 | EP | 1300117 B1 | 8/2007 |
| EP | 0813843 | B1 | 10/2003 | EP | 1813199 A1 | 8/2007 |
| EP | 0873089 | B1 | 10/2003 | EP | 1813201 A1 | 8/2007 |
| EP | 0856326 | B1 | 11/2003 | EP | 1813203 A2 | 8/2007 |
| EP | 1374788 | A1 | 1/2004 | EP | 1813207 A1 | 8/2007 |
| EP | 0741996 | B1 | 2/2004 | EP | 1813209 A1 | 8/2007 |
| EP | 0814712 | B1 | 2/2004 | EP | 1487359 B1 | 10/2007 |
| EP | 1402837 | A1 | 3/2004 | EP | 1599146 B1 | 10/2007 |
| EP | 0705570 | B1 | 4/2004 | EP | 1839596 A1 | 10/2007 |
| EP | 0959784 | B1 | 4/2004 | EP | 2110083 A2 | 10/2007 |
| EP | 1407719 | A2 | 4/2004 | EP | 1857057 A2 | 11/2007 |
| EP | 1086713 | B1 | 5/2004 | EP | 1402821 B1 | 12/2007 |
| EP | 0996378 | B1 | 6/2004 | EP | 1872727 A1 | 1/2008 |
| EP | 1426012 | A1 | 6/2004 | EP | 1897502 A1 | 3/2008 |
| EP | 0833593 | B2 | 7/2004 | EP | 1330201 B1 | 6/2008 |
| EP | 1442694 | A1 | 8/2004 | EP | 1702568 B1 | 7/2008 |
| EP | 0888749 | B1 | 9/2004 | EP | 1943957 A2 | 7/2008 |
| EP | 0959786 | B1 | 9/2004 | EP | 1943964 A1 | 7/2008 |
| EP | 1459695 | A1 | 9/2004 | EP | 1943976 A2 | 7/2008 |

| | | | | | | |
|---|---|---|---|---|---|---|
| EP | 1593337 | B1 | 8/2008 | JP | 2006-281405 A | 10/2006 |
| EP | 1970014 | A1 | 9/2008 | RU | 2008830 C1 | 3/1994 |
| EP | 1980213 | A2 | 10/2008 | RU | 2187249 C2 | 8/2002 |
| EP | 1759645 | B1 | 11/2008 | RU | 2225170 C2 | 3/2004 |
| EP | 1990014 | A2 | 11/2008 | SU | 189517 A | 1/1967 |
| EP | 1693008 | B1 | 12/2008 | SU | 328636 A | 9/1972 |
| EP | 1759640 | B1 | 12/2008 | SU | 886900 A | 12/1981 |
| EP | 2000102 | A2 | 12/2008 | SU | 1009439 A | 4/1983 |
| EP | 2008595 | A2 | 12/2008 | SU | 1333319 A2 | 8/1987 |
| EP | 1736104 | B1 | 3/2009 | SU | 1377053 A1 | 2/1988 |
| EP | 1749486 | B1 | 3/2009 | SU | 1561964 A1 | 5/1990 |
| EP | 2039316 | A2 | 3/2009 | SU | 1722476 A1 | 3/1992 |
| EP | 1721576 | B1 | 4/2009 | WO | WO 82/02824 A1 | 9/1982 |
| EP | 1733686 | B1 | 4/2009 | WO | WO 91/15157 A1 | 10/1991 |
| EP | 2044890 | A1 | 4/2009 | WO | WO 92/20295 A1 | 11/1992 |
| EP | 1550413 | B1 | 6/2009 | WO | WO 92/21300 A1 | 12/1992 |
| EP | 1745748 | B1 | 8/2009 | WO | WO 93/08755 A1 | 5/1993 |
| EP | 2090237 | A1 | 8/2009 | WO | WO 93/13718 A1 | 7/1993 |
| EP | 2090244 | A2 | 8/2009 | WO | WO 93/14690 A1 | 8/1993 |
| EP | 2090256 | A2 | 8/2009 | WO | WO 93/15648 A1 | 8/1993 |
| EP | 2095777 | A2 | 9/2009 | WO | WO 93/15850 A1 | 8/1993 |
| EP | 2110082 | A1 | 10/2009 | WO | WO 93/19681 A1 | 10/1993 |
| EP | 1813208 | B1 | 11/2009 | WO | WO 94/00060 A1 | 1/1994 |
| EP | 2116195 | A1 | 11/2009 | WO | WO 94/11057 A1 | 5/1994 |
| EP | 1607050 | B1 | 12/2009 | WO | WO 94/12108 A1 | 6/1994 |
| EP | 1815804 | B1 | 12/2009 | WO | WO 94/18893 A1 | 9/1994 |
| EP | 1566150 | B1 | 4/2010 | WO | WO 94/22378 A1 | 10/1994 |
| EP | 1813206 | B1 | 4/2010 | WO | WO 94/23659 A1 | 10/1994 |
| EP | 1769754 | B1 | 6/2010 | WO | WO 95/02369 A1 | 1/1995 |
| EP | 1535565 | B1 | 10/2010 | WO | WO 95/03743 A1 | 2/1995 |
| EP | 1702570 | B1 | 10/2010 | WO | WO 95/06817 A1 | 3/1995 |
| EP | 1785098 | B1 | 10/2010 | WO | WO 95/09576 A1 | 4/1995 |
| EP | 2030578 | B1 | 11/2010 | WO | WO 95/09577 A1 | 4/1995 |
| EP | 1627605 | B1 | 12/2010 | WO | WO 95/14436 A1 | 6/1995 |
| EP | 1813205 | B1 | 6/2011 | WO | WO 95/17855 A1 | 7/1995 |
| EP | 1785102 | B1 | 1/2012 | WO | WO 95/18383 A1 | 7/1995 |
| FR | 999646 | A | 2/1952 | WO | WO 95/18572 A1 | 7/1995 |
| FR | 1112936 | A | 3/1956 | WO | WO 95/19739 A1 | 7/1995 |
| FR | 2598905 | A1 | 11/1987 | WO | WO 95/20360 A1 | 8/1995 |
| FR | 2765794 | A | 1/1999 | WO | WO 95/23557 A1 | 9/1995 |
| GB | 939929 | A | 10/1963 | WO | WO 95/24865 A1 | 9/1995 |
| GB | 1210522 | A | 10/1970 | WO | WO 95/25471 A3 | 9/1995 |
| GB | 1217159 | A | 12/1970 | WO | WO 95/26562 A1 | 10/1995 |
| GB | 1339394 | A | 12/1973 | WO | WO 95/29639 A1 | 11/1995 |
| GB | 2109241 | A | 6/1983 | WO | WO 96/04858 A1 | 2/1996 |
| GB | 2272159 | A | 5/1994 | WO | WO 96/19151 A1 | 6/1996 |
| GB | 2284242 | A | 5/1995 | WO | WO 96/19152 A1 | 6/1996 |
| GB | 2336214 | A | 10/1999 | WO | WO 96/20652 A1 | 7/1996 |
| GB | 2425903 | A | 11/2006 | WO | WO 96/21119 A1 | 7/1996 |
| JP | 58500053 | A | 1/1983 | WO | WO 96/22055 A1 | 7/1996 |
| JP | 61-98249 | A | 5/1986 | WO | WO 96/23448 A1 | 8/1996 |
| JP | 63-203149 | | 8/1988 | WO | WO 96/24301 A1 | 8/1996 |
| JP | 3-12126 | A | 1/1991 | WO | WO 96/27337 A1 | 9/1996 |
| JP | 5-212039 | A | 8/1993 | WO | WO 96/31155 A1 | 10/1996 |
| JP | 6007357 | A | 1/1994 | WO | WO 96/35464 A1 | 11/1996 |
| JP | 7051273 | A | 2/1995 | WO | WO 96/39085 A1 | 12/1996 |
| JP | 8033641 | A | 2/1996 | WO | WO 96/39086 A1 | 12/1996 |
| JP | 8229050 | A | 9/1996 | WO | WO 96/39087 A1 | 12/1996 |
| JP | 2000033071 | A | 2/2000 | WO | WO 96/39088 A1 | 12/1996 |
| JP | 2000171730 | A | 6/2000 | WO | WO 96/39089 A1 | 12/1996 |
| JP | 2000287987 | A | 10/2000 | WO | WO 97/00646 A1 | 1/1997 |
| JP | 2000325303 | A | 11/2000 | WO | WO 97/00647 A1 | 1/1997 |
| JP | 2001-514541 | A | 9/2001 | WO | WO 97/06582 A1 | 2/1997 |
| JP | 2001286477 | A | 10/2001 | WO | WO 97/10763 A1 | 3/1997 |
| JP | 2002143078 | A | 5/2002 | WO | WO 97/10764 A1 | 3/1997 |
| JP | 2002369820 | A | 12/2002 | WO | WO 97/11648 A2 | 4/1997 |
| JP | 2004-344663 | | 12/2004 | WO | WO 97/11649 A1 | 4/1997 |
| JP | 2005-028149 | A | 2/2005 | WO | WO 97/15237 A1 | 5/1997 |
| JP | 2005505322 | T | 2/2005 | WO | WO 97/24073 A1 | 7/1997 |
| JP | 2005103293 | A | 4/2005 | WO | WO 97/24993 A1 | 7/1997 |
| JP | 2005131163 | A | 5/2005 | WO | WO 97/30644 A1 | 8/1997 |
| JP | 2005131164 | A | 5/2005 | WO | WO 97/34533 A1 | 9/1997 |
| JP | 2005131173 | A | 5/2005 | WO | WO 97/37598 A1 | 10/1997 |
| JP | 2005131211 | A | 5/2005 | WO | WO 97/39688 A2 | 10/1997 |
| JP | 2005131212 | A | 5/2005 | WO | WO 98/17180 A1 | 4/1998 |
| JP | 2005137423 | A | 6/2005 | WO | WO 98/27880 A1 | 7/1998 |
| JP | 2005152416 | A | 6/2005 | WO | WO 98/30153 A1 | 7/1998 |
| JP | 2005-523105 | A | 8/2005 | WO | WO 98/47436 A1 | 10/1998 |
| JP | 2005524474 | A | 8/2005 | WO | WO 99/03407 A1 | 1/1999 |

| | | | |
|---|---|---|---|
| WO | WO 99/03408 A1 | 1/1999 |
| WO | WO 99/03409 A1 | 1/1999 |
| WO | WO 99/12483 A1 | 3/1999 |
| WO | WO 99/12487 A1 | 3/1999 |
| WO | WO 99/12488 A1 | 3/1999 |
| WO | WO 99/15086 A1 | 4/1999 |
| WO | WO 99/15091 A1 | 4/1999 |
| WO | WO 99/23933 A2 | 5/1999 |
| WO | WO 99/23959 A1 | 5/1999 |
| WO | WO 99/25261 A1 | 5/1999 |
| WO | WO 99/29244 A1 | 6/1999 |
| WO | WO 99/34744 A1 | 7/1999 |
| WO | WO 99/45849 A1 | 9/1999 |
| WO | WO 99/48430 A1 | 9/1999 |
| WO | WO 99/51158 A1 | 10/1999 |
| WO | WO 00/24322 A1 | 5/2000 |
| WO | WO 00/24330 A1 | 5/2000 |
| WO | WO 00/41638 A1 | 7/2000 |
| WO | WO 00/48506 A1 | 8/2000 |
| WO | WO 00/53112 A2 | 9/2000 |
| WO | WO 00/54653 A1 | 9/2000 |
| WO | WO 00/57796 A1 | 10/2000 |
| WO | WO 00/64365 A1 | 11/2000 |
| WO | WO 00/72762 A1 | 12/2000 |
| WO | WO 00/72765 A1 | 12/2000 |
| WO | WO 01/03587 A1 | 1/2001 |
| WO | WO 01/05702 A1 | 1/2001 |
| WO | WO 01/010482 A1 | 2/2001 |
| WO | WO 01/35845 A1 | 5/2001 |
| WO | WO 01/54594 A1 | 8/2001 |
| WO | WO 01/58371 A1 | 8/2001 |
| WO | WO 01/62158 A2 | 8/2001 |
| WO | WO 01/62161 A1 | 8/2001 |
| WO | WO 01/62162 A1 | 8/2001 |
| WO | WO 01/62164 A2 | 8/2001 |
| WO | WO 01/62169 A2 | 8/2001 |
| WO | WO 01/78605 A2 | 10/2001 |
| WO | WO 01/91646 A1 | 12/2001 |
| WO | WO 02/07608 A2 | 1/2002 |
| WO | WO 02/07618 A1 | 1/2002 |
| WO | WO 02/17799 A1 | 3/2002 |
| WO | WO 02/19920 A1 | 3/2002 |
| WO | WO 02/19932 A1 | 3/2002 |
| WO | WO 02/30297 A2 | 4/2002 |
| WO | WO 02/32322 A2 | 4/2002 |
| WO | WO 02/36028 A1 | 5/2002 |
| WO | WO 02/43571 A2 | 6/2002 |
| WO | WO 02/058568 A1 | 8/2002 |
| WO | WO 02/060328 A1 | 8/2002 |
| WO | WO 02/067785 A2 | 9/2002 |
| WO | WO 02/098302 A1 | 12/2002 |
| WO | WO 03/000138 A2 | 1/2003 |
| WO | WO 03/001329 A2 | 1/2003 |
| WO | WO 03/013363 A1 | 2/2003 |
| WO | WO 03/015604 A2 | 2/2003 |
| WO | WO 03/020106 A2 | 3/2003 |
| WO | WO 03/020139 A2 | 3/2003 |
| WO | WO 03/024339 A1 | 3/2003 |
| WO | WO 03/079909 A3 | 3/2003 |
| WO | WO 03/030743 A2 | 4/2003 |
| WO | WO 03/037193 A1 | 5/2003 |
| WO | WO 03/047436 A3 | 6/2003 |
| WO | WO 03/055402 A1 | 7/2003 |
| WO | WO 03/057048 A1 | 7/2003 |
| WO | WO 03/057058 A1 | 7/2003 |
| WO | WO 03/063694 A1 | 8/2003 |
| WO | WO 03/077769 A1 | 9/2003 |
| WO | WO 03/079911 A1 | 10/2003 |
| WO | WO 03/082126 A1 | 10/2003 |
| WO | WO 03/088845 A2 | 10/2003 |
| WO | WO 03/090630 A2 | 11/2003 |
| WO | WO 03/094743 A1 | 11/2003 |
| WO | WO 03/094745 A1 | 11/2003 |
| WO | WO 03/094746 A1 | 11/2003 |
| WO | WO 03/094747 A1 | 11/2003 |
| WO | WO 03/101313 A1 | 12/2003 |
| WO | WO 03/105698 A2 | 12/2003 |
| WO | WO 03/105702 A2 | 12/2003 |
| WO | WO 2004/006980 A2 | 1/2004 |
| WO | WO 2004/011037 A2 | 2/2004 |
| WO | WO 2004/019769 A1 | 3/2004 |
| WO | WO 2004/021868 A2 | 3/2004 |
| WO | WO 2004/028585 A2 | 4/2004 |
| WO | WO 2004/032754 A2 | 4/2004 |
| WO | WO 2004/032760 A2 | 4/2004 |
| WO | WO 2004/032762 A1 | 4/2004 |
| WO | WO 2004/032763 A2 | 4/2004 |
| WO | WO 2004/034875 A2 | 4/2004 |
| WO | WO 2004/047626 A1 | 6/2004 |
| WO | WO 2004/047653 A2 | 6/2004 |
| WO | WO 2004/049956 A2 | 6/2004 |
| WO | WO 2004/052426 A2 | 6/2004 |
| WO | WO 2004/056276 A1 | 7/2004 |
| WO | WO 2004/056277 A1 | 7/2004 |
| WO | WO 2004/062516 A1 | 7/2004 |
| WO | WO 2004/078050 A2 | 9/2004 |
| WO | WO 2004/078051 A2 | 9/2004 |
| WO | WO 2004/086987 A1 | 10/2004 |
| WO | WO 2004/096015 A2 | 11/2004 |
| WO | WO 2004/096057 A2 | 11/2004 |
| WO | WO 2004/103157 A2 | 12/2004 |
| WO | WO 2004/105593 A1 | 12/2004 |
| WO | WO 2004/105621 A1 | 12/2004 |
| WO | WO 2004/112618 A2 | 12/2004 |
| WO | WO 2004/112652 A2 | 12/2004 |
| WO | WO 2005/027983 A2 | 3/2005 |
| WO | WO 2005/037329 A2 | 4/2005 |
| WO | WO 2005/044078 A2 | 5/2005 |
| WO | WO 2005/055846 A1 | 6/2005 |
| WO | WO 2005/072634 A2 | 8/2005 |
| WO | WO 2005/078892 A1 | 8/2005 |
| WO | WO 2005/079675 A2 | 9/2005 |
| WO | WO 2005/096954 A2 | 10/2005 |
| WO | WO 2005/112806 A2 | 12/2005 |
| WO | WO 2005/112808 A1 | 12/2005 |
| WO | WO 2005/115251 A2 | 12/2005 |
| WO | WO 2005/115253 A2 | 12/2005 |
| WO | WO 2005/117735 A1 | 12/2005 |
| WO | WO 2005/122936 A1 | 12/2005 |
| WO | WO 2006/027014 A1 | 3/2006 |
| WO | WO 2006/044490 A2 | 4/2006 |
| WO | WO 2006/044581 A2 | 4/2006 |
| WO | WO 2006/044810 A2 | 4/2006 |
| WO | WO 2006/051252 A1 | 5/2006 |
| WO | WO 2006/059067 A1 | 6/2006 |
| WO | WO 2006/083748 A1 | 8/2006 |
| WO | WO 2006/092563 A1 | 9/2006 |
| WO | WO 2006/092565 A1 | 9/2006 |
| WO | WO 2006/115958 A1 | 11/2006 |
| WO | WO 2006/125940 A1 | 11/2006 |
| WO | WO 2006/132992 A1 | 12/2006 |
| WO | WO 2007/002180 A2 | 1/2007 |
| WO | WO 2007/016290 A2 | 2/2007 |
| WO | WO 2007/018898 A2 | 2/2007 |
| WO | WO 2007/098220 A2 | 8/2007 |
| WO | WO 2007/121579 A1 | 11/2007 |
| WO | WO 2007/131110 A1 | 11/2007 |
| WO | WO 2007/137304 A2 | 11/2007 |
| WO | WO 2007/139734 A2 | 12/2007 |
| WO | WO 2007/142625 A2 | 12/2007 |
| WO | WO 2007/147439 A1 | 12/2007 |
| WO | WO 2008/021969 A2 | 2/2008 |
| WO | WO 2008/039249 A1 | 4/2008 |
| WO | WO 2008/039270 A1 | 4/2008 |
| WO | WO 2008/045383 A2 | 4/2008 |
| WO | WO 2008/070763 A1 | 6/2008 |
| WO | WO 2008/089404 A2 | 7/2008 |
| WO | WO 2008/109125 A1 | 9/2008 |
| WO | WO 2010/063795 A1 | 6/2010 |
| WO | WO 2012/044844 A2 | 4/2012 |

OTHER PUBLICATIONS

C.C. Thompson et al., "Peroral Endoscopic Reduction of Dilated Gastrojejunal Anastomosis After Roux-en-Y Gastric Bypass: A Possible New Option for Patients with Weight Regain," Surg Endosc (2006) vol. 20, pp. 1744-1748.

B.R. Coolman, DVM, MS et al., "Comparison of Skin Staples With Sutures for Anastomosis of the Small Intestine in Dogs," Abstract; http://www.blackwell-synergy.com/doi/abs/10.1053/jvet.2000. 7539?cookieSet=1&journalCode=vsu which redirects to http://www3.interscience.wiley.com/journal/119040681/abstract?CRETRY=1&SRETRY=0; [online] accessed: Sep. 22, 2008 (2 pages).

The Sodem Aseptic Battery Transfer Kit, Sodem Systems, 2000, 3 pages.

"Biomedical Coatings," Fort Wayne Metals, Research Products Corporation, obtained online at www.fwmetals.com on Jun. 21, 2010 (1 page).

International Search Report for PCT/US2011/045313, dated Oct. 19, 2011 (3 pages).

Written Opinion for PCT/US2011/045313, dated Oct. 19, 2011 (6 pages).

International Preliminary Report on Patentability for PCT/US2010/022358, dated Aug. 9, 2011 (6 pages).

Van Meer et al., "A Disposable Plastic Compact Wrist for Smart Minimally Invasive Surgical Tools," LAAS/CNRS (Aug. 2005).

Breedveld et al., "A New, Easily Miniaturized Sterrable Endoscope," IEEE Engineering in Medicine and Biology Magazine (Nov./Dec. 2005).

D. Tuite, Ed., "Get the Lowdown on Ultracapacitors," Nov. 15, 2007; [online] URL: http://electronicdesign.com/Articles/Print.cfm?ArticleID=17465, accessed Jan. 15, 2008 (5 pages).

Datasheet for Panasonic TK Relays Ultra Low Profile 2 A Polarized Relay, Copyright Matsushita Electric Works, Ltd. (Known of at least as early as Aug. 17, 2010), 5 pages.

ASTM procedure D2240-00, "Standard Test Method for Rubber Property-Durometer Hardness," (Published Aug. 2000).

ASTM procedure D2240-05, "Standard Test Method for Rubber Property-Durometer Hardness," (Published Apr. 2010).

US 8,444,036 B2

MOTOR DRIVEN SURGICAL FASTENER DEVICE WITH MECHANISMS FOR ADJUSTING A TISSUE GAP WITHIN THE END EFFECTOR

CROSS REFERENCE TO RELATED APPLICATIONS

This non-provisional application is a continuation-in-part application of U.S. patent application Ser. No. 12/693,461, entitled "Driven Surgical Stapler Improvements", to Frederick E. Shelton, IV, filed on Jan. 26, 2010, now abandoned, which claims the benefit of U.S. Provisional Application Ser. No. 61/150,387 entitled "Motor-Driven Surgical Stapler Improvements" to Frederick E. Shelton, IV filed on Feb. 6, 2009, the entire disclosures of each being herein incorporated by reference in their respective entireties.

BACKGROUND

An example of a surgical stapler suitable for endoscopic applications is described in U.S. Pat. No. 5,465,895, which is hereby incorporated herein by reference in its entirety. Such device comprises an endocutter that has distinct closing and firing actions. Another example of a motor driven surgical stapler is disclosed U.S. Patent Application Publication No. US 2007/0175958 A1, entitled "Motor-Driven Surgical Cutting and Fastening Instrument With User Feedback System", published Aug. 2, 2007 which is hereby incorporated herein by reference in its entirety. Excerpts of such Publication are presented here to detail its base functions, improvements, background, and components. At the end, additional improvements to the system are disclosed.

U.S. Patent Application Publication No. US 2007/0175958 A1 provides in part that "[a] clinician using this device is able to close the jaw members upon tissue to position the tissue prior to firing. Once the clinician has determined that the jaw members are properly gripping tissue, the clinician can then fire the surgical stapler with a single firing stroke, or multiple firing strokes, depending on the device. Firing the surgical stapler causes severing and stapling the tissue. The simultaneous severing and stapling avoids complications that may arise when performing such actions sequentially with different surgical tools that respectively only sever and staple."

One specific advantage of being able to close upon tissue before firing is that the clinician is able to verify via an endoscope that the desired location for the cut has been achieved, including a sufficient amount of tissue has been captured between opposing jaws. Otherwise, opposing jaws may be drawn too close together, especially pinching at their distal ends, and thus not effectively forming closed staples in the severed tissue. At the other extreme, an excessive amount of clamped tissue may cause binding and an incomplete firing.

Endoscopic staplers/cutters continue to increase in complexity and function with each generation. One of the main reasons for this is the quest for lower force-to-fire (FTF) to a level that all or a great majority of surgeons can handle. One known solution to lower FTF is to use C02 or electrical motors. These devices have not faired much better than traditional hand-powered devices, but for a different reason. Surgeons typically prefer to experience proportionate force distribution to that being experienced by the end-effector in the forming the staple to assure them that the cutting/stapling cycle is complete, with the upper limit within the capabilities of most surgeons (usually around 15-30 lbs). They also typically want to maintain control of deploying the staple and being able to stop at anytime if the forces felt in the handle of the device feel too great or for some other clinical reason. These user-feedback effects are not suitably realizable in present motor-driven endocutters. As a result, there is a general lack of acceptance by physicians of motor-drive endocutters where the cutting/stapling operation is actuated by merely pressing a button.

The foregoing discussion is intended only to illustrate some of the shortcomings present in the field of the invention at the time, and should not be taken as a disavowal of claim scope.

SUMMARY

In accordance with a general aspect of the present invention, there is provided surgical fastener apparatus that has a handle and an elongated shaft. The elongated shaft has a proximal end that is attached to the handle. The elongated shaft further has a distal end that is coupled to an end effector that comprises a pair of jaws that are pivoted at a proximal end thereof and are movable between an open and closed position. A cartridge that contains a plurality of surgical fasteners is attached to the end effector. The apparatus further includes an electrically powered actuator for deploying the surgical fasteners. In various embodiments, the actuator comprises a power source and a motor. The apparatus further has means for electrically adjusting the amount of spacing between the jaws when the end effector is in the closed position.

In accordance with another general aspect of the present invention, there is provided a surgical fastener apparatus that has a handle that has an end effector operably coupled thereto. In various embodiments, the end effector comprises an elongated channel that is configured to support a cartridge therein. An anvil is movably supported on the elongated channel for selective movement toward the elongated channel to closed positions and away from said elongated channel to open positions. The anvil has an elongated slot therein. An actuator member is movably supported within the elongated channel and is selectively movable from an unactuated proximal position to actuated positions within the elongated channel. In various embodiments, the actuator member comprises a lower actuator portion that slidably engages the elongated channel and an upper actuator portion that is configured to protrude into the elongated slot. A retainer member protrudes from each lateral side of the upper actuator portion in a direction that is substantially transverse to the elongated slot in the anvil. Height adjustment members are provided on each retainer member to selectively adjust a spacing between the anvil and the elongated channel when the anvil is in one of the closed positions in response to electrical current applied thereto.

In accordance with another general aspect of the present invention, there is provided a surgical fastener apparatus that has a handle that has an end effector operably coupled thereto. In various embodiments, the end effector comprises an elongated channel that is configured to support a cartridge therein. An anvil is movably supported on the elongated channel for selective movement toward the elongated channel to closed positions and away from said elongated channel to open positions. The anvil has an elongated slot therein. An actuator member is movably supported within the elongated channel and is selectively movable from an unactuated proximal position to actuated positions within the elongated channel in response to drive motions applied thereto by a first electrically powered motor supported in the handle. In various embodiments, the actuator member comprises a lower actuator portion that slidably engages the elongated channel and an upper actuator portion that is configured to protrude into the elongated slot and is movable relative to the lower actuator portion. A retainer member protrudes from each lateral side of the upper actuator portion in a direction that is substantially transverse to the elongated slot in the anvil. A second electrically powered motor is coupled to the upper and lower actuator portions for selectively moving the upper actuator portion relative to the lower actuator portion.

In one general aspect, the present invention is directed to a motorized surgical cutting and fastening instrument that provides feedback to the user regarding the position, force and/or deployment of the end effector. The instrument, in various embodiments, also allows the operator to control the end effector, including being able to stop deployment if so desired. The instrument may include two triggers in its handle—a closure trigger and a firing trigger—with separate actuation motions. When an operator of the instrument retracts the closure trigger, tissue positioned in the end effector may be clamped by the end effector. Then, when the operator retracts the firing trigger, a motor may power, via a gear drive train, a rotational main drive shaft assembly, which causes a cutting instrument in the end effector to sever the clamped tissue.

In various embodiments, the instrument may comprise a power assist system with loading force feedback and control to reduce the firing force required to be exerted by the operator in order to complete the cutting operation. In such embodiments, the firing trigger may be geared into the gear drive train of the main drive shaft assembly. In that way, the operator may experience feedback regarding the force being applied to the cutting instrument. That is, the loading force on the firing trigger may be related to the loading force experienced by the cutting instrument. Also in such embodiments, because the firing trigger is geared into the gear drive train, force applied by the operator may be added to the force applied to the motor.

According to various embodiments, when the firing trigger is retracted an appropriate amount (e.g., five degrees), an on/off switch may be actuated, which sends a signal to the motor to rotate at a specified rate, thus commencing actuation of the drive shaft assembly and end effector. According to other embodiments, a proportional sensor may be used. The proportional sensor may send a signal to the motor to rotate at a rate proportional to the force applied to the firing trigger by the operator. In that way, the rotational position of the firing trigger is generally proportional to where the cutting instrument is in the end effector (e.g., fully deployed or fully retracted). Further, the operator could stop retracting the firing trigger at some point in the stroke to stop the motor, and thereby stop the cutting motion. In addition, sensors may be used to detect the beginning of the stroke of the end effector (e.g., fully retracted position) and the end of the stroke (e.g., fully deployed position), respectively. Consequently, the sensors may provide an adaptive control system for controlling end effector deployment that is outside of the closed loop system of the motor, gear drive train, and end effector.

In other embodiments, the firing trigger may not be directly geared into the gear drive train used to actuate the end effector. In such embodiments, a second motor may be used to apply forces to the firing trigger to simulate the deployment of the cutting instrument in the end effector. The second motor may be controlled based on incremental rotations of the main drive shaft assembly, which may be measured by a rotary encoder. In such embodiment, the position of the rotational position of the firing trigger may be related to the position of the cutting instrument in the end effector. Additionally, an on/off switch or a proportional switch may be used to control the main motor (i.e., the motor that powers the main drive shaft).

In various implementations, the end effector may use a helical drive screw in the base of the end effector to drive the cutting instrument (e.g., knife). Also, the end effector may include a staple cartridge for stapling the severed tissue. According to other embodiments, other means for fastening (or sealing) the severed tissue may be used, including RF energy and adhesives.

Also, the instrument may include a mechanical closure system. The mechanical closure system may include an elongate channel having a clamping member, such as an anvil, pivotably connected to the channel to clamp tissue positioned in the end effector. The user may activate the clamping action of the end effector by retracting the closer trigger, which, through a mechanical closure system, causes the clamping action of the end effector. Once the clamping member is locked in place, the operator may activate the cutting operation by retracting the separate firing trigger. This may cause the cutting instrument to travel longitudinally along the channel in order to cut tissue clamped by the end effector.

In various implementations, the instrument may include a rotational main drive shaft assembly for actuating the end effector. Further, the main drive shaft may comprise an articulating joint such that the end effector may be articulated. The articulation joint may comprise, for example, a bevel gear assembly, a universal joint, or a flexible torsion cable capable of transmitting torsion force to the end effector.

Other aspects of the present invention are directed to various mechanisms for locking the closure trigger to a lower, pistol-grip portion of the handle. Such embodiments free up space in the handle directly above and behind the triggers for other components of the instrument, including components of the gear drive train and the mechanical closure system."

The disclosure herein shows how one could embody a battery powered gear driven self-contained endoscopic stapling device.

BRIEF DESCRIPTION OF DRAWINGS

The above-mentioned and other features and advantages of this invention, and the manner of attaining them, will become more apparent and the invention itself will be better understood by reference to the following description of embodiments of the invention taken in conjunction with the accompanying drawings, wherein.

DETAILED DESCRIPTION OF THE INVENTION

Figure 1:
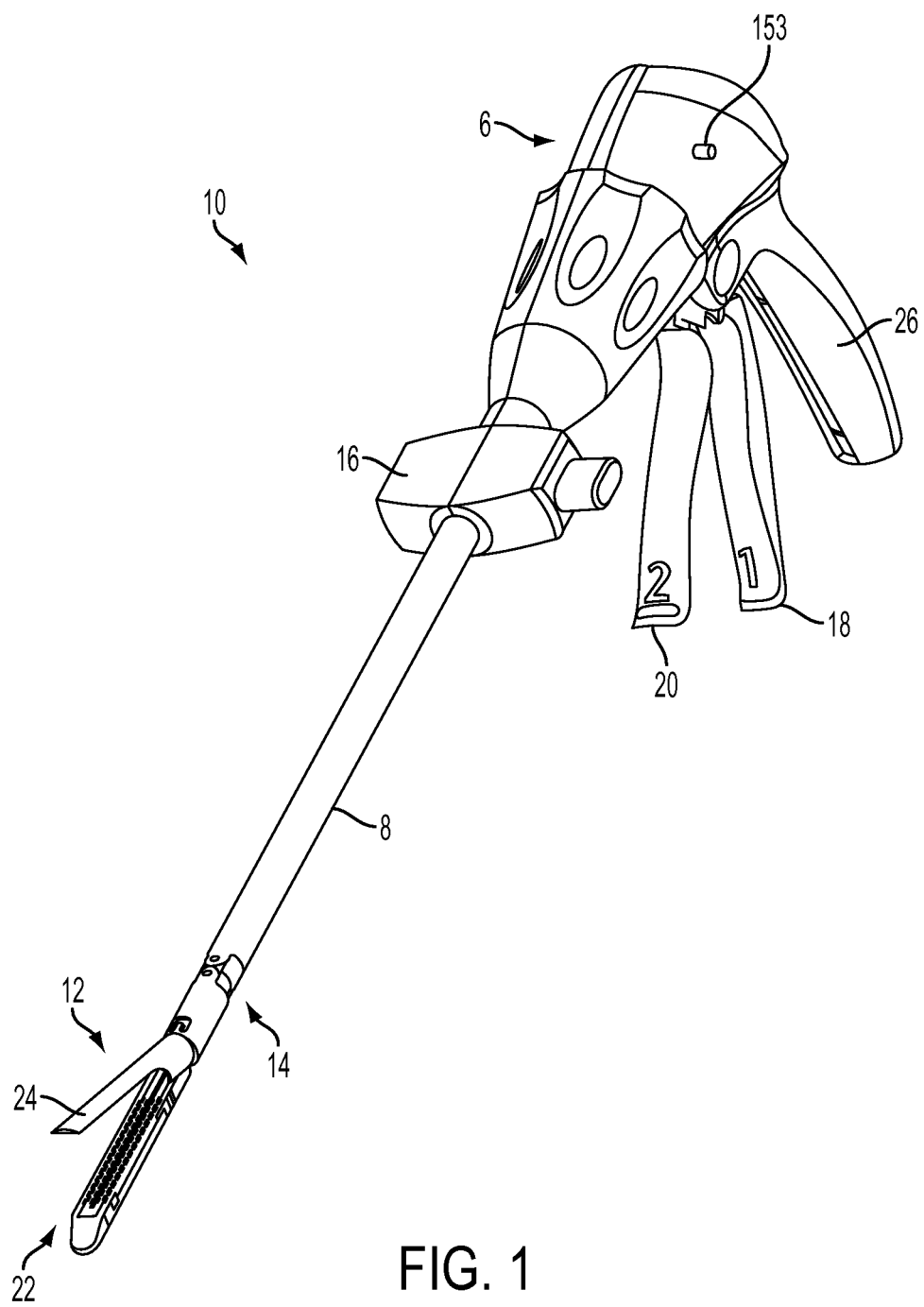
FIGS. 1 and 2 are perspective views of a surgical cutting and fastening instrument according to various embodiments of the present invention.

The owner of the subject application also owns the following U.S. patent applications that were filed on even date herewith and which are each herein incorporated by reference in their respective entirety:

U.S. patent application entitled "Motor Driven Surgical Fastener Device With Cutting Member Reversing Mechanism", U.S. patent application Ser. No. 12/846,249, U.S. Patent Application Publication No. US-2011-0006103-A1; and U.S. patent application entitled "Motor Driven Surgical Fastener Device With Cutting Member Lockout Arrangements, U.S. patent application Ser. No. 12/846,228, U.S. Patent Application Publication No. US-2011-0006101-A1.

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the various embodiments of the present invention is defined solely by the claims. The features illustrated or described in connection with one exemplary embodiment may be combined with the features of other embodiments. Such modifications and variations are intended to be included within the scope of the present invention.

Reference throughout the specification to "various embodiments," "some embodiments," "one embodiment," or "an embodiment", "an implementation" or "various implementations" or the like, means that a particular feature, structure, or characteristic described in connection with the embodiment is included in at least one embodiment. Thus, appearances of the phrases "in various embodiments," "in some embodiments," "in one embodiment", or "in an embodiment", "an implementation" or "various implementations" or the like, in places throughout the specification are not necessarily all referring to the same embodiment or implementation. Furthermore, the particular features, structures, or characteristics may be combined in any suitable manner in one or more embodiments or implementations. Thus, the particular features, structures, or characteristics illustrated or described in connection with one embodiment may be combined, in whole or in part, with the features structures, or characteristics of one or more other embodiments without limitation. Such modifications and variations are intended to be included within the scope of the present invention.

The terms "proximal" and "distal" are used herein with reference to a clinician manipulating the handle portion of the surgical instrument. The term "proximal" referring to the portion closest to the clinician and the term "distal" referring to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Figure 2:
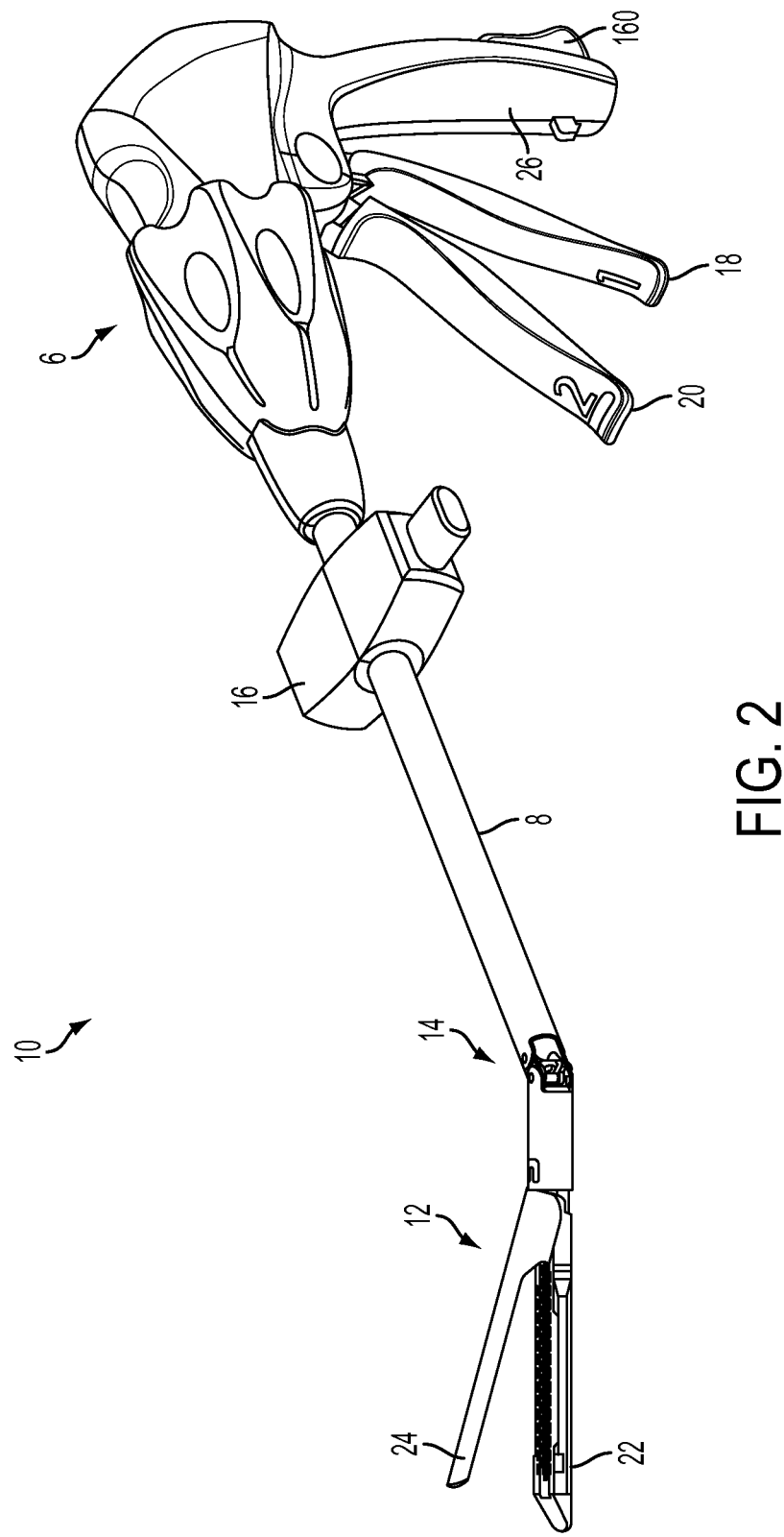

FIGS. 1 and 2 depict a surgical cutting and fastening instrument 10 according to various embodiments of the present invention. The illustrated embodiment is an endoscopic surgical instrument 10 and in general, the embodiments of the instrument 10 described herein are endoscopic surgical cutting and fastening instruments. It should be noted, however, that according to other embodiments of the present invention, the instrument 10 may be a non-endoscopic surgical cutting instrument, such as a laproscopic instrument.

The surgical instrument 10 depicted in FIGS. 1 and 2 comprises a handle 6, a shaft 8, and an articulating end effector 12 pivotally connected to the shaft 8 at an articulation pivot 14. An articulation control 16 may be provided adjacent to the handle 6 to effect rotation of the end effector 12 about the articulation pivot 14. It will be appreciated that various embodiments may include a non-pivoting end effector, and therefore may not have an articulation pivot 14 or articulation control 16. Also, in the illustrated embodiment, the end effector 12 is configured to act as an endocutter for clamping, severing and stapling tissue, although, in other embodiments, different types of end effectors may be used, such as end effectors for other types of surgical devices, such as graspers, cutters, staplers, clip appliers, access devices, drug/gene therapy devices, ultrasound, RF or laser devices, etc.

The handle 6 of the instrument 10 may include a closure trigger 18 and a firing trigger 20 for actuating the end effector 12. It will be appreciated that instruments having end effectors directed to different surgical tasks may have different numbers or types of triggers or other suitable controls for operating the end effector 12. The end effector 12 is shown separated from the handle 6 by a preferably elongate shaft 8. In one embodiment, a clinician or operator of the instrument 10 may articulate the end effector 12 relative to the shaft 8 by utilizing the articulation control 16, as described in more detail in U.S. Pat. No. 7,670,334, entitled "Surgical Instrument Having An Articulating End Effector," by Geoffrey C. Hueil et al., which is incorporated herein by reference in its entirety.

The end effector 12 includes in this example, among other things, an elongated channel 22 configured to operably support a staple cartridge 34 therein and a pivotally translatable clamping member, such as an anvil 24, which are maintained at a spacing that assures effective stapling and severing of tissue clamped in the end effector 12. The handle 6 includes a pistol grip 26 toward which a closure trigger 18 is pivotally drawn by the clinician to cause clamping or closing of the anvil 24 towards the elongated channel 22 of the end effector 12 to thereby clamp tissue positioned between the anvil 24 and elongated channel 22. The firing trigger 20 is farther outboard of the closure trigger 18. Once the closure trigger 18 is locked in the closure position as further described below, the firing trigger 20 may rotate slightly toward the pistol grip 26 so that it can be reached by the operator using one hand. Then the operator may pivotally draw the firing trigger 20 toward the pistol grip 26 to cause the stapling and severing of clamped tissue in the end effector 12. In other embodiments, different types of clamping members besides the anvil 24 could be used, such as, for example, an opposing jaw, etc.

The closure trigger 18 may be actuated first. Once the clinician is satisfied with the positioning of the end effector 12, the clinician may draw back the closure trigger 18 to its fully closed, locked position proximate to the pistol grip 26. The firing trigger 20 may then be actuated. The firing trigger 20 returns to the open position (shown in FIGS. 1 and 2) when the clinician removes pressure, as described more fully below. A release button on the handle 6, when depressed may release the locked closure trigger 18. The release button may be implemented in various forms such as, for example, slide release button 160 shown in FIG. 16, and/or button 172 shown in FIG. 17.

Figure 3:
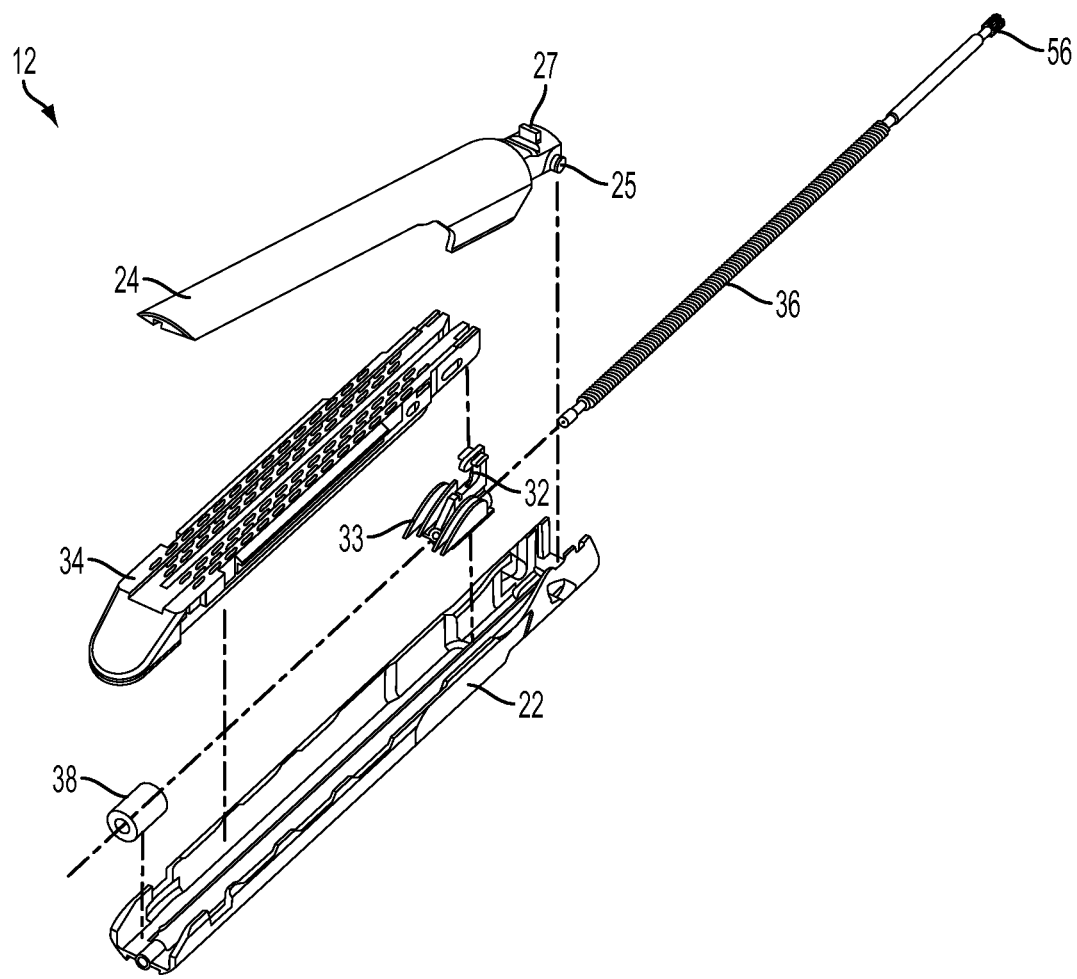
FIGS. 3-5 are exploded views of an end effector and shaft of the instrument according to various embodiments of the present invention.

FIGS. 3-6 show embodiments of a rotary-driven end effector 12 and shaft 8 according to various embodiments. FIG. 3 is an exploded view of the end effector 12 according to various embodiments. As shown in the illustrated embodiment, the end effector 12 may include, in addition to the previously-mentioned channel 22 and anvil 24, a cutting instrument 32, a sled 33, a staple cartridge 34 that is removably seated in the channel 22, and a helical screw shaft 36. The cutting instrument 32 may be, for example, a knife. As used herein with respect to at least one embodiment, the term "actuator" may refer to the knife and/or sled. The anvil 24 may be pivotally opened and closed at pivot pins 25 connected to the proximate end of the channel 22. The anvil 24 may also include a tab 27 at its proximate end that is inserted into a component of the mechanical closure system (described further below) to open and close the anvil 24. When the closure trigger 18 is actuated, that is, drawn in by a user of the instrument 10, the anvil 24 may pivot about the pivot pins 25 into the clamped or closed position. If clamping of the end effector 12 is satisfactory, the operator may actuate the firing trigger 20, which, as explained in more detail below, causes the knife 32 and sled 33 to travel longitudinally along the channel 22, thereby cutting tissue clamped within the end effector 12. The movement of the sled 33 along the channel 22 causes the staples (not shown) of the staple cartridge 34 to be driven through the severed tissue and against the closed anvil 24, which turns the staples to fasten the severed tissue. In various embodiments, the sled 33 may be an integral component of the cartridge 34. U.S. Pat. No. 6,978,921, entitled "Surgical Stapling Instrument Incorporating an E-beam Firing Mechanism" to Shelton, IV et al., which is incorporated herein by reference, provides more details about such two-stroke cutting and fastening instruments. The sled 33 may be part of the cartridge 34, such that when the knife 32 retracts following the cutting operation, the sled 33 does not retract.

Figure 4:
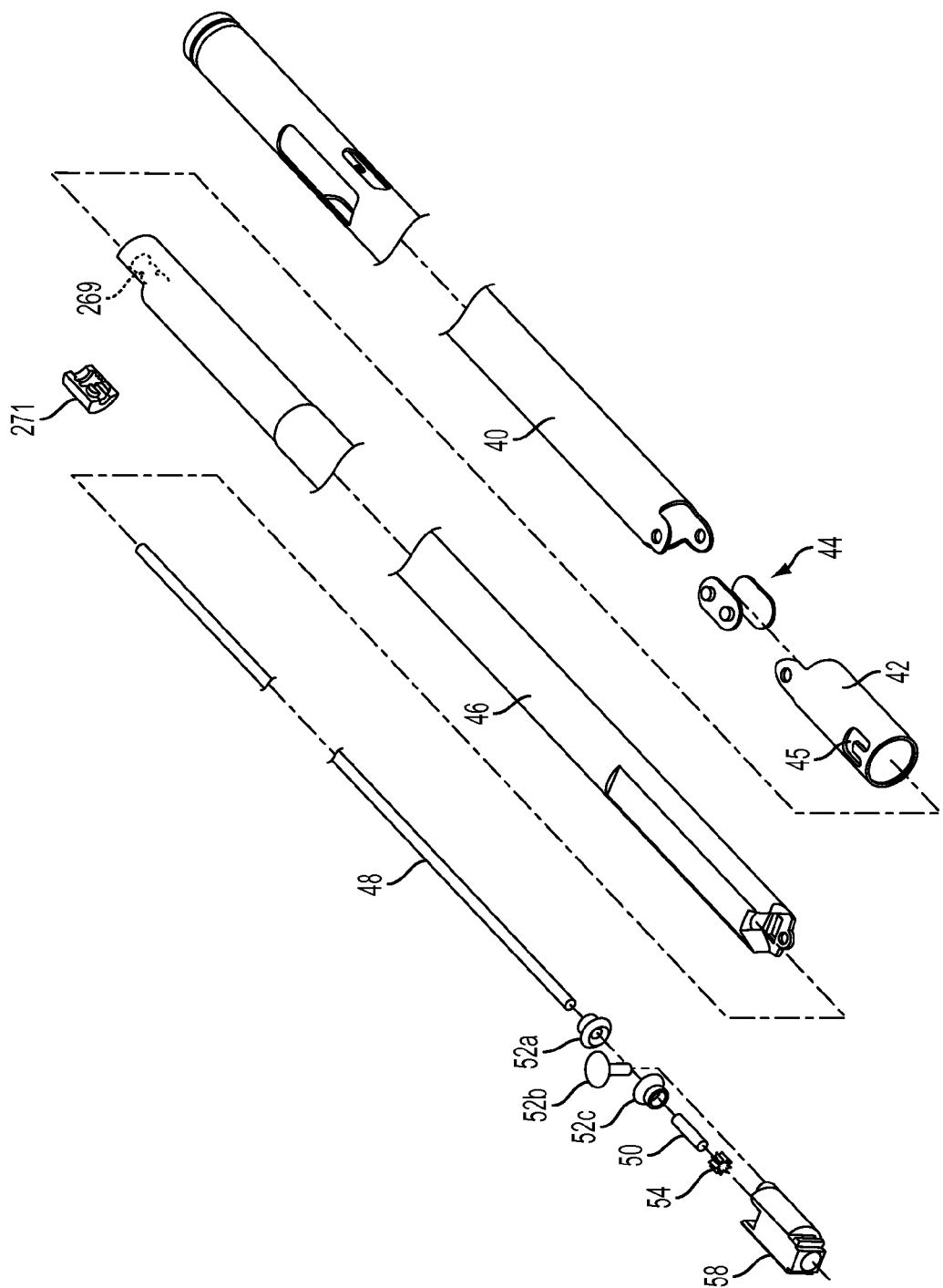
Figure 5:
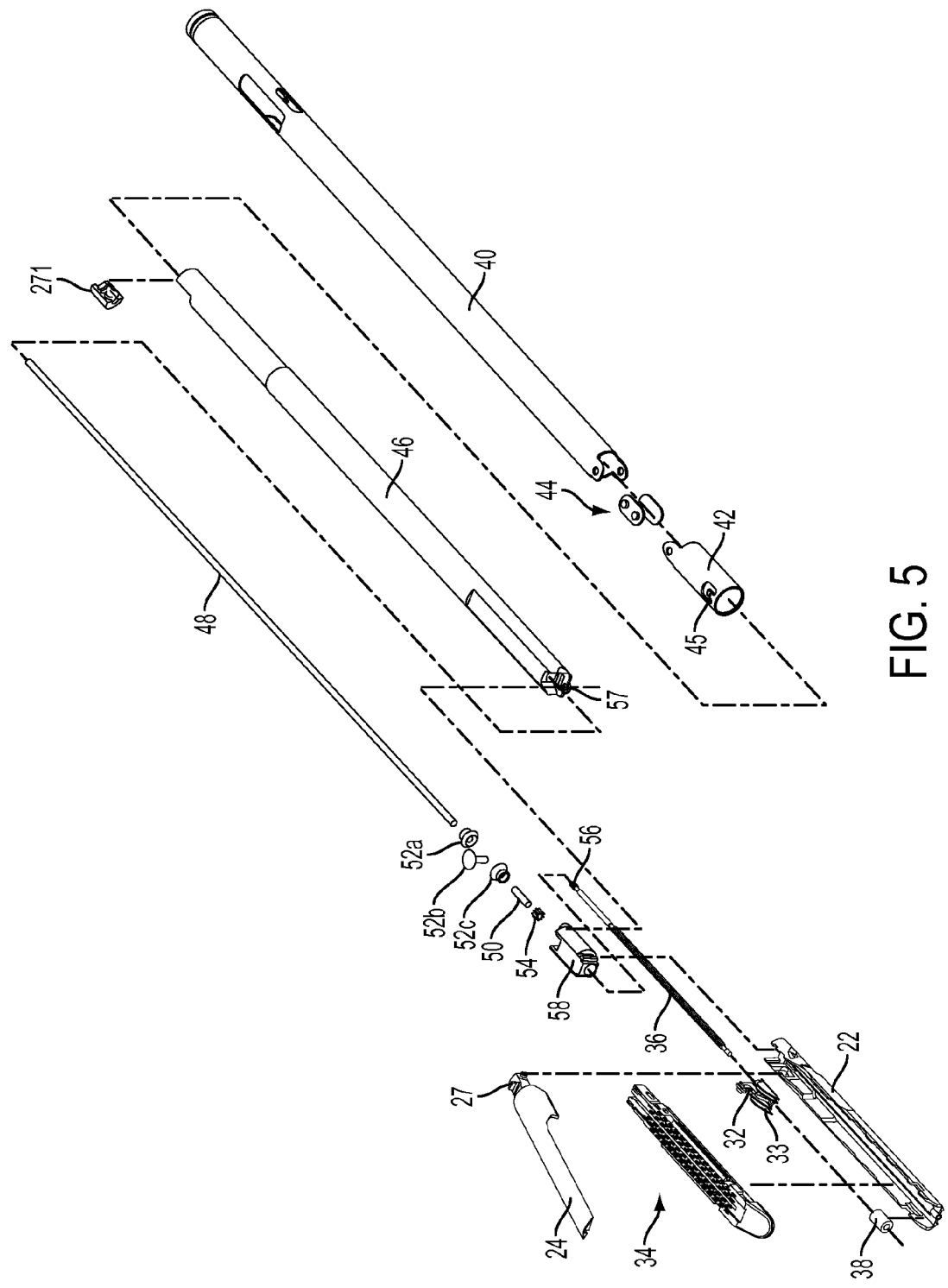
Figure 6:
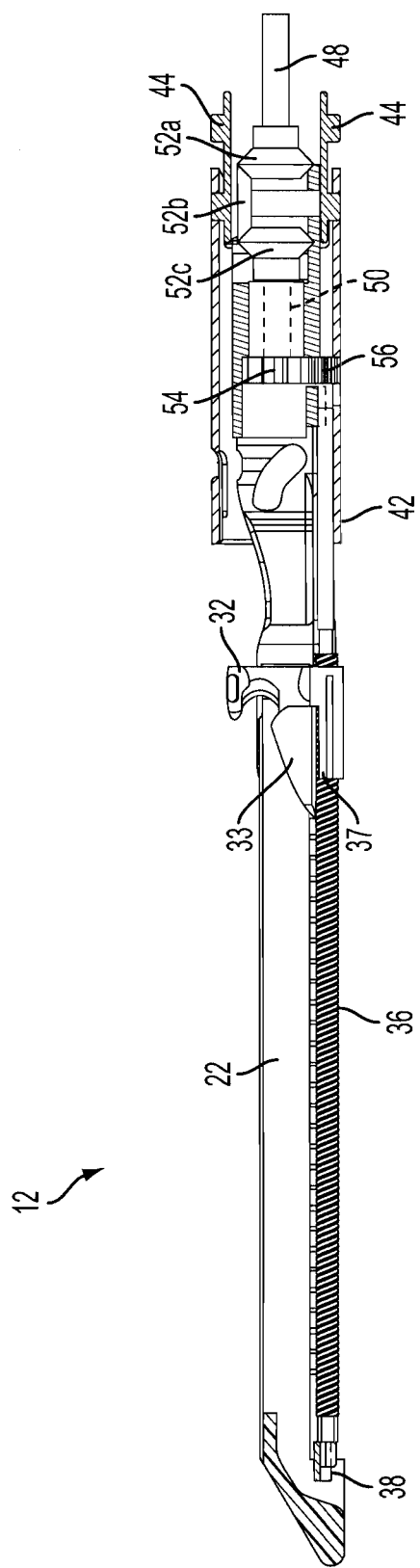
FIG. 6 is a side view of the end effector according to various embodiments of the present invention.
Figure 7:
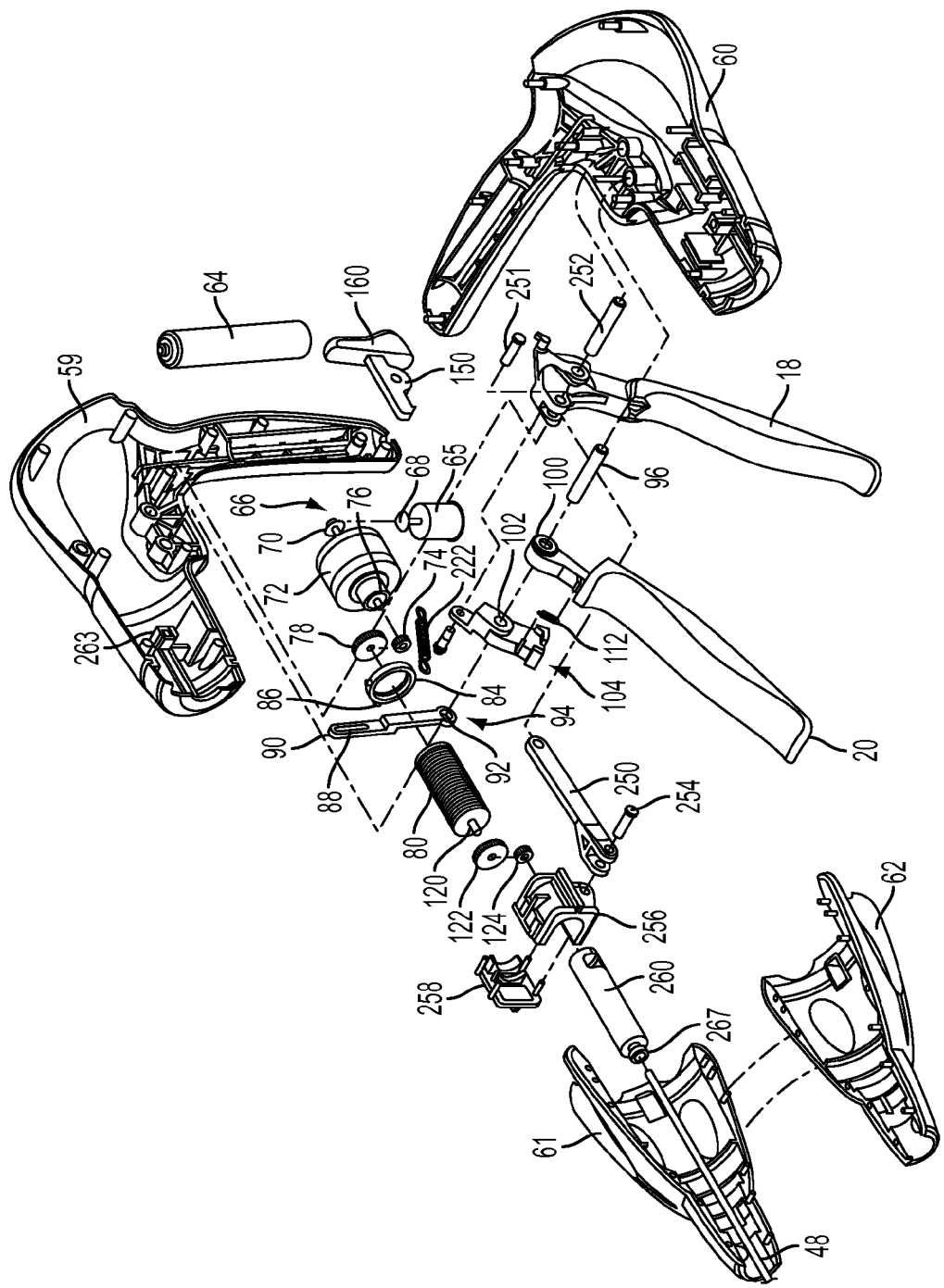
FIG. 7 is an exploded view of the handle of the instrument according to various embodiments of the present invention.

FIGS. 4 and 5 are exploded views and FIG. 6 is a side view of the end effector 12 and shaft 8 according to various embodiments. As shown in the illustrated embodiment, the shaft 8 may include a proximate closure tube 40 and a distal closure tube 42 pivotably linked by a pivot link 44. The distal closure tube 42 includes an opening 45 into which the tab 27 on the anvil 24 is inserted in order to open and close the anvil 24, as further described below. Disposed inside the closure tubes 40, 42 may be a proximate spine tube 46. Disposed inside the proximate spine tube 46 may be a main rotational (or proximate) drive shaft 48 that communicates with a secondary (or distal) drive shaft 50 via a bevel gear assembly 52. The secondary drive shaft 50 is connected to a drive gear 54 that engages a proximate drive gear 56 of the helical screw shaft 36. The vertical bevel gear 52b may sit and pivot in an opening 57 in the distal end of the proximate spine tube 46. A distal spine tube 58 may be used to enclose the secondary drive shaft 50 and the drive gears 54, 56. Collectively, the main drive shaft 48, the secondary drive shaft 50, and the articulation assembly (e.g., the bevel gear assembly 52a-c) are sometimes referred to herein as the "main drive shaft assembly."

A bearing 38, positioned at a distal end of the staple channel 22, receives the helical drive screw 36, allowing the helical drive screw 36 to freely rotate with respect to the channel 22. The helical screw shaft 36 may interface a threaded opening (not shown) of the knife 32 such that rotation of the shaft 36 causes the knife 32 to translate distally or proximately (depending on the direction of the rotation) through the staple channel 22. Accordingly, when the main drive shaft 48 is caused to rotate upon application of an actuation motion to the firing trigger 20 (as explained in more detail below), the bevel gear assembly 52a-c causes the secondary drive shaft 50 to rotate, which in turn, because of the engagement of the drive gears 54, 56, causes the helical screw shaft 36 to rotate, which causes the knife driving member 32 to travel longitudinally along the channel 22 to cut any tissue clamped within the end effector 12. The sled 33 may be made of, for example, plastic, and may have a sloped distal surface. As the sled 33 traverses the channel 22, the sloped forward surface may push up or drive the staples in the staple cartridge through the clamped tissue and against the anvil 24. The anvil 24 forms or turns the staples, thereby stapling the severed tissue. When the knife 32 is retracted, the knife 32 and sled 33 may become disengaged, thereby leaving the sled 33 at the distal end of the channel 22.

FIGS. 7-10 illustrate an exemplary embodiment of a motor-driven endocutter, and in particular the handle thereof, that provides user-feedback regarding the deployment and loading force of the cutting instrument 32 in the end effector 12. In addition, the embodiment may use power provided by the user in retracting the firing trigger 20 to power the device (a so-called "power assist" mode). The embodiment may be used with the rotary driven end effector 12 and shaft 8 embodiments described above. As shown in the illustrated embodiment, the handle 6 includes exterior lower side pieces 59, 60 and exterior upper side pieces 61, 62 that fit together to form, in general, the exterior of the handle 6. In various embodiments, the rotary driven end effector may be powered by a motor 65 that is disposed in an upper portion of the pistol grip portion 26 of the handle and powered by a power source 64. The power source 64 may comprise a battery or a supply of alternating current. In a preferred embodiment, the power source 64 comprises a Li ion battery that is supported in the pistol grip portion 26 of the handle 6. According to various embodiments, the motor 65 may be a DC brushed driving motor having a maximum rotation of, approximately, 5000 RPM. The motor 65 may drive a 90 degree bevel gear assembly 66 comprising a first bevel gear 68 and a second bevel gear 70. The bevel gear assembly 66 may drive a planetary gear assembly 72. The planetary gear assembly 72 may include a pinion gear 74 connected to a drive shaft 76. The pinion gear 74 may drive a mating ring gear 78 that drives a helical gear drum 80 via a drive shaft 82. A ring 84 may be threaded on the helical gear drum 80. Thus, when the motor 65 rotates, the ring 84 is caused to travel along the helical gear drum 80 by means of the interposed bevel gear assembly 66, planetary gear assembly 72 and ring gear 78.

The handle 6 may also include a run motor switch 110 (see FIG. 10) in communication with the firing trigger 20 to receive an actuation motion from the firing trigger 20 when the firing trigger has been drawn in (or "closed") toward the pistol grip portion 26 of the handle 6 by the operator to thereby actuate the cutting/stapling operation by the end effector 12. The run motor switch 110 may be a proportional sensor such as, for example, a rheostat or variable resistor. When the firing trigger 20 is drawn in, the run motor switch 110 permits current to flow from the power source 64 to the motor 65. When the run motor switch 110 is a variable resistor or the like, the rotation of the motor 65 may be generally proportional to the amount of movement of the firing trigger 20. That is, if the operator only draws or closes the firing trigger 20 in a small amount, the rotation of the motor 65 is relatively low. When the firing trigger 20 is fully drawn in (or in the fully closed position), the rotation of the motor 65 is at its maximum. In other words, the harder the user pulls on the firing trigger 20, the more voltage is applied to the motor 65, causing greater rates of rotation.

The handle 6 may include a middle handle piece 104 adjacent to the upper portion of the firing trigger 20. The handle 6 may also include a bias spring 112 that is connected between posts on the middle handle piece 104 and the firing trigger 20. The bias spring 112 may bias the firing trigger 20 to its fully open position. In that way, when the operator releases the firing trigger 20, the bias spring 112 will pull the firing trigger 20 to its open position, thereby deactivating the run motor switch 110 to stop rotation of the motor 65. Moreover, by virtue of the bias spring 112, any time a user closes the firing trigger 20, the user will experience resistance to the closing operation, thereby providing the user with feedback as to the amount of rotation exerted by the motor 65. Further, the operator could stop retracting the firing trigger 20 to thereby deactivate the run motor switch 110 and stop the motor 65. As such, the user may stop the deployment of the end effector 12, thereby providing a measure of control of the cutting/fastening operation to the operator.

The distal end of the helical gear drum 80 includes a distal drive shaft 120 that drives a ring gear 122, which mates with a pinion gear 124. The pinion gear 124 is connected to the main drive shaft 48 of the main drive shaft assembly. In that way, rotation of the motor 65 causes the main drive shaft assembly to rotate, which causes actuation of the end effector 12, as described above.

The ring 84 threaded on the helical gear drum 80 may include a post 86 that is disposed within a slot 88 of a slotted arm 90. The slotted arm 90 has an opening 92 its opposite end 94 that receives a pivot pin 96 that is connected between the handle exterior side pieces 59, 60. The pivot pin 96 is also disposed through an opening 100 in the firing trigger 20 and an opening 102 in the middle handle piece 104.

In addition, the handle 6 may include a reverse motor switch (or end-of-stroke switch) 130 and a stop motor (or beginning-of-stroke) switch 142. In various embodiments, the reverse motor switch 130 may be a limit switch located at the distal end of the helical gear drum 80 such that the ring 84 threaded on the helical gear drum 80 contacts and trips the reverse motor switch 130 when the ring 84 reaches the distal end of the helical gear drum 80. The reverse motor switch 130, when activated, sends a signal (i.e., permits current to flow) to the motor 65 to reverse its rotation direction, thereby withdrawing the knife 32 of the end effector 12 following the cutting operation.

The stop motor switch 142 may be, for example, a normally-closed limit switch. In various embodiments, it may be located at the proximate end of the helical gear drum 80 so that the ring 84 trips the switch 142 when the ring 84 reaches the proximate end of the helical gear drum 80.

In operation, when an operator of the instrument 10 applies an actuation motion to the firing trigger 20, the run motor switch 110 detects the deployment of the firing trigger 20 and sends a signal (i.e., permits current to flow) to the motor 65 to cause forward rotation of the motor 65, for example, at a rate proportional to how hard the operator pulls back the firing trigger 20. The forward rotation of the motor 65 in turn causes the ring gear 78 at the distal end of the planetary gear assembly 72 to rotate, thereby causing the helical gear drum 80 to rotate, causing the ring 84 threaded on the helical gear drum 80 to travel distally along the helical gear drum 80. The rotation of the helical gear drum 80 also drives the main drive shaft assembly as described above, which in turn causes deployment of the knife 32 in the end effector 12. That is, the knife 32 and sled 33 are caused to distally traverse the channel 22 longitudinally, thereby cutting tissue clamped in the end effector 12. Also, the stapling operation of the end effector 12 is caused to happen in embodiments where a stapling-type end effector 12 is used.

By the time the cutting/stapling operation of the end effector 12 is complete, the ring 84 on the helical gear drum 80 will have reached the distal end of the helical gear drum 80, thereby causing the reverse motor switch 130 to be activated, which sends a signal (i.e., permits current to flow) to the motor 65 to cause the motor 65 to reverse its rotation. This in turn causes the knife 32 to retract, and also causes the ring 84 on the helical gear drum 80 to move back to the proximate end of the helical gear drum 80.

Figure 8:
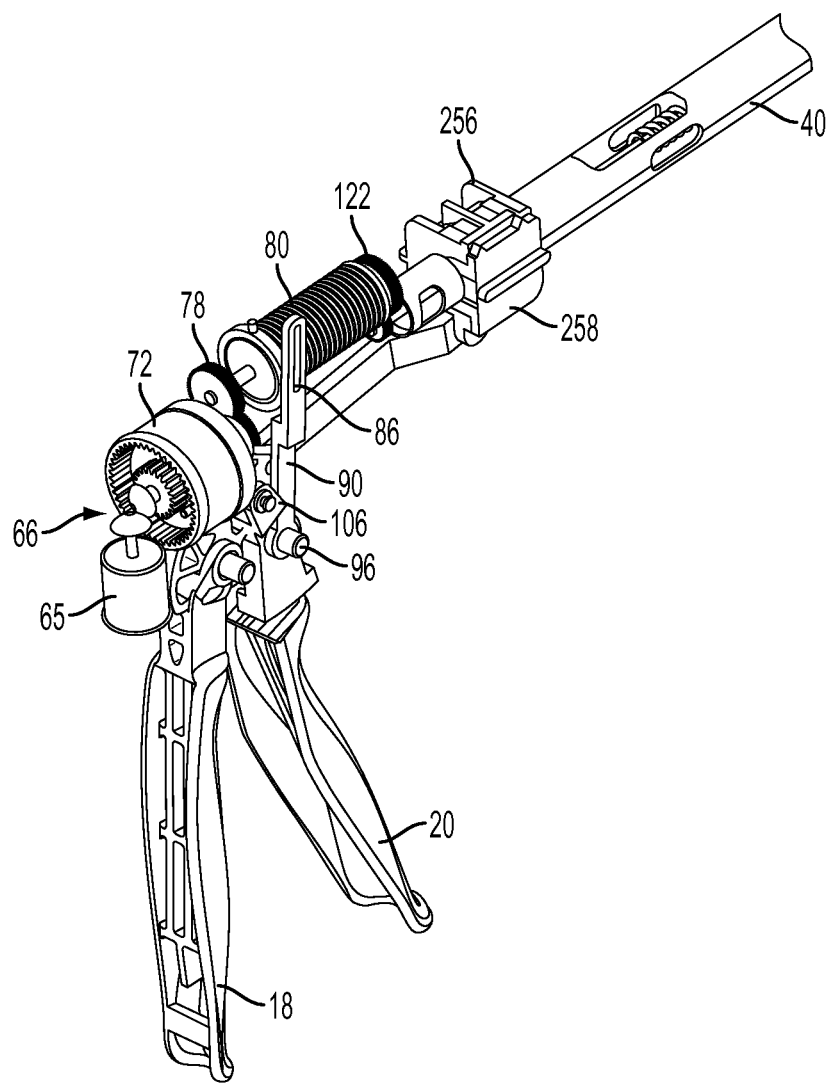
FIGS. 8 and 9 are partial perspective views of the handle according to various embodiments of the present invention.
Figure 9:
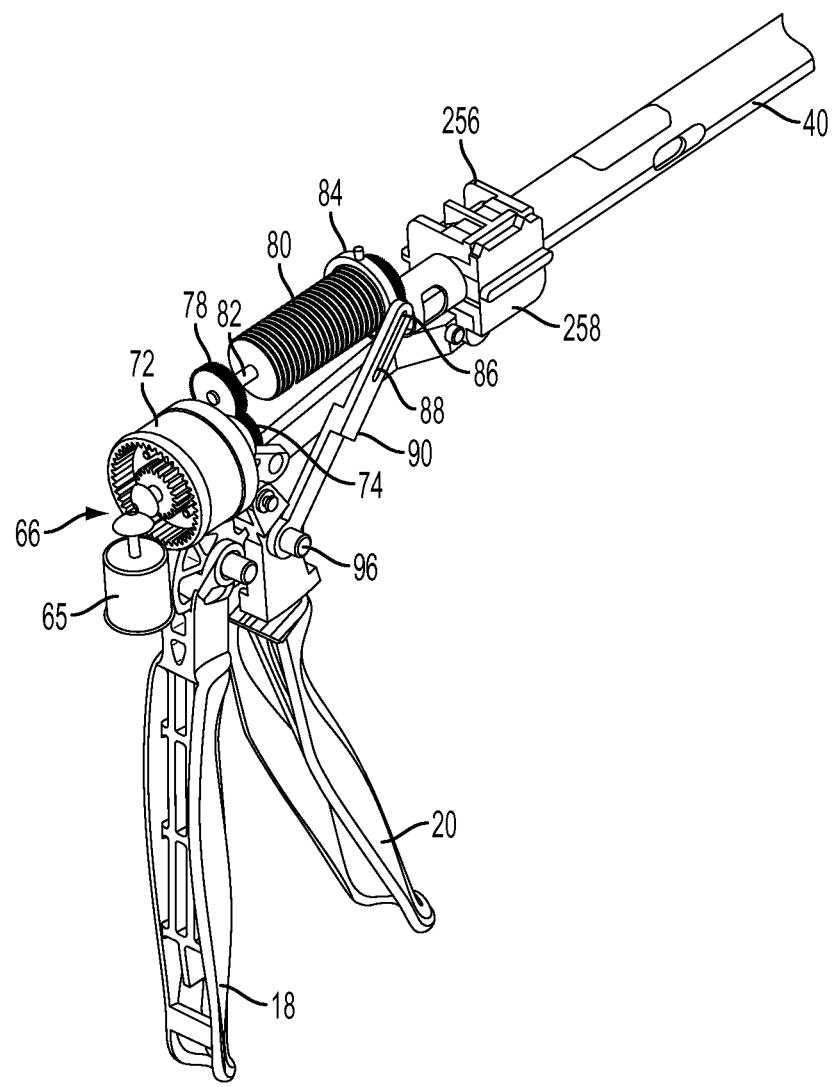

The middle handle piece 104 includes a backside shoulder 106 that engages the slotted arm 90 as best shown in FIGS. 8 and 9. The middle handle piece 104 also has a forward motion stop 107 that engages the firing trigger 20. The movement of the slotted arm 90 is controlled, as explained above, by rotation of the motor 65. When the slotted arm 90 rotates counter clockwise as the ring 84 travels from the proximate end of the helical gear drum 80 to the distal end, the middle handle piece 104 will be free to rotate counter clockwise. Thus, as the user draws in the firing trigger 20, the firing trigger 20 will engage the forward motion stop 107 of the middle handle piece 104, causing the middle handle piece 104 to rotate counter clockwise. Due to the backside shoulder 106 engaging the slotted arm 90, however, the middle handle piece 104 will only be able to rotate counter clockwise as far as the slotted arm 90 permits. In that way, if the motor 65 should stop rotating for some reason, the slotted arm 90 will stop rotating, and the user will not be able to further draw in the firing trigger 20 because the middle handle piece 104 will not be free to rotate counter clockwise due to the slotted arm 90.

Figure 10:
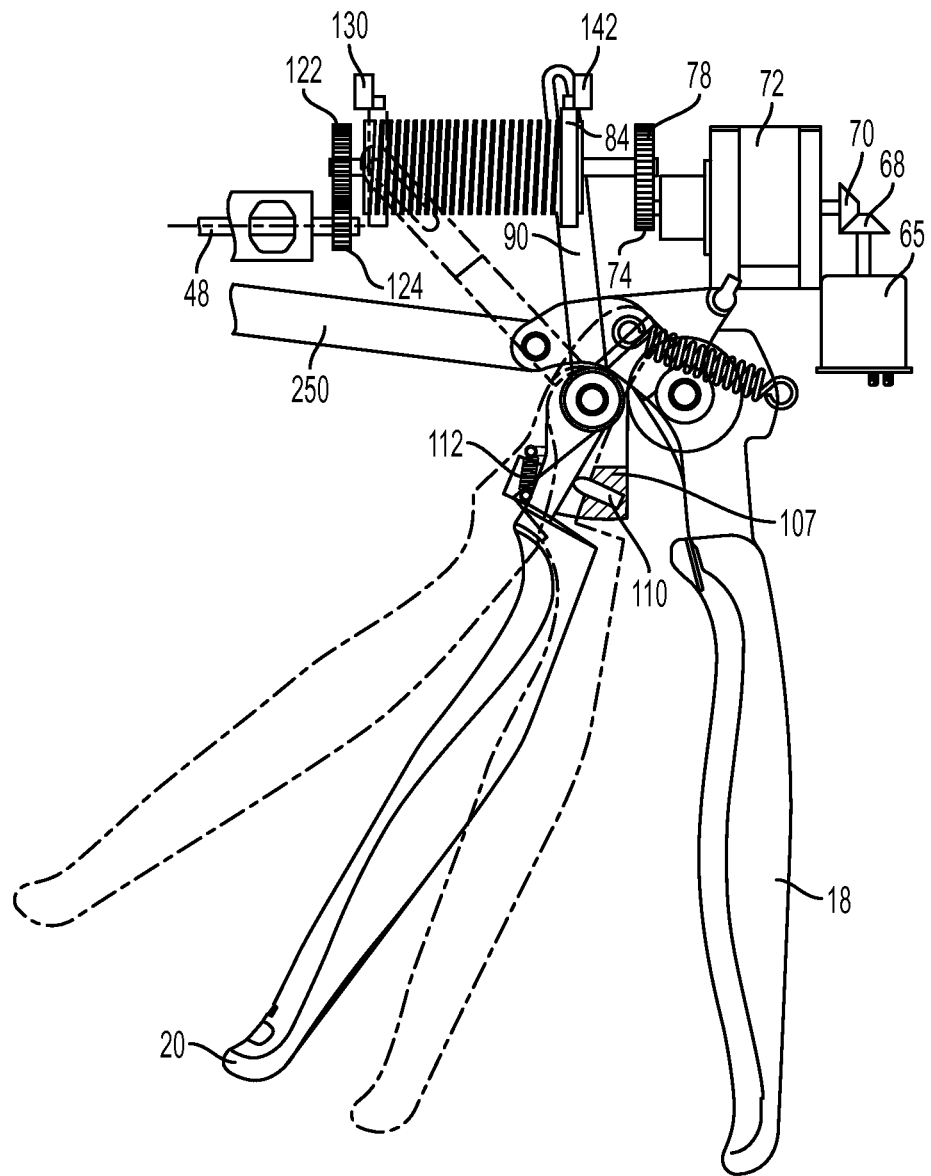
FIG. 10 is a side view of the handle according to various embodiments of the present invention.
Figure 10A:
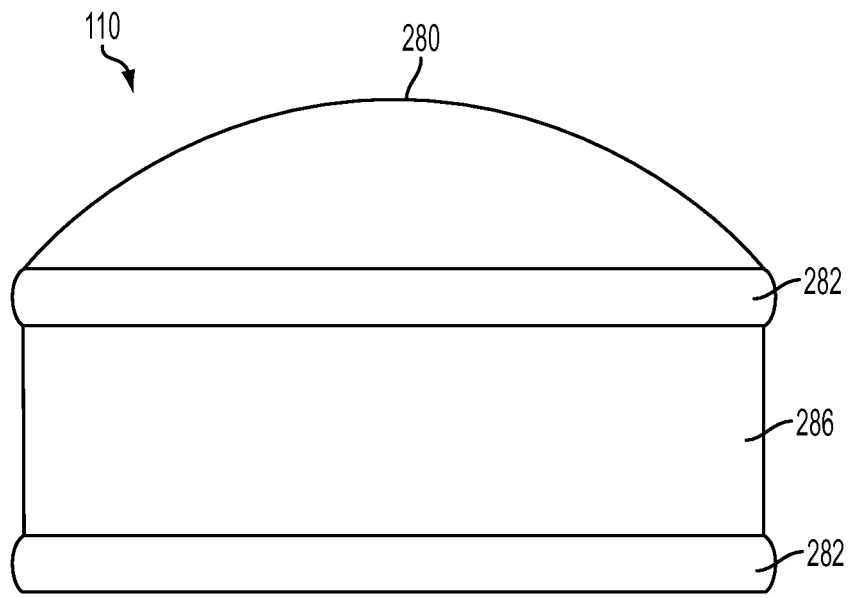
FIGS. 10A-10B illustrate a proportional sensor or switch that may be used according to various embodiments of the present invention.
Figure 10B:
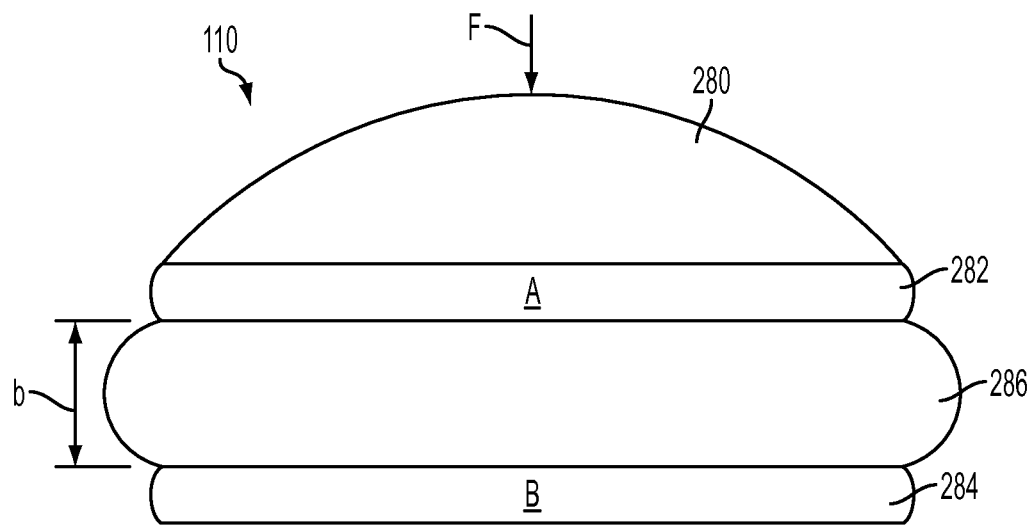

FIGS. 10A and 10B illustrate two states of a variable switches or sensors that may be used as the run motor switch 110 according to various embodiments of the present invention. The run motor switch 110 may include a face portion 280, a first electrode (A) 282, a second electrode (B) 284, and a compressible dielectric material 286 between the electrodes 282, 284, such as, for example, an electroactive polymer (EAP). The run motor switch 110 may be positioned such that the face portion 280 contacts the firing trigger 20 when retracted. Accordingly, when the firing trigger 20 is retracted, the dielectric material 286 is compressed, as shown in FIG. 10B, such that the electrodes 282, 284 are closer together. Since the distance "b" between the electrodes 282, 284 is directly related to the impedance between the electrodes 282, 284, the greater the distance the more impedance, and the closer the distance the less impedance. In that way, the amount that the dielectric 286 is compressed due to retraction of the firing trigger 20 (denoted as force "F" in FIG. 10B) is proportional to the impedance between the electrodes 282, 284, which can be used to proportionally control the motor 65.

Components of an exemplary closure system for closing (or clamping) the anvil 24 of the end effector 12 by retracting the closure trigger 18 are also shown in FIGS. 7-10. In the illustrated embodiment, the closure system includes a yoke 250 connected to the closure trigger 18 by a pivot pin 251 inserted through aligned openings in both the closure trigger 18 and the yoke 250. A pivot pin 252, about which the closure trigger 18 pivots, is inserted through another opening in the closure trigger 18 which is offset from where the pin 251 is inserted through the closure trigger 18. Thus, retraction of the closure trigger 18 causes the upper part of the closure trigger 18, to which the yoke 250 is attached via the pin 251, to rotate counterclockwise. The distal end of the yoke 250 is connected, via a pin 254, to a first closure bracket 256. The first closure bracket 256 connects to a second closure bracket 258. Collectively, the closure brackets 256, 258 define an opening in which the proximate end of the proximate closure tube 40 (see FIG. 4) is seated and held such that longitudinal movement of the closure brackets 256, 258 causes longitudinal motion by the proximate closure tube 40. The instrument 10 also includes a closure rod 260 disposed inside the proximate closure tube 40. The closure rod 260 may include a window 261 into which a post 263 on one of the handle exterior pieces, such as exterior lower side piece 59 in the illustrated embodiment, is disposed to fixedly connect the closure rod 260 to the handle 6. In that way, the proximate closure tube 40 is capable of moving longitudinally relative to the closure rod 260. The closure rod 260 may also include a distal collar 267 that fits into a cavity 269 in proximate spine tube 46 and is retained therein by a cap 271 (see FIG. 4).

In operation, when the yoke 250 rotates due to retraction of the closure trigger 18, the closure brackets 256, 258 cause the proximate closure tube 40 to move distally (i.e., away from the handle end of the instrument 10), which causes the distal closure tube 42 to move distally, which causes the anvil 24 to rotate about the pivot pins 25 into the clamped or closed position. When the closure trigger 18 is unlocked from the locked position, the proximate closure tube 40 is caused to slide proximately, which causes the distal closure tube 42 to slide proximately, which, by virtue of the tab 27 being inserted in the window 45 of the distal closure tube 42, causes the anvil 24 to pivot about the pivot pins 25 into the open or unclamped position. In that way, by retracting and locking the closure trigger 18, an operator may clamp tissue between the anvil 24 and channel 22, and may unclamp the tissue following the cutting/stapling operation by unlocking the closure trigger 20 from the locked position.

Figure 11:
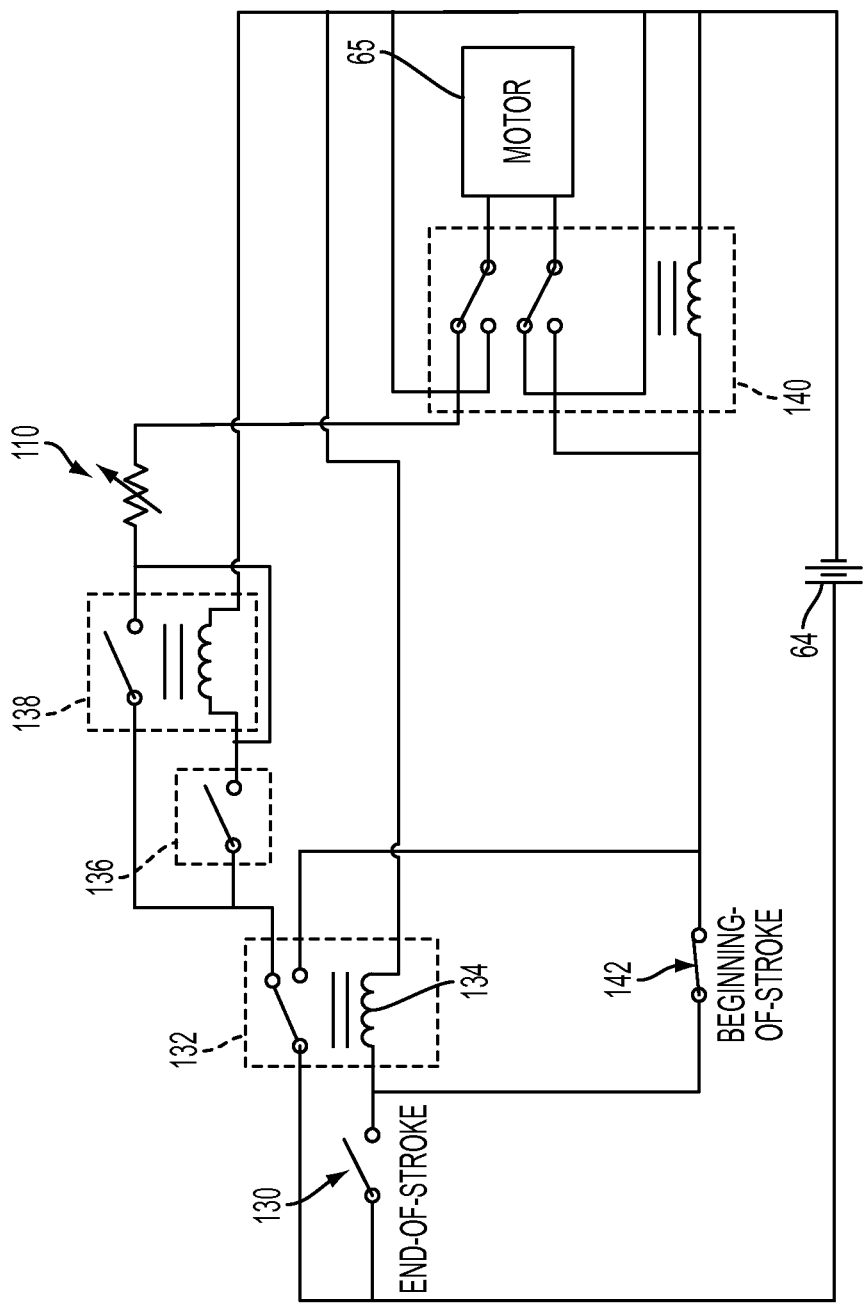
FIG. 11 is a schematic diagram of a current control circuit used in the instrument according to various embodiments of the present invention.

FIG. 11 is a schematic diagram of a current control circuit of the instrument 10 according to various embodiments of the present invention. When an operator initially pulls in the firing trigger 20 after locking the closure trigger 18, the run motor switch 110 is activated, allowing current to flow therethrough. If the normally-open reverse motor sensor switch 130 is open (meaning the end of the end effector stroke has not been reached), current will flow to a single pole, double throw relay 132. Since the reverse motor sensor switch 130 is not closed, the inductor 134 of the relay 132 will not be energized, so the relay 132 will be in its non-energized state. The circuit also includes a cartridge lockout switch 136. If the end effector 12 includes a staple cartridge 34, the switch 136 will be in the closed state, allowing current to flow. Otherwise, if the end effector 12 does not include a staple cartridge 34, the switch 136 will be open, thereby preventing the battery 64 from powering the motor 65.

When the staple cartridge 34 is present, the switch 136 is closed, which energizes a single pole, single throw relay 138. When the relay 138 is energized, current flows through the relay 136, through the variable resistor (run motor) switch 110, and to the motor 65 via a double pole, double throw relay 140, thereby powering the motor 65 and allowing it to rotate in the forward direction.

When the end effector 12 reaches the end of its stroke, the reverse motor switch 130 will be activated, thereby closing the reverse motor switch 130 and energizing the relay 134. This causes the relay 134 to assume its energized state, which causes current to bypass the cartridge lockout switch 136 and variable resistor 110, and instead causes current to flow to both the normally-closed double pole, double throw relay 142 and back to the motor 65, but in a manner, via the relay 140, that causes the motor 65 to reverse its rotational direction.

Because the stop motor switch 142 is normally-closed, current will flow back to the relay 134 to keep it closed until the stop motor switch 142 opens. When the knife 32 is fully retracted, the stop motor switch 142 is activated, causing the stop motor switch 142 to open, thereby removing power from the motor 65.

In other embodiments, rather than a proportional-type switch 110, an on-off type sensor or switch could be used. In such embodiments, the rate of rotation of the motor 65 would not be proportional to the force applied by the operator. Rather, the motor 65 would generally rotate at a constant rate. But the operator would still experience force feedback because the firing trigger 20 is geared into the gear drive train.

As indicated above, there are several steps within the function of a stapler that generally must be accomplished in an established order. For example, once the closure trigger is clamped, the firing cycle may be actuated. After the knife has been fully deployed, then retraction of the system is the next sequential step. With the inclusion of a power source other than the user (i.e. batteries or pneumatics) the ability to reduce user initiated steps (and therefore device complexity) the system itself, as was discussed above, can begin to accomplish these steps itself.

It may be desirable, however, for the user to intuitively be able to delay, slow or stop these otherwise "automatic" actuations. For example, the same actuation button that would allow for firing initiation in a tactile feedback device like the devices disclosed in U.S. patent application Ser. No. 11/344,035, now U.S. Pat. No. 7,422,139, the disclosure of which is herein incorporated by reference in its entirety could be used to slow or stop an automatic return system by the user depressing the button during the retraction.

Figure 12:
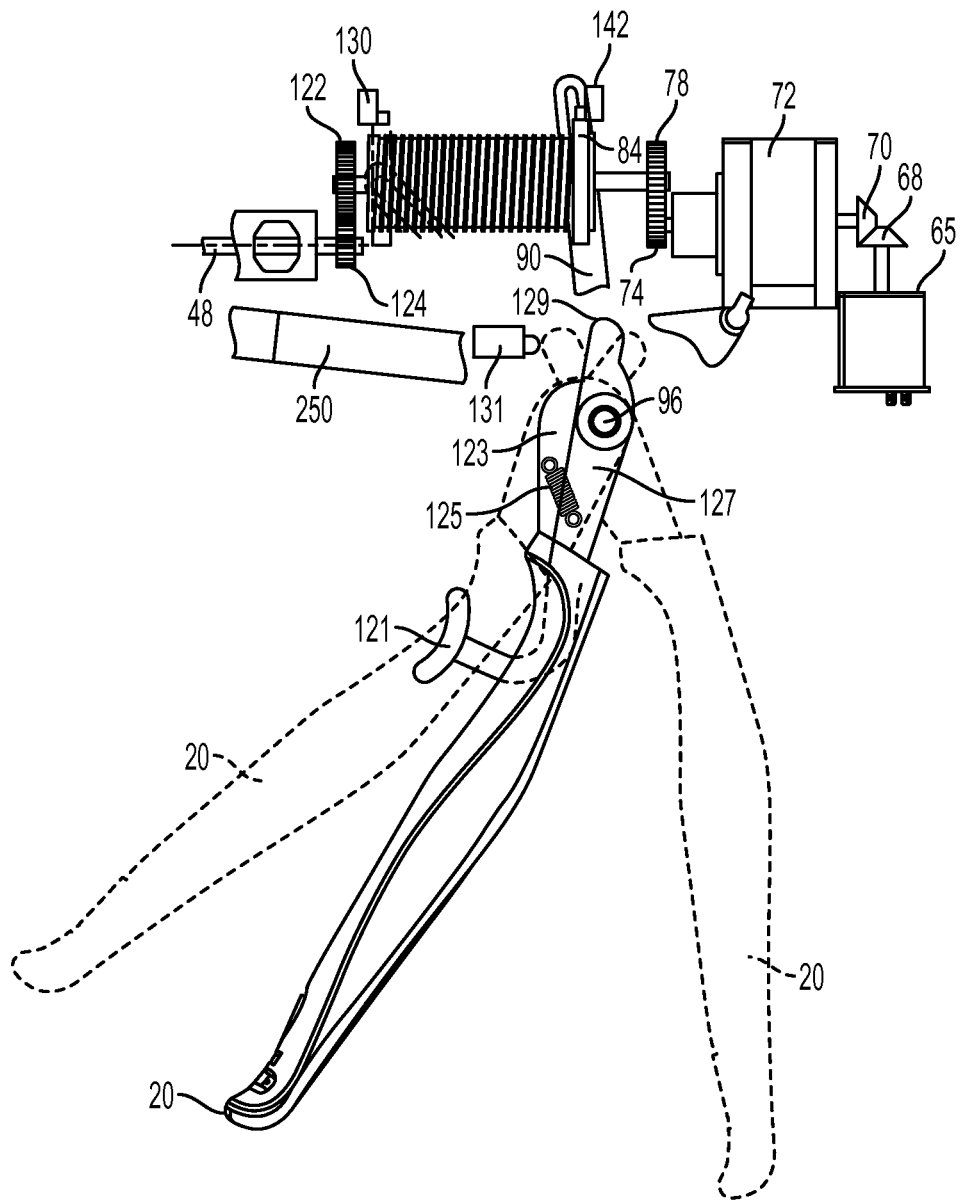
FIG. 12 is a side view of another handle according to various embodiments of the present invention.
Figure 13:
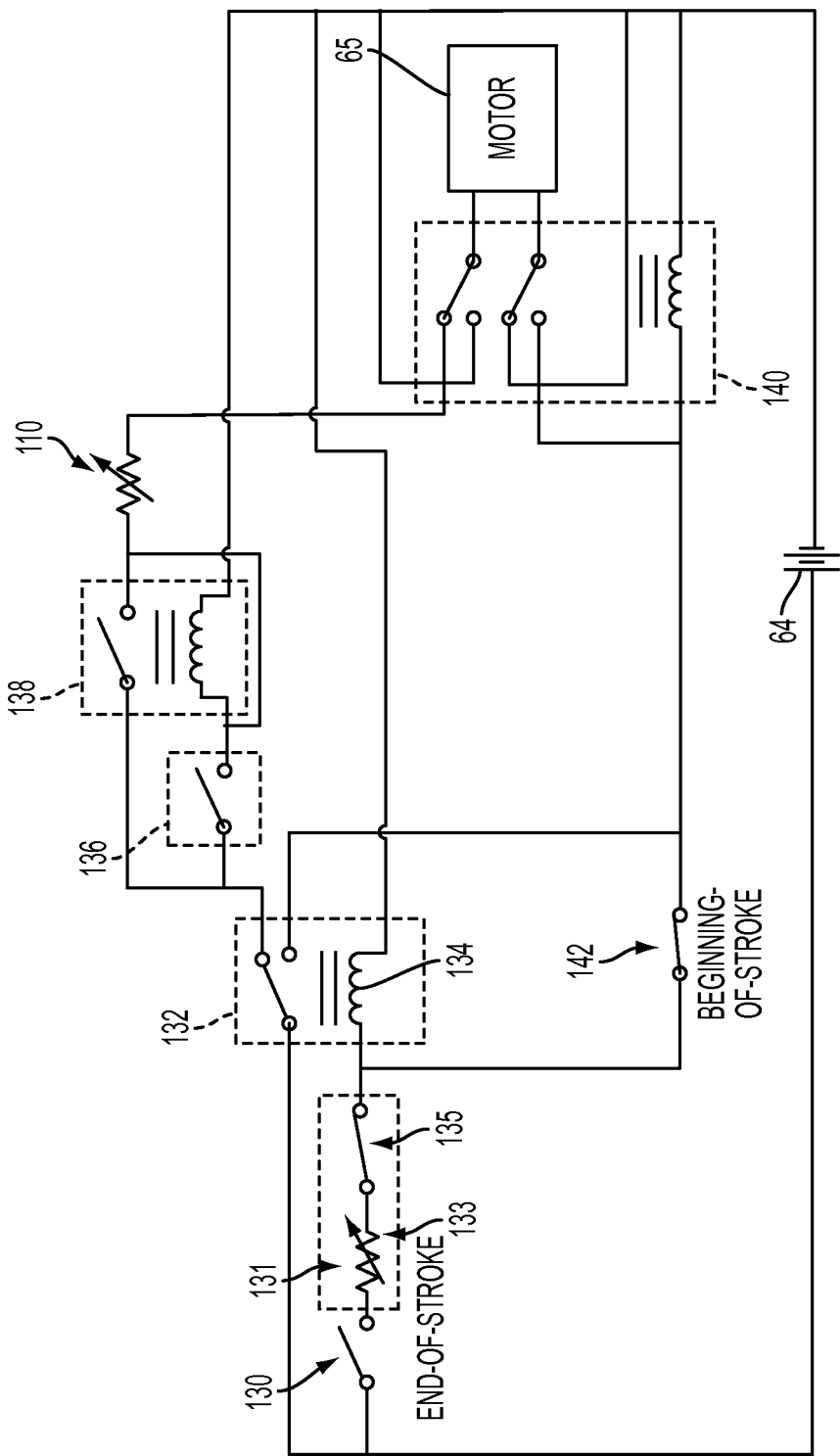
FIG. 13 is a schematic diagram of another current control circuit used in the instrument according to various embodiments of the present invention.

For example, FIGS. 12 and 13 illustrate another embodiment of the present invention wherein a retraction trigger 121 is supported on the firing trigger 20 for travel therewith. More specifically, the retraction trigger 121 is pivotally supported on firing trigger pin 96 and protrudes through a slot (not shown) in the firing trigger 20. A spring 125 is attached between a coupling portion 123 of the firing trigger 100 and a mounting portion 127 of the retraction trigger 121 to bias the retraction trigger 121 into an unactuated position. A second, normally-closed, retraction switch 131 is mounted within the handle and is oriented such that, as the firing trigger 20 is moved between a fully actuated position to a fully unactuated position, an activation portion 129 of the retraction trigger 121 does not activate the retraction switch 131. However, the mounting portion 127 and activation portion 129 of the retraction trigger 121 are so configured such that the activation portion 129 may be brought into activation contact with the retraction switch 131 by depressing the retraction trigger 121 towards the firing trigger 20 regardless of where the firing trigger 20 is located during the retraction process.

As was discussed above, when the end effector 12 reaches the end of its stroke, the end of stroke switch 130 will be activated. As shown in the example of FIG. 13, the retraction switch 131 is in series with the end-of-stroke switch 130. Because the retraction switch 131 is normally closed, relay 134 will be energized when both switches 130, 131 are closed. This causes the relay 134 to assume its energized state, which causes current to bypass the cartridge lockout sensor 136 and variable resistor 110. Current to flows to the double pole, double throw relay 140 and to the motor 65, but in a manner, via the relay 140, that causes the motor 65 to reverse its rotational direction. Because the beginning-of-stroke switch 142 is closed, current will flow back to the relay 134 to keep it closed until the switch 142 opens. When the knife 32 is fully retracted, the beginning-of-stroke switch 142 is opened, thereby removing power from the motor 65. If, however, the user wants to slow down the retraction process, the user may depress the retraction trigger 121 to activate the variable resistance portion 133 of the retraction switch 131. When the retraction trigger 121 is not depressed, the resistance of the variable resistance portion 133 is a minimum. When the trigger 121 is depressed, the resistance of the variable resistance portion 133 increases in proportion to the depressing force of the retraction trigger 121 to reduce the current to the motor 65. Further depression of the retraction trigger 121 will slow the retraction process until the normally closed contact 135 portion of the retraction switch 131 opens and stops the current flow to the motor 65. In various embodiments, once the user releases the retraction trigger 121, the spring 125 will move the retraction trigger 121 to an unactuated position and the contact portion 135 of switch 131 will return to the normally closed position and thereby permit current to flow again to the motor 65 to complete the retraction process.

Figure 14:
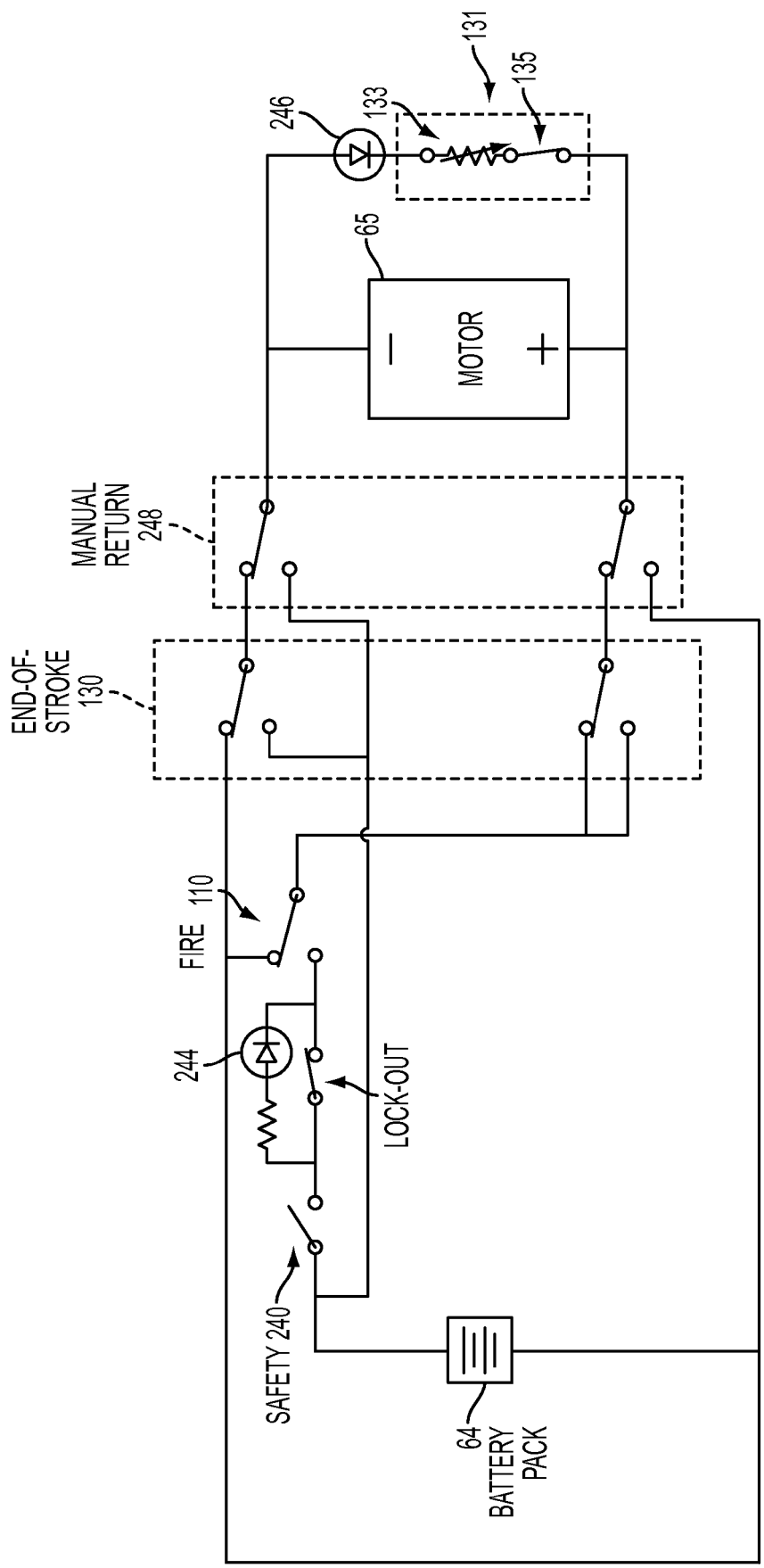
FIG. 14 is a schematic diagram of another current control circuit used in the instrument according to various embodiments of the present invention.

The unique and novel features of the retraction switch and retraction trigger arrangements described above may also be employed in connection with the various embodiments disclosed in U.S. Patent Application Publication No. US 2010/0076474 A1, and U.S. Pat. No. 7,422,139 which have both been herein incorporated by reference in their respective entireties. For example, FIG. 14 shows another embodiment of a current control circuit embodiment of the present invention. When (i) the run motor (or fire) switch 110 is closed (it is shown in an open state in FIG. 14), (ii) the safety switch 240 is closed (it is shown open in FIG. 14) indicating that the device safety is set, and (iii) the normally-closed lockout switch 242 is opened indicating that the instrument is not in a lock-out condition, current flows through the safety switch 240, through the lockout indicator 244 (which may be a LED as shown in FIG. 14) to the motor 65. When the end of the cutting stroke is reached, the end-of-stroke or direction switch 130 is switched, reversing the direction of the motor 65 (with the fire switch 110 also having been released). In this state, current also flows through a reverse direction indicator 246, such as an LED, providing a visual indication that the motor direction has been reversed.

As shown in FIG. 14, the circuit may also comprise a manual return switch 248. The operator may manually actuate this switch if the cutting instrument 32 has only been partially fired. Switching the manual return switch 248 causes the motor 65 to reverse rotate, causing the cutting instrument 32 to return to its original or home position. If, the user desires to slow down or stop the retraction process, the user depresses the retraction trigger 121 to activate the variable resistance portion 133 of the retraction switch 131. When the trigger 121 is depressed, the resistance increases in portion to the depressing force to reduce the current to the motor 65. Further depression of the retraction trigger 121 will slow the retraction process until the normally closed contact 135 portion of the retraction switch 131 opens and stops the current flow to the motor 65. In various embodiments, once the user releases the retraction trigger 121, the spring 125 will move the retraction trigger 121 to an unactuated position and the contact portion 135 of switch 131 will return to the normally closed position and thereby permit current to flow again to the motor 65 to complete the retraction process.

Figure 15:
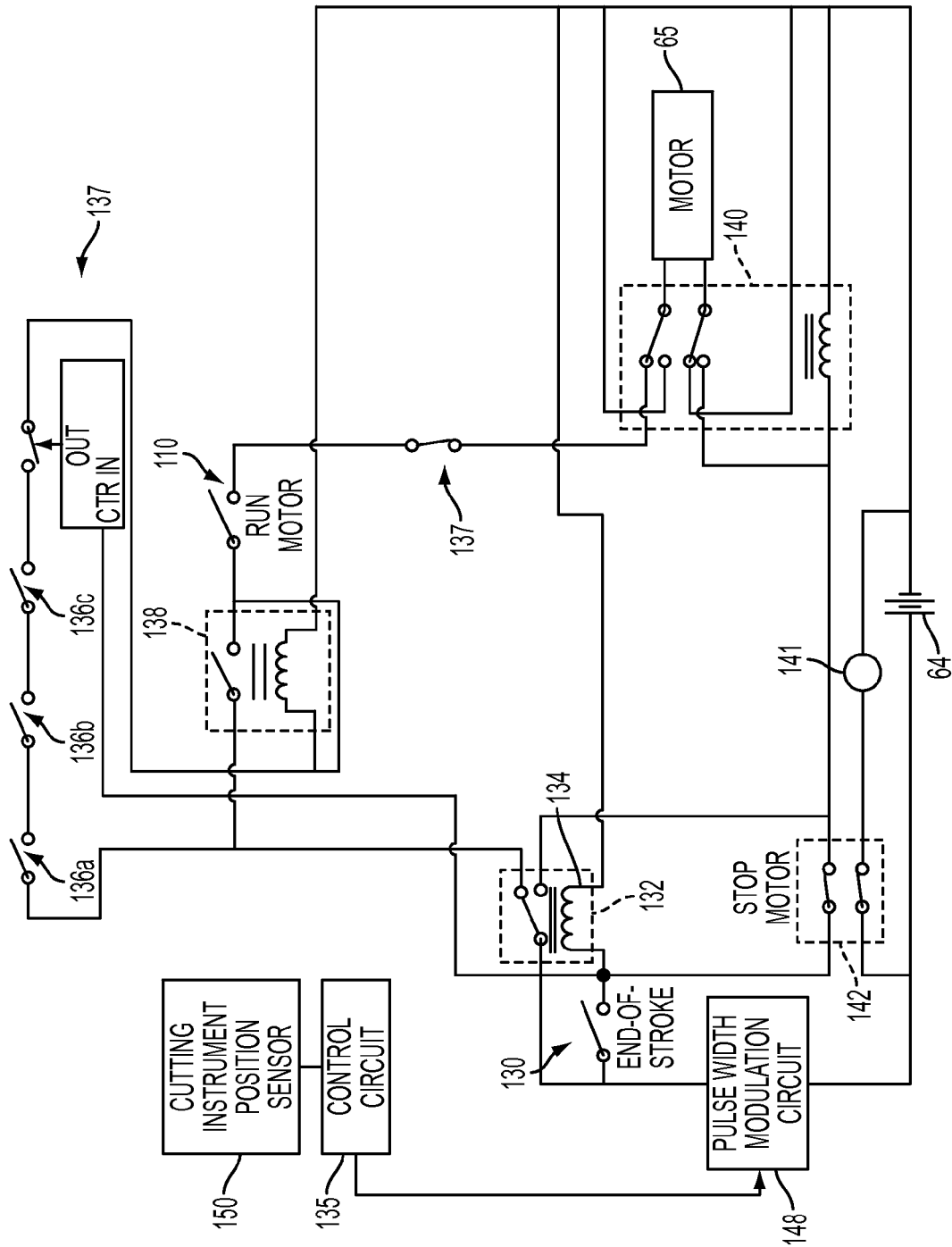
FIG. 15 is a schematic diagram of another circuit used in the instrument according to various embodiments of the present invention.

Additional configurations for motorized surgical instruments are disclosed in published U.S. Patent Application Publication No. US 2010/0076474 A1, entitled "Motor-Driven Surgical Cutting Instrument," which is incorporated herein by reference in its entirety. For example, FIG. 15 is a schematic diagram of another current control circuit according to various embodiments of the present invention. In various embodiments, the motor control circuit may include one of more integrated circuits (ICs), such as, for example, a processor, memory, microcontroller, time circuits, etc. In other embodiments, the motor control circuit may not comprise any ICs. Such a non-IC current control circuit may be advantageous because it is often difficult, complicated, and expensive to sterilize a surgical instrument including ICs.

When an operator initially applies an actuation motion to the firing trigger 20 after locking the closure trigger 18, the run motor switch 110 is activated (or closed), allowing current to flow therethrough. If the normally open reverse motor sensor switch 130 is open (meaning the end of the end effector stroke has not been reached), current will flow to a single pole, double throw relay 132. When the reverse motor sensor switch 130 is not closed, a coil 134 of the relay 132 will not be energized, so the relay 132 will be in its de-energized state.

As shown in FIG. 15, the circuit may also include a resistive element 144 and a switch 146 connected in parallel, with the paralleled elements connected in series with the relay 132. The resistive element 144 and the switch 146 are also connected to the power source 64. The switch 146 may be controlled by a control circuit 148 that is responsive to the cutting instrument position sensor 150. According to various embodiments, the control circuit 148 may open the switch 146 when the cutting instrument 32 is (i) very near to the beginning of its stroke and (ii) very near to the end of its stroke. For example, the control circuit may open the switch when the cutting instrument 32 is (i) 0.001 inches from the beginning point of its stroke and (ii) 0.001 inches from the end of its stroke, as determined by the cutting instrument position sensor 150. With the switch 146 open, current flows through the resistive element 144, and then through the relay 132, the relay 138, the run motor sensor switch 110, to the motor 65. Current flowing through the resistive element 144 reduces the magnitude of the current delivered to the motor 65, thereby reducing the power delivered by the motor 65. Thus, when the cutting instrument 32 is (i) very near to the beginning of its stroke or (ii) very near to the end of its stroke, the power delivered by the motor 65 is reduced. Conversely, once the cutting instrument 32 moves sufficiently far from its beginning point or end of stroke point, the control circuit 148 may close the switch 146, thereby shorting the resistive element 144, thereby increasing the current to the motor 65, thereby increasing the power delivered by the motor.

According to various embodiments, the current control circuit further includes lockout sensor switches 136a-d collectively defining an interlock circuit 137 through which current from the relay 132, when de-energized, passes in order for electrical operation of the motor 65 to be initiated. Each lockout sensor switch 136a-d may be configured to maintain an open (i.e., non-conductive) switch state or a closed (i.e., conductive) switch state responsive to the presence or absence, respectively, of a corresponding condition. Any of the corresponding conditions, if present when the instrument 10 is fired, may result in an unsatisfactory cutting and stapling operation and/or damage to the instrument 10. Conditions to which the lockout sensor switches 136a-d may respond include, for example, (a) the absence of the staple cartridge 34 in the channel 22, (b) the presence of a spent (e.g., previously fired) staple cartridge 34 in the channel 22, and (c) an open (or otherwise insufficiently closed) position of the anvil 24 with respect to the channel 22. Other conditions to which the lockout sensor switches 136a-d may respond, such as component wear, may be inferred based upon an accumulated number of firing operations produced by the instrument 10. Accordingly, in various embodiments, if any of these conditions exists, the corresponding lockout sensor switches 136a-d maintain an open switch state, thus preventing passage of the current necessary to initiate operation of the motor 65. Passage of current by the lockout sensors 136a-d is allowed, in various embodiments, only after all of the conditions have been remedied. It will be appreciated that the above-described conditions are provided by way of example only, and that additional lockout sensor switches for responding to other conditions detrimental to operation of the instrument 10 may be provided. It will similarly be appreciated that for embodiments in which one or more of the above-described conditions may not exist or are of no concern, the number of lockout sensor switches may be fewer than that depicted.

As shown in FIG. 15, the lockout sensor switch 136a may be implemented using a normally open switch configuration such that a closed switch state is maintained when the staple cartridge 34 is in a position corresponding to its proper receipt by the channel 22. When the staple cartridge 34 is not installed in the channel 22, or is installed improperly (e.g., mis-aligned), the lockout sensor switch 136a maintains an open switch state. Lockout sensor switch 136b may be implemented using a normally open switch configuration such that a closed switch state is maintained only when an unspent staple cartridge 34 (i.e., a staple cartridge 34 having a sled 33 in the unfired position) is present in the channel 22. The presence of a spent staple cartridge 34 in the channel 22 causes the lockout sensor switch 136b to maintain an open switch state. Lockout sensor switch 136c may be implemented using a normally open switch configuration such that a closed switch state is maintained when the anvil 24 is in a closed position with respect to the channel 22. The lockout sensor switch 136c may be controlled in accordance with a time delay feature wherein a closed switch state is maintained only after the anvil 24 is in the closed position for a predetermined period of time.

Lockout sensor switch 136d may be implemented using a normally closed switch configuration such that a closed switch state is maintained only when an accumulated number of firings produced by the instrument 10 is less than a pre-determined number. The lockout sensor switch 136d may be in communication with a counter 139 configured for maintaining a count representative of the accumulated number of firing operations performed by the instrument 10, comparing the count to the pre-determined number, and controlling the switch state of the lockout sensor switch 136d based upon the comparison. Although shown separately in FIG. 15, it will be appreciated that counter 139 may be integral with the lockout sensor switch 136d so as to form a common device. Preferably, the counter 139 is implemented as an electronic device having an input for incrementing the maintained count based upon the transition of a discrete electrical signal provided thereto. It will be appreciated that a mechanical counter configured for maintaining the count based upon a mechanical input (e.g., retraction of the firing trigger 20) may be used instead. When implemented as an electronic device, any discrete signal present in the electrical circuit that transitions once for each firing operation may be utilized for the counter 139 input. As shown in FIG. 15, for example, the discrete electrical signal resulting from actuation of the end-of-stroke sensor 130 may be utilized. The counter 139 may control the switch state of lockout sensor switch 136d such that a closed switch state is maintained when the maintained count is less than a pre-determined number stored within the counter 139. When the maintained count is equal to the pre-determined number, the counter 139 causes the lockout sensor switch 136d to maintain an open switch state, thus preventing the passage of current therethrough. It will be appreciated that the pre-determined number stored by the counter 139 may be selectively adjusted as required. According to various embodiments, the counter 304 may be in communication with an external display (not shown), such as an LCD display, integral to the instrument 10 for indicating to a user either the maintained count or the difference between the pre-determined number and the maintained count.

According to various embodiments, the interlock circuit 137 may comprise one or more indicators visible to the user of the instrument 10 for displaying a status of at least one of the lockout sensor switches 136a-d. More details regarding such indicators may be found in published U.S. Patent Application Publication No. 2007/0175956, entitled "Electronic Lockouts and Surgical Instrument Including Same," which is incorporated herein by reference in its entirety. This application also includes example mounting arrangements and configurations for the lockout sensor switches 136a-d.

In the illustrated embodiment, when the lockout sensor switches 136a-d collectively maintain a closed switch state, a single pole, single throw relay 138 is energized. When the relay 138 is energized, current flows through the relay 138, through the run motor switch sensor 110, and to the motor 65 via a double pole, double throw relay 140, thereby powering the motor 65, allowing it to rotate in the forward direction. According to various embodiments, because the output of the relay 138, once energized, maintains the relay 138 in an energized state until relay 132 is energized, the interlock circuit 137 will not function to prevent operation of the motor 165 once initiated, even if one or more of the interlock sensor switches 136a-d subsequently maintains an open switch state. In other embodiments, however, it may be necessary or otherwise desirable to connect the interlock circuit 137 and the relay 138 such that one or more the lockout sensor switches 136a-d must maintain a closed switch state in order to sustain operation of the motor 165 once initiated.

Rotation of the motor in the forward direction causes the ring to move distally and thereby de-actuate the stop motor sensor switch 142 in various embodiments. Because the switch 142 is normally closed, a solenoid 141 connected to the switch 142 may be energized. The solenoid 141 may be a conventional push-type solenoid that, when energized, causes a plunger (not shown) to be axially extended. Extension of the plunger may operate to retain the closure trigger 18 in the retracted position, thus preventing the anvil 24 from opening while a firing operation is in progress (i.e., while the switch 142 is not actuated). Upon de-energization of the solenoid 141, the plunger is retracted such that manual release of the closure trigger 18 is possible.

When the actuation member portion reaches the distal most end of its stroke, the reverse motor switch 130 will be activated, thereby closing the switch 130 and energizing the relay 132. This causes the relay 132 to assume its energized state (not shown in FIG. 11), which causes current to bypass the interlock circuit 137 and run motor sensor switch 110, and instead causes current to flow to both the normally-closed double pole, double throw relay 140 and back to the motor 65, but in a manner, via the relay 140, that causes the motor 65 to reverse its rotational direction. Because the stop motor sensor switch 142 is normally closed, current will flow back to the relay 132 to keep it energized until the switch 142 opens. When the knife 32 is fully retracted, the stop motor sensor switch 142 is activated, causing the switch 142 to open, thereby removing power from the motor 65, and de-energizing the solenoid 141.

Figure 15A:
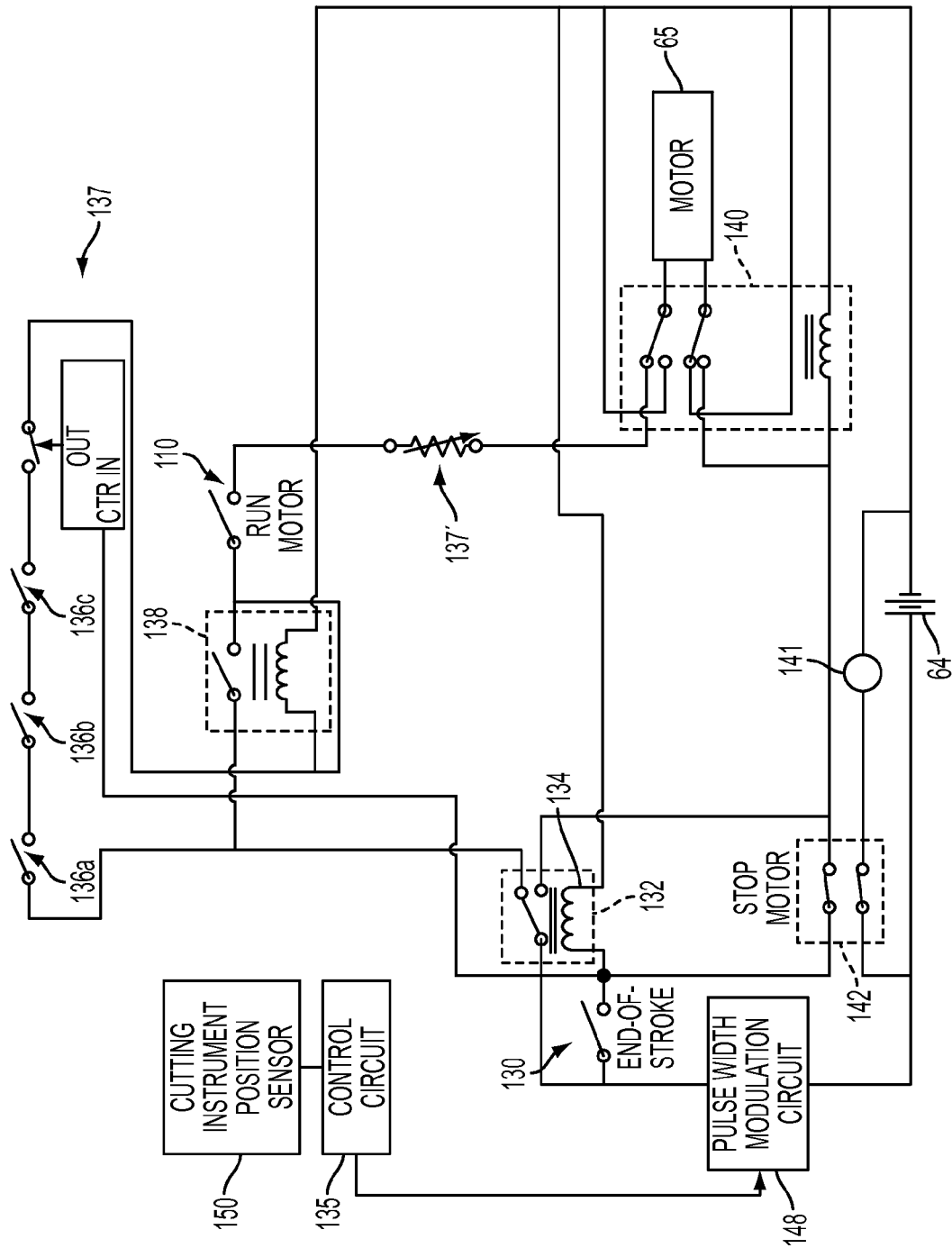
FIG. 15A is a schematic diagram of another current control circuit used in the instrument according to various embodiments of the present invention.
Figure 15B:
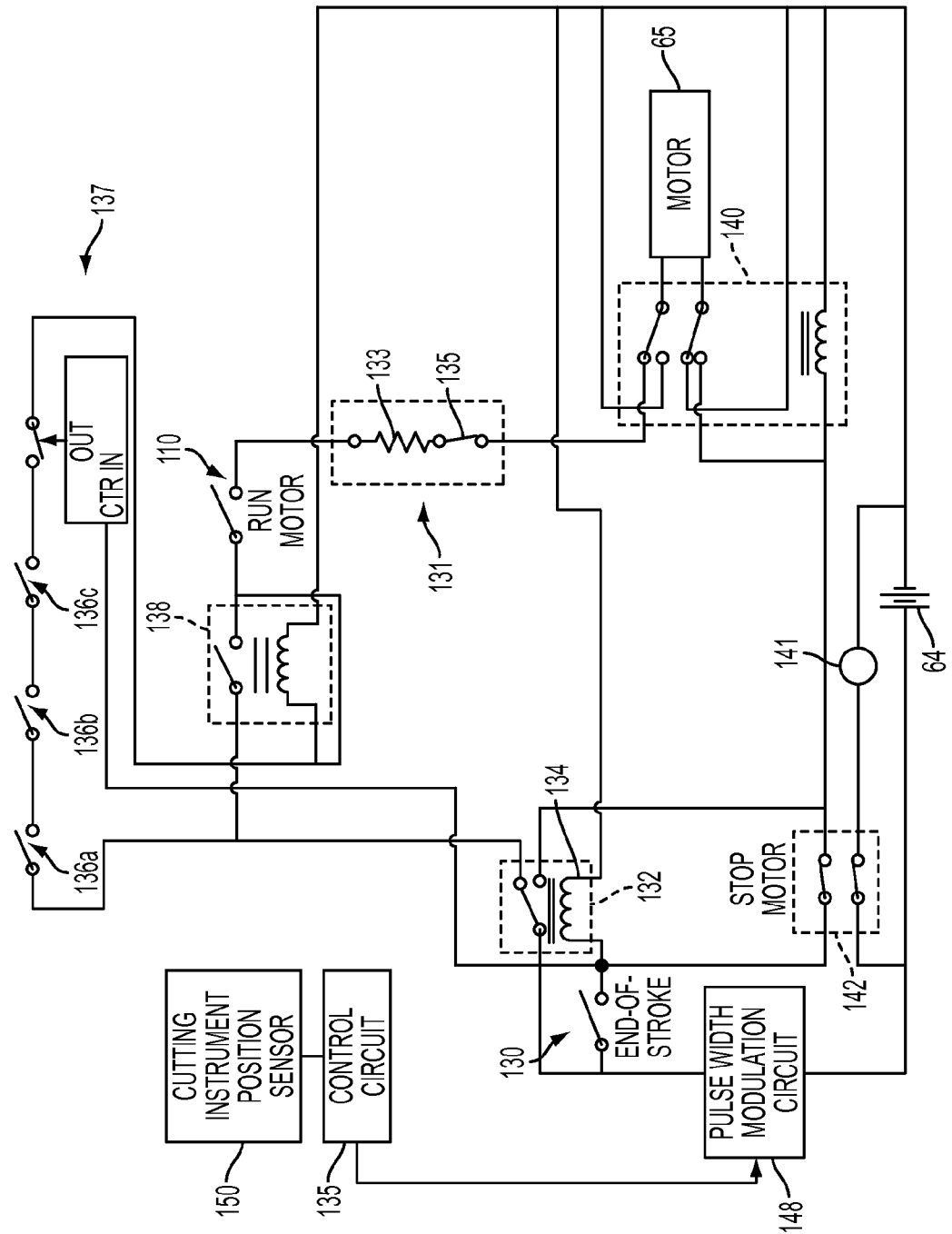
FIG. 15B is a schematic diagram of another current control circuit used in the instrument according to various embodiments of the present invention.

In the embodiment depicted in FIG. 15, a normally closed retraction switch 137 is employed which interfaces with retraction trigger 121 (not shown in FIG. 15). When retraction switch 137 is activated, it opens to stop the flow of current to the motor 65. In alternative embodiments (FIG. 15A), the normally closed retraction switch 137 could be replaced with a variable resistor 137' that interfaces with retraction trigger 121. In such embodiment, when the retraction trigger 121 is not depressed, the resistance of the variable resistor is minimal to allow maximum current to flow to the motor 65. When depressed the resistance increases in proportion to the depressing force to reduce current to the motor. Such variable resistor may also be replaced with the retraction switch 131 as described above (see FIG. 15B).

Accidental actuation prevention for a powered endocutter: With the introduction of powered systems that no longer limit the device function to the force capabilities of the user, inadvertent initiation of the firing cycle may become a much more prevalent issue. It will be increasing ease to "bump" the activation control and have the instrument begin firing thereby tripping the lockout of the cartridge or even "jamming" it on tissue, as the user is unaware it has already begun firing. Various lockout arrangements are disclosed in U.S. Pat. No. 7,644,848, entitled "Electronic Lockouts and Surgical Instrument Including Same" to Swayze et al., the disclosure of which is herein incorporated by reference in its entirety. To eliminate this issue secondary unlock activator switches or buttons could be used to unlock the firing mechanism. This is much the same as the two switch systems used in the power saw industry as well as the military to protect against accidental actuation. The secondary switch can either release the lock on the firing trigger or merely energize the power to the control.

Figure 16:
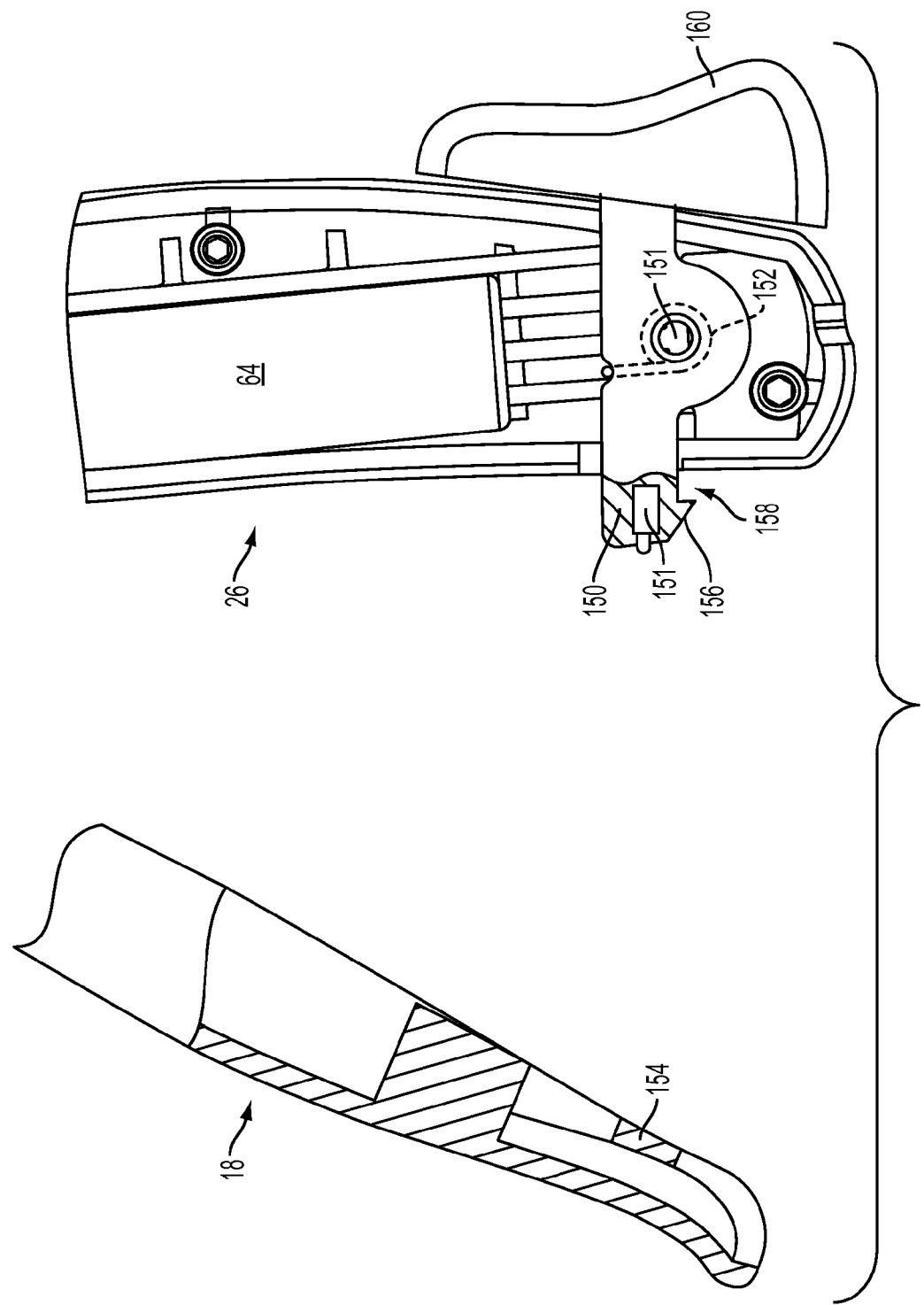
FIGS. 16-17 illustrate different mechanisms for locking the closure trigger according to various embodiments of the present invention.
Figure 17:
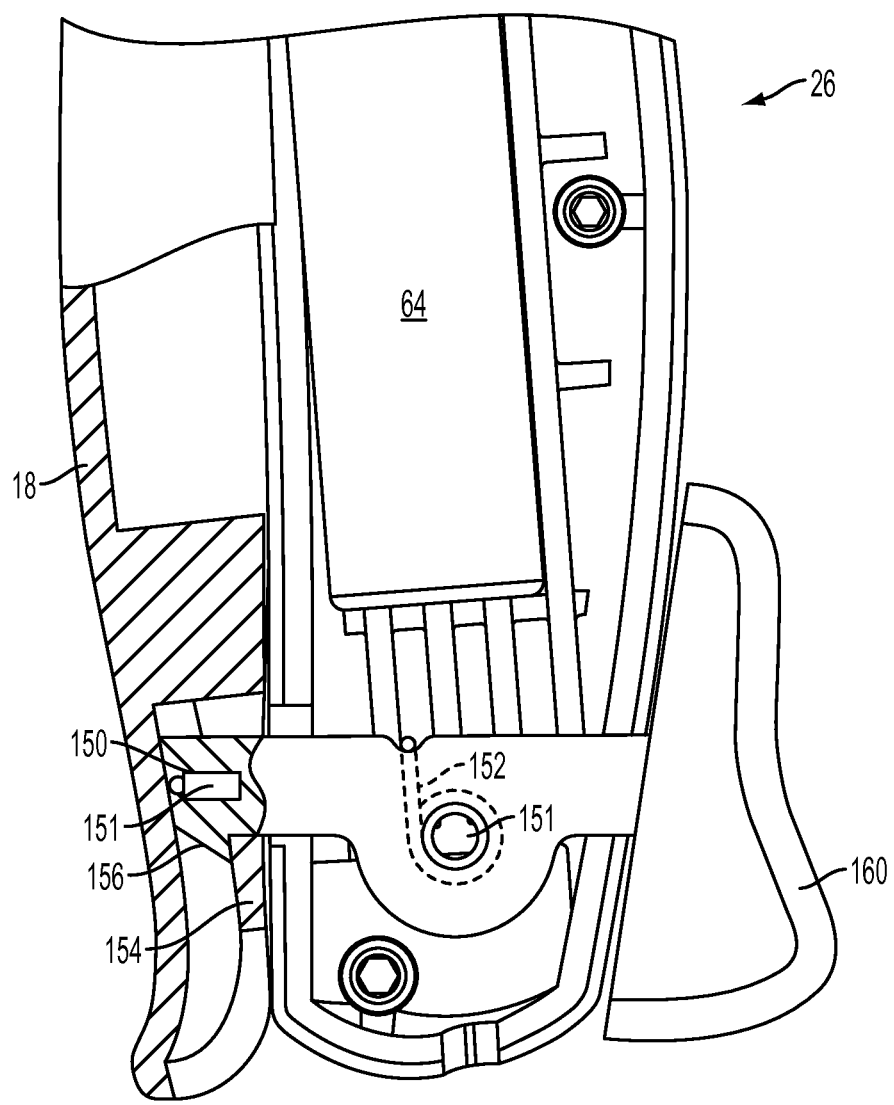

As mentioned above, in using a two-stroke motorized instrument, the operator first pulls back and locks the closure trigger 18. FIGS. 16 and 17 show one embodiment of a way to lock the closure trigger 18 to the pistol grip portion 26 of the handle 6. In the illustrated embodiment, the pistol grip portion 26 includes a hook 150 that is biased to rotate CCW about a pivot point 151 by a torsion spring 152. Also, the closure trigger 18 includes a closure bar 154. As the operator draws in the closure trigger 18, the closure bar 154 engages a sloped portion 156 of the hook 150, thereby rotating the hook 150 upward (or CW in FIGS. 16 and 17) until the closure bar 154 completely passes the sloped portion 156 passes into a recessed notch 158 of the hook 150, which locks the closure trigger 18 in place. The operator may release the closure trigger 18 by pushing down on a slide button release 160 on the back or opposite side of the pistol grip portion 26. Pushing down the slide button release 160 rotates the hook 150 CW such that the closure bar 154 is released from the recessed notch 158. Other arrangements for releasably locking the closure trigger 18 are disclosed in U.S. Pat. No. 7,422,139 which has been herein incorporated by reference.

As can be seen in FIGS. 16 and 17, in various embodiments, a closure lock switch 151 may be mounted in the hook 150 such that that is activated only when the hook 150 is latched in place. However, the closure lock switch 151 may be mounted in the pistol grip portion 26 for activation by the closure trigger 18 when the closure trigger 18 is locked in position. In still other alternative embodiments, the closure lock switch 151 is mounted to the end effector such that it is activated only when the anvil or other movable portion is in the "closed" position. Regardless of the specific location of the closure lock switch 151, in various embodiments, the closure lock switch is a normally open switch that will be closed upon locking of the closure trigger 18 or otherwise manipulating the end effector to a "closed" position.

Figure 18:
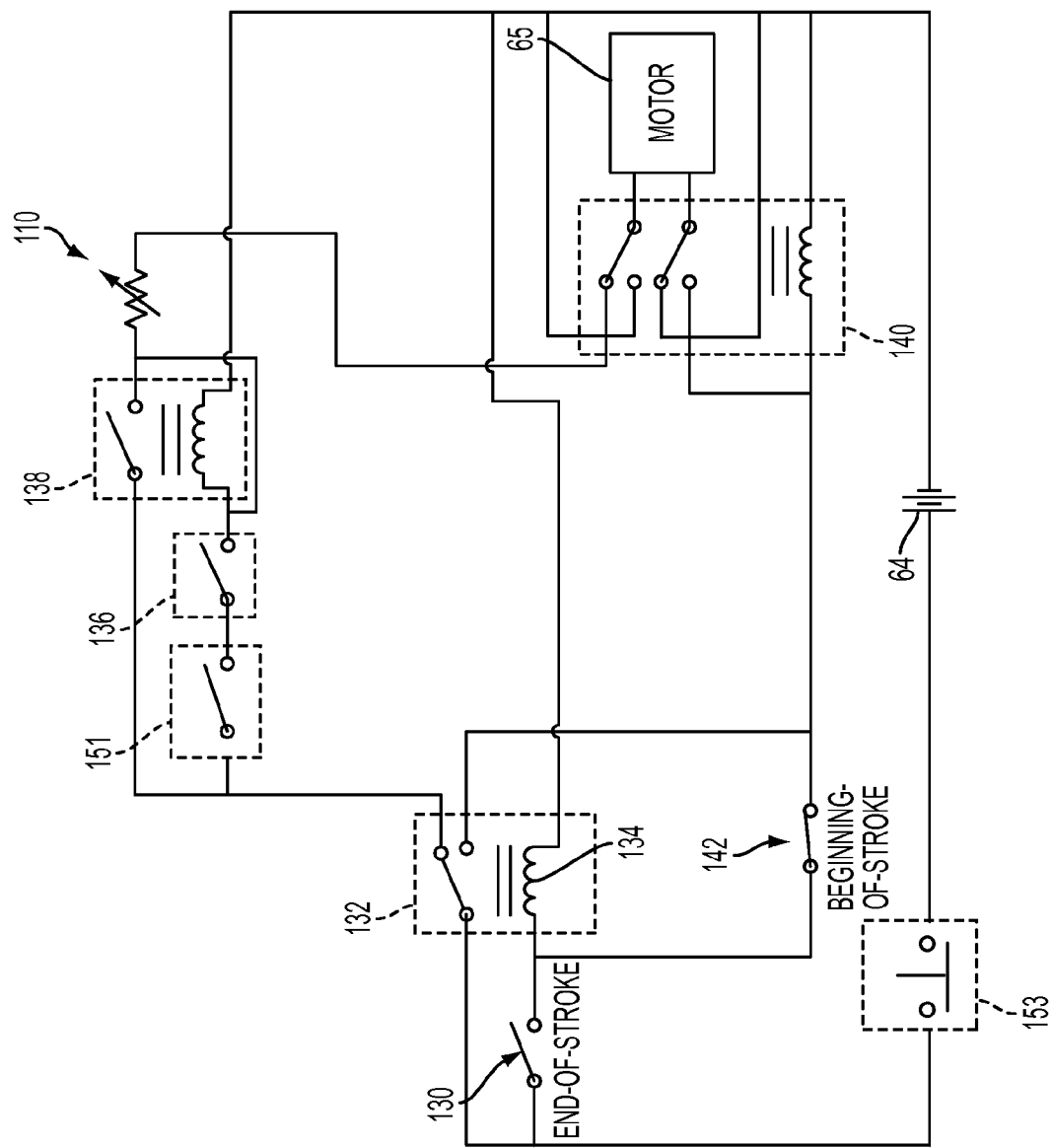
FIG. 18 is a schematic diagram of another current control circuit used in the instrument according to various embodiments of the present invention.

FIG. 18 is a schematic diagram of an electrical circuit of the instrument 10 according to various embodiments of the present invention illustrating the use of the closure lock switch 151. As can be seen in that Figure, current will not be permitted to flow from the battery 64 to the motor 65 even if a cartridge is present unless the closure lock switch 151 is closed. Thus, the motor 65 cannot be operated unless the closure trigger is in the locked closed position which also reflects that the end effector is in the closed state.

Various embodiments may further include a start switch 153 that must be activated by the surgeon before current will be permitted to flow from the battery 64 to the other circuit components and ultimately to the motor 65. Start switch 153 is normally open and may be located at a convenient location on the handle 6. See FIG. 1. Thus, in these embodiments, even if the end effector contains a cartridge and the closure trigger 18 is locked in a closed position, current will not be permitted to flow to the motor 65 until the start switch 153 is closed by the surgeon. In alternative embodiments, the start switch 153 may comprise a mechanical switch that prevents the firing trigger 20 from being physically rotated toward the pistol grip portion unless the switch 153 is moved to an actuated position.

Active adjustable staple height for a powered endocutter: Staple height that is adjustable to the tissue thickness and type has been pursued for many years. Most recently, U.S. patent application Ser. No. 11/231,456, filed Sep. 21, 2005, now U.S. Pat. No. 7,407,078 and U.S. patent application Ser. No. 11/540,735, filed Sep. 29, 2006, now U.S. Pat. No. 7,467,740, the disclosures of which are each hereby incorporated by reference in their respective entireties generally involve a flexible coupling member or supports that would allow the gap of the instrument to enlarge with loads induced by thicker tissue in the device. This "passive" variable staple height allows the thickness of the tissue to create larger staple forms.

With the introduction of a power source within the instrument this allows for the use of electricity to change the height of an internal element within the dynamic coupling element with would change the height of the staple "actively" by the surgeon or instrument setting the desired height. This internal element could be a shape memory material and the electricity changes its temperature and therefore allows it to change its physical height due to preset configuration. Another viable method would be the inclusion of an electro-active polymer (EAP) that through the introduction of an electric field allows it to change its height and width. Yet a third embodiment would be to utilize a traditional linear electrical stepper element that can ratchet a small adjustable screw element within the coupling beam that would adjust its height.

Figure 19:
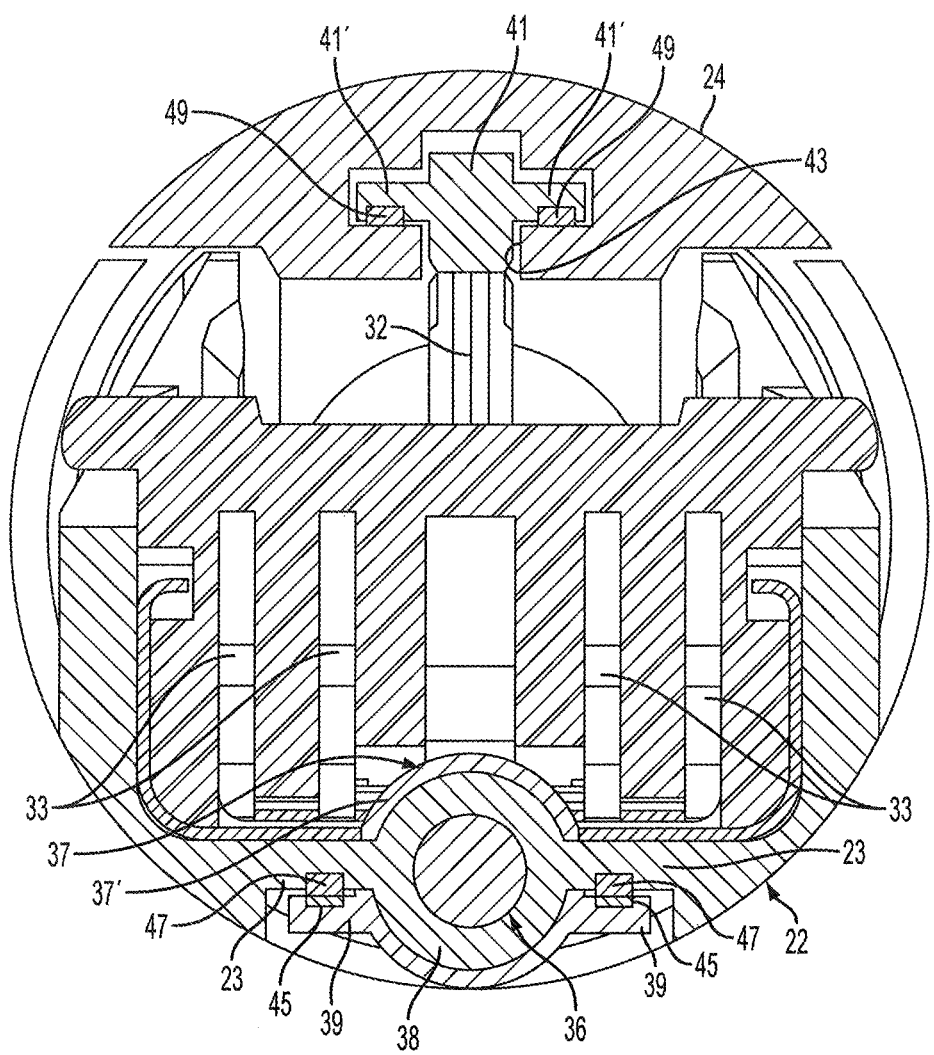
FIG. 19 is a cross-sectional view of an end effector embodiment of the present invention.
Figure 20:
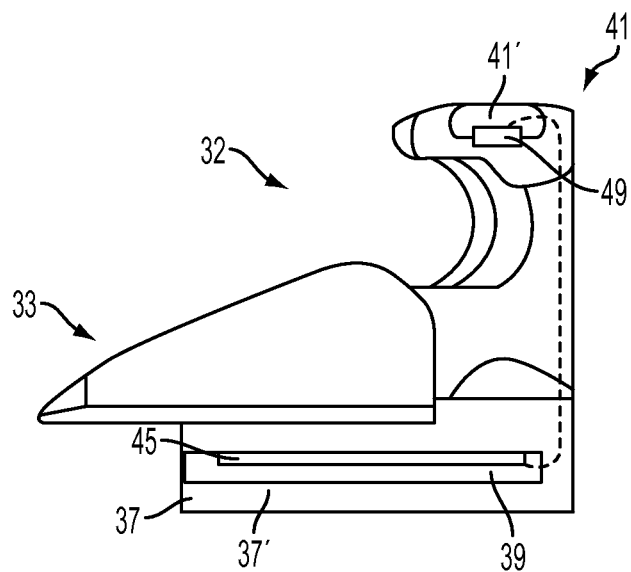
FIG. 20 is a side elevational view of a knife assembly or actuator embodiment of the present invention.

More specifically and with reference to FIGS. 19 and 20, an end effector 12 of various embodiments of the present invention is shown in cross-section with the anvil 24 in a closed or clamped position. As can be seen, the cutting instrument or knife 32 has a lower actuator portion 37 that has a threaded sleeve or nut portion 37' that is configured to threadably engage the helical screw shaft 36. In addition, a fin 39 protrudes laterally from each lateral side of the nut portion 37 to confront corresponding slide portions 23 of the channel 22. As can also be seen in FIG. 19, the knife 32 has an upper actuator portion 41 that is sized to be received within a longitudinal T-shaped slot 43 in the anvil 24. As can be seen in FIG. 19, a pair of upper retainer pins 41' protrude laterally from each side of the upper actuator portion 41 of the knife 32. Each upper retainer pin 41' is configured to extend into a corresponding portion of the T-shaped slot 43 provided in the anvil 24. Thus, as the knife 32 is driven distally through the end effector 12, the fins 39 and the retainer pins 41' serve to limit the amount of space between the anvil 24 and the cartridge 34 to a maximum amount of predetermined space.

Various embodiments of the present invention are provided with means for adjusting the amount of space between the anvil 24 and the cartridge 34 installed within the channel 22. For example, in some embodiments, each fin 39 supports a sled contact 45 for sliding contact with corresponding electrical contacts 47 that are mounted within each slide portion 23 of the channel 22. The electrical contacts 47 are elongated and extend within the channel 22 so that the sled contacts 45 are always on contact with their corresponding electrical contact 47 as the knife 32 is driven within the channel 22. Electrical contacts 47 are connected to the power source or battery 64 and are configured to receive current therefrom when the motor 65 is powered to drive the knife 32 distally. Also in certain embodiments, an electrically responsive height adjustment member 49 is mounted to each retainer pin 41' as shown in FIG. 19. The height adjustment members 49 are electrically coupled to the sled contacts 45 to receive electrical current therefrom. In various embodiments, the height adjustment members 49 may comprise shape memory material that, when electrified, changes its physical height due to a preset configuration. Thus, depending upon the amount of current received, the height adjust member members 49 may expand and force the anvil 24 towards the cartridge 34 to thereby reduce the amount of space therebetween. The amount that such material is proportional to the amount of current received and is known. A control circuit (not shown) may be employed to control the amount of expansion and hence the amount of space between the anvil 24 and the cartridge 34. In other embodiments, the height adjustment material comprises an electro-active polymer (EAP) that is retained within a pocket in the pin 41 or is otherwise attached thereto.

Figure 21:
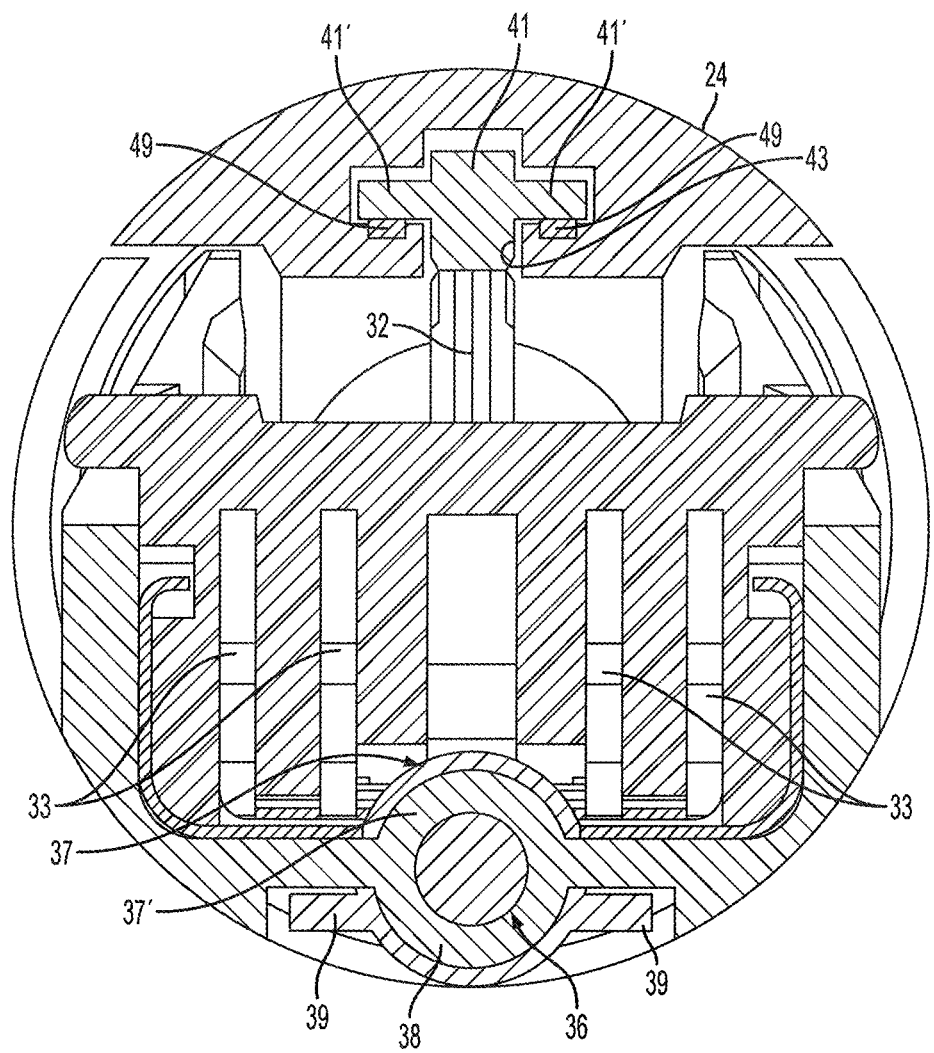
FIG. 21 is a side elevational view of another knife assembly or actuator embodiment of the present invention.

FIG. 21 illustrates another embodiment that is similar to the embodiment depicted in FIG. 19. However, in this embodiment, the height adjustment members 49 are mounted in the anvil 24 and receive current from the power source through conductors attached directly thereto. Thus, in this embodiment, the contacts 43 and 45 as described above are not needed.

Figure 22:
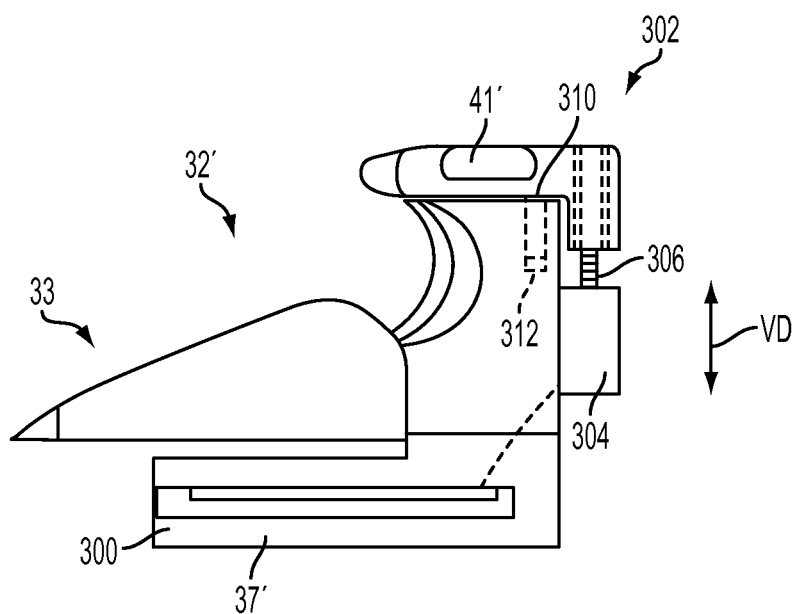
FIG. 22 is a side elevational view of another knife assembly or actuator embodiment of the present invention.

FIG. 22 illustrates an alternative knife assembly 32' that is substantially identical to the knife assembly 32 described above, except that the retainer pins 41' are mounted to a separate upper actuator portion 302 that is selectively movable in a vertical direction "VD" relative to a lower portion 300 of the knife assembly 32'. A second motor 304 may be mounted to the lower portion 300 and have a lead screw 306 that threadably engages a nut portion 308 of the upper retainer portion 302. The upper retainer portion has a "T"-shaped tongue portion 310 that slidably extends into a correspondingly shaped slot 312 in the lower portion 300 to prevent rotation of the upper retainer portion 302 relative to the lower retainer portion 300 while permitting the upper retainer portion 302 to move vertically relative thereto. Thus, the distance between the upper and lower retainer portions 302, 300 may be adjusted by powering the second motor 304. Accordingly, if the surgeon wants to reduce the amount of space between the anvil 24 and the cartridge 34, second motor 304 is powered to rotate in a first direction to draw the upper retainer portion 302 towards the lower retainer portion 300. If however, the surgeon desires to increase the amount of space between the anvil 24 and the cartridge 34, the second motor 304 is rotated in an opposite direction.

Figure 23:
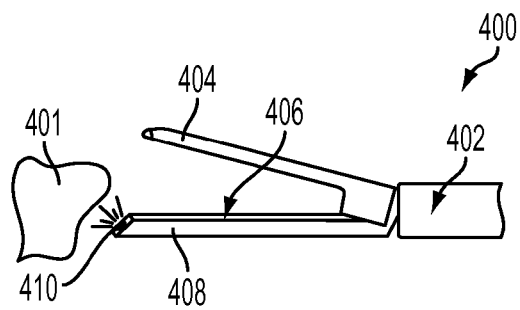
FIG. 23 is a perspective view of a distal end of surgical stapler in accordance with an embodiment of the present invention.

Various embodiments of the present invention include end-effector illumination methods and methods for illuminating the surgical site when employing a powered endocutter. Currently when the end-effector is in or near its deployment position it is sometimes difficult for the surgeon to visualize the treatment site as there are shadows cast by adjacent structures as well as the end-effector may even be behind another structure entirely. FIG. 23 illustrates in general form, a distal end 402 of a surgical stapler 400 of various embodiments of the present invention which includes an anvil 404, a cartridge body 406, and channel 408. As seen from that Figure, an additional light source 410 may be positioned on the end of the cartridge body 406 to illuminate tissue 401. This light source 410 could be any combination of practical means that convert electrical energy to light including but not limited to semiconductor (such as LED), a conventional incandescent or filament bulb, electroluminescent or laser that may be powered from a battery supported in the instrument handle or in other embodiments, powered by alternating current. Such arrangements would allow the surgeon to not only light up the treatment site directly, they could allow for backlighting of structures to see the internal components like vasculature and facilitate the use of a laser pointer through a traditional scope to point out areas of interest to others.

Figure 24:
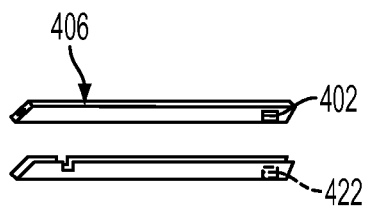
FIG. 24 is a perspective view of a distal end of surgical stapler in accordance with an embodiment of the present invention with the cartridge removed from the channel.

In various embodiments, one or more contacts 420 are provided on the back of the cartridge body 406 that are configured to engage contacts 422 within the channel 408. See FIG. 24. This would allow the surgeon to energize the light 410 as needed by energizing contact set via a switch positioned on the handle 430. This switch could even have variable intensity as the one described in could control the actuation speed of the main, device. Other lighting arrangements for lighting the end of an anvil attached to a circular surgical stapler are disclosed in U.S. Patent Application Publication No. US 2010/0096435 A1, entitled "Surgical Stapling Instrument With Apparatus For Providing Anvil Position Feedback", Published Apr. 22, 2010, the entire disclosure of which is hereby incorporated by reference.

Figure 25:
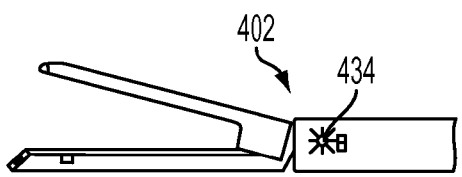
FIG. 25 is a view of a distal end of surgical stapler in accordance with an embodiment of the present invention similar to FIG. 1 showing a lockout indicator.
Figure 26:
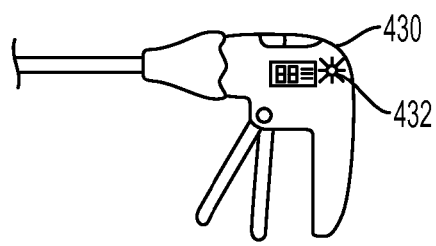
FIG. 26 is a perspective view of a proximal end of surgical stapler in accordance with an embodiment of the present invention.

U.S. Patent Application Publication No. 2007/0175949 A1, entitled "Surgical Instrument Having a Feedback System", Published Aug. 2, 2007, the entire disclosure of which is hereby incorporated by reference, further discloses in FIGS. 45-47 of that Publication output displays that could show among other this position feedback of the end-effector, lockout status, number of firings etc. This would minimize one of the more difficult issues for the user, which is the identification of the status of a device, especially the lockout status of the device without actuating the device. An additional feedback that would be helpful for the user would be immediate feedback as to the status of the cartridge when it is loaded. As in the above application it could be rolled up into the lockout indication on the handle 430. An indicator 432 (such as an LED, glass bulb, LCD, sonic enunciator, vibrator, etc.) could solely be associated with the status of a cartridge lockout means or mechanism such that it providing this information to the surgeon. This LED could be located on the handle 430. See FIG. 26. Alternatively an indicator 434 could be located near the distal end 402 which would provide immediate information to the surgeon and loader if the cartridge is "good to go" or not. See FIG. 25. This can be accomplished with a switch or set of contacts associated directly with the mechanical lockout. The switch or contacts complete a circuit such that the indicator provides appropriate information. This completed contact set could be through a conductive element within the sled (part 33 in U.S. Patent Application Publication No. US 2007/0175958) and the two contacts could be in the proximal position of the channel (part 22). Another way to detect lockout status is indirectly through instrument status (example 1: loaded cartridge and no attempt to fire would indicate lockout is not engaged; example 2: fired instrument and no new cartridge installed would indicate lockout is engaged; etc.). Another embodiment would be to place the LED or visual indication cue on the cartridge itself. When the cartridge is snapped into place it creates a contact that supplies the cartridge with power. Should the cartridge be fired not only does the mechanical lockout stop the advancement of the knife the cartridge circuit light up the LED on the cartridge informing the surgeon on the scope monitor that the cartridge is locked out. This could be further expanded by placing a small battery or other charge accumulator within the cartridge itself to eliminate the need for a power connection to the main device. Also the cartridge circuit could be set to light the lockout light whenever the device is closed to inform the user there is a spent cartridge in the device.

Indication feedback for powered articulation and cartridge color: Indicating the type of cartridge installed (color) and angle of articulation is considered useful to the surgeon. The indication of articulation angle could be indicated in several ways including numerically or graphically as in an arc of LEDs. The location of this indication could be on the handle in a convenient location or on the shaft of the device just proximal to the end-effector. The end-effector effector feedback could be passive or active. The active would light up additional LEDs to show the angle. The passive could just show a half pie lighted up so the surgeon could intuit how articulated the end-effector is. As we further explore the surgical procedures it becomes more and more obvious that the surgeon's eyes need to be on the surgical site not on the handle of the instrument. We also begin to understand the surgeon's need for complete status feedback from the device. Articulation angle could be illuminated as part of the articulation joint itself. With lights, LEDs, etc. denoting the differing angle or even a small LCD denoting angle in degrees. This would allow the surgeon to have some feedback on the angle off of straight so he/she can easily navigate back to this angle after removal and reinsertion. Another issue is "obvious" indication of what color cartridge is in the device. This can be accomplished by a color coded light array on either the end-effector or the cartridge. This information could also be transmitted back to the handle to display a "redundant" display to assure there is minimal confusion as to what cartridge is in the jaws. Another improvement could include a small leaf spring contact connected to the proximal deck of the cartridge that indicates if a minimum tissue pressure has been achieved within the jaws. This minimum pressure would at the very least indicate if a thick tissue cartridge is being used in thin tissue applications, as it would not light if insufficient tissue pressure on the deck were present.

There is a possible need of a method for the introduction of non-sterile battery packs (possibly with the electronics integral to the battery pack if programmable logic becomes a key customer need). A patent already exists within the orthopedic drill industry for the insertion of a non-sterile battery pack within a separately sterilized re-useable device. This innovation is intended to improve that concept by utilizing the disposable device sterile packaging to protect the sterility of the instrument during the insertion of the non-sterile battery pack. A further improvement would be the inclusion of a "hatch" door designed within the instrument and closable after the pack has been inserted but before the device is removed from the final sterile packaging. This hatch would then "contain" the non-sterile battery that could contaminate the sterile surgical field. The method here would be to include an additional layer of packaging that would have a perforated area that the battery could be pushed through, either rupturing the extra layer and allowing the battery through or going with the electrode set of the battery only to be ruptured by the exposable pin tips of the battery at complete insertion. An alternative of this would be to have the internal terminals of the gun (deep inside the battery protection cavity) rupture the sterile barrier and seat within pinholes in the battery pack. The hatch could then be closed through the sterile pack sealing the system. The gun could then be handed into the sterile field normally as any sterile device could.

Position Locator Embodiments I Linear encoder and load control of motor parameters: U.S. Pat. Nos. 6,646,307 and 6,716,223 disclose the mechanisms for the measurement of rotation and related torque to control motor parameters and optimizing of those parameters based on identification of end-effector configurations and loading. U.S. Patent Application Publication No. 2007/0175958 shows a method through the use of a threaded length of the primary shaft in FIGS. 8-13 how this type of linear motion control could be used to control the trigger location. The same type of method could be used for electronic linear control methods. The end-effector could identify its length and type mechanically by depressing at least one spring biased plunger, which could identify to the handle the type, and length it would allow the motor to run. The motor rotation could be converted from rotary motion to linear rack or cable motion, which could then be used to adjust motor voltage, current, and speed to affect the desired linear motion of the control slide. The control slide could then be directly coupled to the knife drive motion. This control slide could have discrete or continuous "stop" locations that the plunger identifier marks as the max "go to" linear displacement before retraction Identification of modular reloads with linear drive: A useful feature for a surgical instrument is the ability to identify which end-effector has been attached to the instrument. In the case of a powered surgical stapler, several different types of end-effectors could be attached. Additionally, a type of end-effector may have at least one function and/or feature that is selectively utilized or enabled. Disclosed are means for identifying which end-effector is attached. Note that the "type" of end-effector referenced below is not limited to mechanical, pneumatic or hydraulically coupled end-effectors. The instrument may take different actions, adjust operating parameters, indicate available functions etc. as a result of detecting this end effector.

The end-effector has an electrical connection that is made when it is attached to the instrument. The instrument communicates with the end-effector and reads at least one of several types of signals. A switch position or contact position indicates which type of end-effector is present. A passive element is measured for impedance and the result indicates which type of end-effector is present.

The end-effector has a radio frequency link to the instrument and data is transferred in at least one direction between the end-effector and the instrument.

The end-effector has an acoustic link to the instrument and data is transferred in at least one direction between the end-effector and the instrument.

The end-effector has an optical link to the instrument and data is transferred in at least one direction between the end-effector and the instrument.

The end-effector has mechanical link that engages elements (such as switches or contacts) in the instrument that identify it and thereby data is transferred in at least one direction between the end-effector and the instrument.

While the present invention has been illustrated by description of several embodiments and while the illustrative embodiments have been described in considerable detail, it is not the intention of the applicant to restrict or in any way limit the scope of the appended claims to such detail. Additional advantages and modifications may readily appear to those skilled in the art.

For example, although the embodiments described above have advantages for an endoscopically employed surgical severing and stapling instrument 10, a similar embodiments may be used in other clinical procedures. It is generally accepted that endoscopic procedures are more common than laparoscopic procedures. Accordingly, the present invention has been discussed in terms of endoscopic procedures and apparatus. However, use herein of terms such as "endoscopic", should not be construed to limit the present invention to a surgical instrument for use only in conjunction with an endoscopic tube (i.e., trocar). On the contrary, it is believed that the present invention may find use in any procedure where access is limited to a small incision, including but not limited to laparoscopic procedures, as well as open procedures.

Any patent, publication, or information, in whole or in part, that is said to be incorporated by reference herein is incorporated herein only to the extent that the incorporated material does not conflict with existing definitions, statements, or other disclosure material set forth in this document. As such the disclosure as explicitly set forth herein supersedes any conflicting material incorporated herein by reference.

While this invention has been described as having exemplary designs, the present invention may be further modified within the spirit and scope of the disclosure. This application is therefore intended to cover any variations, uses, or adaptations of the invention using its general principles. Further, this application is intended to cover such departures from the present disclosure as come within known or customary practice in the art to which this invention pertains.

What is claimed is:

1. A surgical fastener apparatus comprising:
   a handle;
   an elongated shaft including a proximal end attached to said handle and a distal end extending therefrom;
   an end effector comprising:
      a pair of jaws pivoted at one end of the end effector and being pivotally movable between an open and closed position; and
      a cartridge containing a plurality of surgical fasteners operably supported by said end effector and wherein said surgical fastener apparatus further comprises:
   an electrically powered actuator for deploying said surgical fasteners, said actuator comprising a power source and a motor; and
   means for adjusting an amount of spacing between said jaws when said jaws are in said closed position in response to an application of electrical current from the power source to the means for adjusting.

2. The surgical fastener apparatus of claim 1 wherein said end effector comprises:
   an elongated channel configured to operably support said cartridge therein; and
   an anvil pivotally coupled to said elongated channel and being selectively pivotable between said open and closed positions.

3. The surgical fastener apparatus of claim 2 wherein said actuator comprises an actuator portion movable within said end effector in response to activation motions received from said motor, said actuator portion having a lower actuator portion slidably engaging said elongate channel and an upper portion having a pair of retainer members configured to slidably engage said anvil.

4. The surgical fastener apparatus of claim 3 wherein said means for adjusting comprises a height adjustment member on each of said retention members, each said height adjustment member positioned between said retention member and a corresponding portion of said anvil and in electrical communication with said power source, each said height adjustment member having a thickness that increases in response to electrical current from said power source.

5. The surgical fastener apparatus of claim 4 further comprising:
   at least one electrical contact in said elongated channel and electrically communicating with said power source; and
   at least one slide contact on said lower actuator, said at least one slide contact in sliding electrical contact with a corresponding one of said at least one electrical contact in said elongate channel and in electrical communication with said height adjustment members to transmit said electrical current thereto.

6. The surgical fastener apparatus of claim 4 wherein said height adjustment members comprise electro-active polymer material.

7. The surgical fastener apparatus of claim 3 wherein said means for adjusting comprises a height adjustment member on said anvil corresponding to each of said retention members on said upper actuator portion, each said height adjustment member positioned between said corresponding retention member and said anvil and in electrical communication with said power source, each said height adjustment member having a thickness that increases in response to electrical current from said power source.

8. The surgical fastener apparatus of claim 3 wherein said upper actuator portion is movable relative to said lower actuator portion.

9. The surgical fastener apparatus of claim 8 wherein said means for electrically adjusting comprises means for electrically moving said upper actuator portion relative to said lower actuator portion.

10. The surgical fastener apparatus of claim 9 wherein said means for electrically moving comprises a second electric motor coupled to said upper and lower actuator portions and in electrical communication with said power source.

11. The surgical fastener apparatus of claim 10 further comprising:
   at least one electrical contact in said elongated channel and electrically communicating with said power source; and
   at least one slide contact on said lower actuator, said at least one slide contact in sliding electrical contact with a corresponding one of said at least one electrical contact in said elongate channel and in electrical communication with said second electric motor.

12. A surgical fastener apparatus comprising:
   a handle;
   an end effector operably coupled to said handle, said end effector comprising:
      an elongated channel configured to support a cartridge therein;
      an anvil pivotably supported on said elongated channel for selective pivotal movement toward said elongated channel to closed positions and away from said elongated channel to open positions, said anvil including an elongated slot therein;
      an actuator member movably supported within said elongated channel and selectively movable from an unactuated proximal position to actuated positions within said elongated channel, said actuator member comprising:
         a lower actuator portion slidably engaging said elongated channel;
         an upper actuator portion configured to protrude into said elongated slot;
         a retainer member protruding from each lateral side of said upper actuator portion in a direction that is substantially transverse to said elongated slot in said anvil; and
         a height adjustment member on each said retainer member, each said height adjustment member including a thickness that increases in response to an application of electrical current thereto to selectively adjust a spacing between said anvil and said elongated channel when said anvil is in one of said closed positions.

13. The surgical fastener apparatus of claim 12 further comprising:
   at least one electrical contact in said elongated channel and electrically communicating with said power source; and
   at least one slide contact on said lower actuator portion, said at least one slide contact in sliding electrical contact with a corresponding one of said at least one electrical contact in said elongate channel and in electrical communication with said second electric motor.

14. The surgical fastener apparatus of claim 12 wherein said height adjustment members are on said anvil adjacent each lateral side of said elongated slot for confronting relationship with said retainer members.

15. The surgical fastener apparatus of claim 14 further comprising:
   at least one electrical contact in said elongated channel and electrically communicating with said power source; and
   at least one slide contact on said, lower actuator portion, said at least one slide contact in sliding electrical contact with a corresponding one of said at least one electrical contact in said elongate channel and in electrical communication with said second electric motor.

16. The surgical fastener apparatus of claim 14 wherein said height adjustment members comprise electro-active polymer material.

17. The surgical fastener apparatus of claim 12 wherein said height adjustment members comprise electro-active polymer material.

18. A surgical fastener apparatus comprising:
   a handle;
   an end effector operably coupled to said handle, said end effector comprising:
      an elongated channel configured to support a cartridge therein;
      an anvil movably supported on said elongated channel for selective movement toward said elongated channel to closed positions and away from said elongated channel to open positions, said anvil having an elongated slot therein;
      an actuator member movably supported within said elongated channel and comprising:
         a lower actuator portion slidably engaging said elongated channel;
         an upper actuator portion configured to protrude into said elongated slot and movable relative to said lower actuator portion;
         a retainer member protruding from each lateral side of said upper actuator portion in a direction that is substantially transverse to said elongated slot in said anvil; and
         a first electrically powered motor operably interfacing with at least one of said upper and lower actuator portions to axially move the upper and lower actuator portions as a unit between an unactuated proximal portion to actuated positions within said elongated channel; and
         a second electrically powered motor coupled to said upper and lower actuator portions for selectively moving said upper actuator portion relative to said lower actuator portion.

19. The surgical fastener apparatus of claim 18 further comprising:
   at least one electrical contact in said elongated channel and electrically communicating with said power source; and
   at least one slide contact on said lower actuator, said at least one slide contact in sliding electrical contact with a corresponding one of said at least one electrical contact in said elongate channel and in electrical communication with said second electric motor.

* * * * *